(12) United States Patent
Cardozo et al.

(10) Patent No.: US 7,683,059 B2
(45) Date of Patent: Mar. 23, 2010

(54) TRIAZOLE COMPOUNDS AND USES RELATED THERETO

(75) Inventors: Mario G. Cardozo, San Francisco, CA (US); Jay P. Powers, Pacifica, CA (US); Hiroyuki Goto, Takatsuki (JP); Kazuhito Harada, Osaka (JP); Katsuaki Imamura, Tokyo (JP); Makoto Kakutani, Takatsuki (JP); Isamu Matsuda, Tokyo (JP); Yasuhiro Ohe, Tokyo (JP); Shinji Yata, Tokyo (JP)

(73) Assignee: Amgen Inc., Thousand Oaks, CA (US)

( * ) Notice: Subject to any disclaimer, the term of this patent is extended or adjusted under 35 U.S.C. 154(b) by 822 days.

(21) Appl. No.: 10/587,846

(22) Filed: Sep. 5, 2006

(65) Prior Publication Data

US 2008/0249084 A1 Oct. 9, 2008

Related U.S. Application Data

(60) Provisional application No. 60/515,537, filed on Oct. 28, 2003.

(51) Int. Cl.
*A61K 31/4196* (2006.01)
*A61K 31/5377* (2006.01)
*C07D 413/12* (2006.01)
*C07D 249/08* (2006.01)

(52) U.S. Cl. .............. 514/236.2; 544/106; 544/111; 544/132; 548/262.2; 548/267.2; 514/231.2; 514/235.8; 514/383

(58) Field of Classification Search .............. 544/106, 544/111, 132; 548/262.2, 267.2; 514/231.2, 514/231.5, 236.2, 383
See application file for complete search history.

(56) References Cited

U.S. PATENT DOCUMENTS 6,730,690 B2 * 5/2004 Olson et al. .............. 514/383
7,179,802 B2 * 2/2007 Olson et al. .............. 514/211.1

FOREIGN PATENT DOCUMENTS

WO    WO 00/39125 A1    7/2000
WO    WO 03/104207 A2    12/2003

OTHER PUBLICATIONS

Supplemental Partial European Search Report for the Corresponding European Patent Application No. 04796647, dated Aug. 20, 2008 (3 pgs.).

\* cited by examiner

*Primary Examiner*—Golam M Shameem
(74) *Attorney, Agent, or Firm*—Foley & Lardner LLP

(57) ABSTRACT

The present invention provides a triazole compound of the following formula: a prodrug thereof or a pharmaceutically acceptable salt thereof. The above-mentioned triazole compound is useful as a therapeutic drug for the treatment of diabetes, obesity or metabolic syndrome.

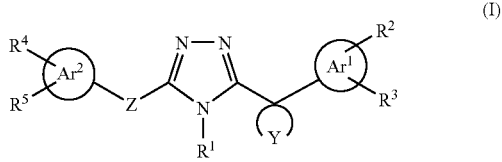

18 Claims, No Drawings

TRIAZOLE COMPOUNDS AND USES RELATED THERETO

TECHNICAL FIELD OF THE INVENTION

The present invention relates to triazole compounds useful for, for example, the treatment or prophylaxis of diabetes, obesity and metabolic syndrome.

BACKGROUND OF THE INVENTION

11Beta-hydroxysteroid dehydrogenase 1 (hereinafter, "11beta-HSD1" or "HSD1") catalyzes the interconversion of glucocorticoids (hereinafter, "GC") between inert 11-keto forms (e.g. cortisone, 11-dehydrocorticosterone) and active 11beta-hydroxy forms (e.g. cortisol, corticosterone, respectively). The enzyme, in vivo, prefers the reductase direction from the 11-keto to the 11beta-hydroxy, in other words, the production of active GC.

11Beta-HSD1 is ubiquitously expressed, most notably in liver, lung, adipose tissue, vasculature, ovary and the central nervous system.

Until recently, experimental results have suggested that the active form of GC produced through HSD1 as well as the enzyme itself is involved in several biological actions and diseases.

For example, the active GC is known to stimulate gluconeogenic enzymes and have effects at least in part in inducing hyperglycemia. In this situation, HSD1 can be a second source of GC production in addition to the adrenal glands.

As another example, continuous excessiveness of the active GC in peripheral tissues, as observed in Cushing's syndrome, leads to insulin resistance, where HSD1 is considered to have an important role.

Also, in adipose tissue, active GC is demonstrated to enhance the differentiation of preadipocytes into adipocytes. Mature adipocytes express HSD1 activity, which causes an increase in local concentration of the active form and further expansion of adipose tissue. Such an action of HSD1 should be critical in pathogenesis of obesity.

In addition, a local immunosuppressive effect of HSD1 in placental deciduas, and a relationship between the expression of the enzyme in adrenal cortex and the induction of adrenaline synthesis, are suggested.

(The above are referred to in: Quinkler M, Oelkers W & Diederich S (2001) European Journal of Endocrinology Vol. 144, Pages 87-97; and Seckl J R & Walker B R (2001) Endocrinology Vol. 142, Pages 1371-1376.)

According to the above suggestions, it is expected that drugs having inhibitory effects against HSD1 would be useful for treating or preventing diabetes mellitus, obesity, metabolic syndrome in connection with any of such diseases, or any other diseases which occur by reason of the actions of HSD1.

Diabetes mellitus, main feature of which disease is chronic hyperglycemia, introduces various metabolic abnormalities and shows symptoms of thirst, polydipsia, polyuria, and so on based on high glucose concentration. Continuing hyperglycemic state would also lead to diabetic complications such as retinopathy, nephropathy, neuropathy, and myocardial and/or cerebral infarction by reason of arteriosclerosis.

In treating diabetes, moderate suppression of hyperglycemia is critical in order that onset and progress of the complications would be repressed. For these purposes, dietetics, ergotherapy and pharmacotherapy are utilized in combination on a suitable basis and, amongst the pharmacotherapy, many approaches different in mechanisms of action have been attempted. In spite of those various existing methods, sufficient therapeutic effect has not ever been achieved.

Obesity is defined as a state of fatness coinciding with any disease that would be improved or not be progressed in case of weight decrease (e.g. diabetes, hyperlipidemia, hypertension) or with an excessive amount of fat in viscera. It is considered that, if such a state should continue, at least two of diabetes, hyperlipidemia, hypertension and etc. would concur, and then onset of myocardial and/or cerebral infarction by reason of arteriosclerosis would occur.

Major therapeutic methods in treating obesity are dietetics and ergotherapy, and pharmacotherapy is undertaken only if necessary, for example, because of difficulty in the first two alternatives. However, the existing drugs have several problems in adverse effects and usages, since most of them suppress feeding mainly via central action.

In consequence, development of any drug to treat diabetes and/or obesity with a novel mechanism of action has so far been required. Under these circumstances, it is expected that drugs having inhibitory effects against HSD1 would be useful as another alternative with separate mechanistic approach to treat diabetes mellitus, as well as a novel "adipose tissue-acting" class among other drugs against obesity.

As drugs in development to treat diabetes and/or obesity through inhibition of HSD1, for example, WO 03/065983 discloses triazole compounds of the following general formula:

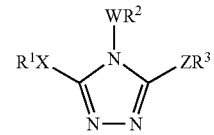

[wherein:
$R^1$ is unsubstituted or substituted adamantyl;
W is $-N(R^a)-$ or single bond;
X is $-CH_2-$ or single bond;
Z is $-S-$ or single bond;
$R^a$ is $-H$ or $C_{1-6}$ alkyl unsubstituted or substituted with one to five fluorines;
$R^2$ is $-H$, unsubstituted or substituted $C_{1-10}$ alkyl, unsubstituted or substituted $C_{2-10}$ alkenyl, $-CH_2CO_2H$, $-CH_2CO_2C_{1-6}$ alkyl, $-CH_2CONHR^a$, $-(CH_2)_{0-2}C_{3-9}$ cycloalkyl (optionally having double bonds, and either unsubstituted or substituted), $-(CH_2)_{0-2}C_{5-12}$ bicycloalkyl (optionally having double bonds, and either unsubstituted or substituted), $-(CH_2)_{0-2}$ adamantyl (either unsubstituted or substituted) or $-(CH_2)_{0-2}R$;
$R^3$ is $-H$, unsubstituted or substituted $C_{1-10}$ alkyl, unsubstituted or substituted $C_{2-10}$ alkenyl, $-YC_{3-9}$ cycloalkyl (optionally having double bonds, and either unsubstituted or substituted), $-YC_{5-12}$ bicycloalkyl (optionally having double bonds, and either unsubstituted or substituted), -Yadamantyl (either unsubstituted or substituted) or YR;
R is benzodioxolane, furan, tetrahydrofuran, thiophene, tetrahydrothiophene, dihydropyran, tetrahydropyran, pyridine, piperidine, benzofuran, dihydrobenzofuran, benzothiophene, dihydrobenzothiophene, indole, dihydroindole, indene, indane, 1,3-dioxolane, 1,3-dioxane, phenyl or naphthyl (any such R unsubstituted or substituted); and
Y is $-(CH2)_{0-2}-$ or $(-HC=CH-)$].

However, any description under said application does not disclose nor refer to any of the compounds having the structure of the present invention.

The compounds of the present invention improve physicochemical (stability, etc.) and biological (activity to inhibit HSD1, specificity, bioavailability, metabolism, etc.) profiles, as a result of the selection of structural characteristics as disclosed herein.

SUMMARY OF THE INVENTION

According to the present invention, it has been found that triazole compounds represented by the following formula have superior HSD1 inhibitory activity, and are useful as HSD1 inhibitors or therapeutic drugs of diabetes or obesity.

The present invention provides the following.

(1) A triazole compound represented by the following formula:

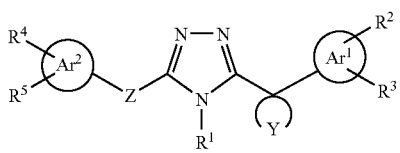

wherein $R^1$ is an alkyl group or a cycloalkyl group wherein the alkyl group and the cycloalkyl group are optionally substituted by 1 to 5 substituents each independently selected from a halogen atom, —$CF_3$, —OH, —$NH_2$, an alkoxy group, a cycloalkyl group, an alkenyl group, —COOH, —CO—O-alkyl, —CO—N($R^7$)($R^8$), —N($R^7$)—CO—$R^8$, an aryl group and a heteroaryl group
  wherein $R^7$ and $R^8$ are each independently a hydrogen atom or an alkyl group, and the aryl group and the heteroaryl group are optionally substituted by 1 to 3 substituents each independently selected from a halogen atom, a haloalkyl group, an alkyl group, $(CH_2)_n$—OH, —N($R^9$) ($R^{10}$), —CN, —$NO_2$, an alkoxy group, a cycloalkyl group, an alkenyl group, —CO—$R^{11}$, an aryl group and a heteroaryl group
    wherein n is 0-3, $R^9$ and $R^{10}$ are each independently a hydrogen atom, an alkyl group or —CO-alkyl, and $R^{11}$ is —OH, an alkoxy group, an alkyl group or —N($R^{12}$) ($R^{13}$) wherein $R^{12}$ and $R^{13}$ are each independently a hydrogen atom or an alkyl group;

Y is a cycloalkyl group or a heterocycloalkyl group wherein the cycloalkyl group and the heterocycloalkyl group are optionally substituted by 1 to 3 substituents each independently selected from a halogen atom, a haloalkyl group, an alkyl group, —$(CH_2)_n$—OH, —N($R^9$) ($R^{10}$), —CN, —$NO_2$, an alkoxy group, a cycloalkyl group, an alkenyl group, —CO—$R^{11}$, an aryl group and a heteroaryl group (m, $R^9$, $R^{10}$ and $R^{11}$ are as defined above);

$Ar^1$ is an aryl group or a heteroaryl group;

$R^2$ and $R^3$ are each independently a hydrogen atom, a halogen atom, a haloalkyl group, an alkyl group, —$(CH_2)_n$—OH, —N($R^9$)($R^{10}$), —CN, —$NO_2$, an alkoxy group, a cycloalkyl group, an alkenyl group, —CO—$R^{11}$, an aryl group or a heteroaryl group
  wherein the aryl group and the heteroaryl group are optionally substituted by 1 to 3 substituents each independently selected from a halogen atom, a haloalkyl group, an alkyl group, —$(CH_2)_n$—OH, —N($R^9$) ($R^{10}$), —CN, —$NO_2$, an alkoxy group, a cycloalkyl group, an alkenyl group, —CO—$R^{11}$, an aryl group and a heteroaryl group (m, $R^9$, $R^{10}$ and $R^{11}$ are as defined above);

Z is —(CH($R^{14}$))$_m$—, —(CH($R^{14}$))$_p$—N($R^{16}$)—(CH($R^{15}$))$_q$- or

wherein $Y_1$ is a cycloalkyl group or a heterocycloalkyl group
  wherein the cycloalkyl group and the heterocycloalkyl group are optionally substituted by 1 to 3 substituents each independently selected from a halogen atom, a haloalkyl group, an alkyl group, —$(CH_2)_n$—OH, —N($R^9$)($R^{10}$), —CN, —$NO_2$, an alkoxy group, a cycloalkyl group, an alkenyl group, —CO—$R^{11}$, an aryl group and a heteroaryl group (n, $R^9$, $R^{10}$ and $R^{11}$ are as defined above), p is 0-3, q is 0-3, $R^{14}$ and $R^{15}$ are each independently a hydrogen atom, a halogen atom, a haloalkyl group, an alkyl group, —$(CH_2)_n$—OH, —N($R^9$)($R^{10}$), —CN, —$NO_2$, an alkoxy group, a cycloalkyl group, an alkenyl group, —CO—$R^{11}$, an aryl group or a heteroaryl group
  wherein the aryl group and the heteroaryl group are optionally substituted by 1 to 3 substituents each independently selected from a halogen atom, a haloalkyl group, an alkyl group, —$(CH_2)_n$—OH, —N($R^9$) ($R^{10}$), —CN, —$NO_2$, an alkoxy group, a cycloalkyl group, an alkenyl group, —CO—$R^{11}$, an aryl group and a heteroaryl group (n, $R^9$, $R^{10}$ and $R^{11}$ are as defined above), and $R^{16}$ is a hydrogen atom, a haloalkyl group, an alkyl group, —$(CH_2)_n$—OH, —$(CH_2)_n$CO—$R^{11}$, a cycloalkyl group, an alkenyl group, an aryl group or a heteroaryl group
  wherein the aryl group and the heteroaryl group are optionally substituted by 1 to 3 substituents each independently selected from a halogen atom, a haloalkyl group, an alkyl group, —$(CH_2)_n$—OH, —N($R^9$) ($R^{10}$), —CN, —$NO_2$, an alkoxy group, a cycloalkyl group, an alkenyl group, —CO—$R^{11}$, an aryl group and a heteroaryl group (n, $R^9$, $R^{10}$ and $R^{11}$ are as defined above);

$Ar^2$ is an aryl group, a heteroaryl group or

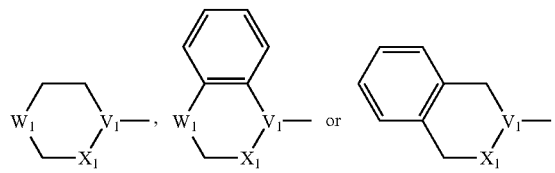

wherein $X_1$ is —$(CH_2)_t$— wherein t is 0-2, $V_1$ is =CH— or =N—, and $W_1$ is —C($R^{17}$)($R^{18}$)—, —O—, —S—, —$SO_2$—, —SO—, —CO— or —N($R^{19}$)—
  wherein $R^{17}$ and $R^{18}$ are each independently a hydrogen atom, an alkyl group, an alkoxy group, a haloalkyl group, —$(CH_2)_r$OH, —CO—$R^{20}$, —N($R^{21}$)($R^{22}$) or -$L_1$-$Ar^3$
    wherein r is 0-3, $R^{20}$ is —OH, an alkoxy group, an alkoxyalkyl group or —N($R^{23}$) ($R^{24}$)

wherein $R^{23}$ and $R^{24}$ are each independently a hydrogen atom, an alkyl group, —$(CH_2)_s$—OH, an alkoxyalkyl group, or in combination form

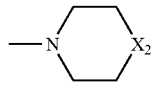

wherein s is 0-3, $X_2$ is —O—, —$(CH_2)_t$— or —$N(R^{25})$—
wherein t is as defined above and $R^{25}$ is a hydrogen atom, —CO—$R^{26}$, —$SO_2$—$R^{26}$ or —$(CH_2)_u$—$Ar^4$
wherein $R^{26}$ is an alkyl group, an alkoxy group, —NH-alkyl or —N(-alkyl)$_2$, u is 0-3, and $Ar^4$ is an aryl group or a heteroaryl group wherein the aryl group and the heteroaryl group are optionally substituted by 1 to 3 substituents each independently selected from a halogen atom, a haloalkyl group, an alkyl group, —$(CH_2)_n$—OH, —$N(R^9)(R^{10})$, —CN, —$NO_2$, an alkoxy group, a cycloalkyl group, an alkenyl group, —CO—$R^{11}$, an aryl group and a heteroaryl group (m, $R^9$, $R^{10}$ and $R^{11}$ are as defined above), $L_1$ is —$(CH_2)_v$—, —O— or —CO—
wherein v is 0-3, and
$Ar^3$ is an aryl group or a heteroaryl group wherein the aryl group and the heteroaryl group are optionally substituted by 1 to 3 substituents each independently selected from a halogen atom, a haloalkyl group, an alkyl group, —$(CH_2)_n$—OH, —$N(R^9)(R^{10})$, —CN, —$NO_2$, an alkoxy group, a cycloalkyl group, an alkenyl group, —CO—$R^{11}$, an aryl group and a heteroaryl group (n, $R^9$, $R^{10}$ and $R^{11}$ are as defined above), and $R^{21}$ and $R^{22}$ are each independently a hydrogen atom, an alkyl group, —CO-alkyl, —CO—O-alkyl or -$L_1$-$Ar^3$ ($L_1$ and $Ar^3$ are as defined above), and
$R^{19}$ is a hydrogen atom, —CO—$R^{26}$, —$SO_2$—$R^{26}$ or —$(CH_2)_u$—$Ar^4$ ($R^{26}$, u and $Ar^4$ are as defined above); and $R^4$ and $R^5$ are each independently a hydrogen atom, a halogen atom, —OH, —$NO_2$, —CN, an alkyl group, an alkoxy group, —CO—$R^{27}$, —$SO_2$—$R^{27}$—CO—$N(R^{28})(R^{29})$ or —$N(R^{30})(R^{31})$
wherein the alkyl group and the alkoxy group are optionally substituted by 1 to 5 substituents each independently selected from a halogen atom, —$CF_3$, —OH, an alkoxy group, a haloalkoxy group, —$N(R^9)(R^{10})$, —CN, —$NO_2$, a cycloalkyl group, an alkenyl group, —CO—$R^{11}$, an aryl group and a heteroaryl group ($R^9$, $R^{10}$ and $R^{11}$ are as defined above),
wherein the aryl group and the heteroaryl group are optionally substituted by 1 to 3 substituents each independently selected from a halogen atom, a haloalkyl group, an alkyl group, —$(CH_2)_n$—OH, —$N(R^9)(R^{10})$, —CN, —$NO_2$, an alkoxy group, a cycloalkyl group, an alkenyl group, —CO—$R^{11}$, an aryl group and a heteroaryl group (n, $R^9$, $R^{10}$ and $R^{11}$ are as defined above)
$R^{27}$ is —OH, an alkoxy group, an alkyl group, —$NH_2$, —NH-alkyl or —N(-alkyl)$_2$,
$R^{28}$ and $R^{29}$ are each independently a hydrogen atom, an alkyl group or —$(CH_2)_w$—$R^{32}$,
wherein w is 0-3 and $R^{32}$ is —OH, —$CF_3$, an alkoxy group, —$CONH_2$ or —$N(R^{33})(R^{34})$ wherein $R^{33}$ and $R^{34}$ are each independently a hydrogen atom, an alkyl group, —CO-alkyl, or in combination form

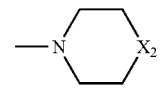

($X_2$ is as defined above)
or $R^{28}$ and $R^{29}$ in combination form

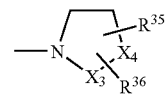

wherein $X_3$ is —CO—, —$CH_2$— or —$CH_2$—$CH_2$—, $X_4$ is —O—, —$(CH_2)_t$—, —$N(R^{25})$— or

wherein $Y_2$ is cycloalkyl or heterocycloalkyl and t and $R^{25}$ are as defined above, and $R^{35}$ and $R^{36}$ are each independently a hydrogen atom, a halogen atom, an alkyl group optionally substituted by —OH, —OH, —CN, —$NO_2$, an alkoxy group, a cycloalkyl group, an alkenyl group, —CO—$R^{37}$, —$N(R^{38})(R^{39})$
wherein $R^{37}$ is —OH, an alkoxy group, —$NH_2$, —NH-alkyl, —N(-alkyl)$_2$ or

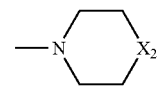

($X_2$ is as defined above)
wherein the alkyl group in —NH-alkyl and —N(-alkyl)$_2$ and the alkoxy group are optionally substituted by 1 to 5 substituents each independently selected from a halogen atom, —$CF_3$, —OH, an alkoxy group, a haloalkoxy group, —$N(R^9)(R^{10})$, —CN, —$NO_2$, a cycloalkyl group, an alkenyl group,
—CO—$R^{11}$, an aryl group and a heteroaryl group ($R^9$, $R^{10}$ and $R^{11}$ are as defined above),
wherein the aryl group and the heteroaryl group are optionally substituted by 1 to 3 substituents each independently selected from a halogen atom, a haloalkyl group, an alkyl group, —$(CH_2)_n$—OH, —$N(R^9)(R^{10})$, —CN, —$NO_2$, an alkoxy group, a cycloalkyl group, an alkenyl group, —CO—$R^{11}$, an aryl group and a heteroaryl group (n, $R^9$, $R^{10}$ and $R^{11}$ are as defined above), and $R^{38}$ and $R^{39}$ are each independently a hydrogen atom, an alkyl group, —CO-alkyl or —CO—O-alkyl, and $R^{30}$ and $R^{31}$ are each independently a hydrogen atom, an alkyl group optionally substituted by —OH, —SO$_2$—R$^{40}$, —(CH$_2$)$_x$—CO—R$^{41}$ or

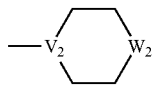

wherein x is 0-3, $R^{40}$ is an alkyl group or —NH$_2$, $R^{41}$ is a hydrogen atom, an alkyl group optionally substituted by —OH, —OH, an alkoxy group, an alkoxyalkyl group or —(CH$_2$)$_s$—N(R$^{42}$)(R$^{43}$)

wherein s is as defined above and $R^{42}$ and $R^{43}$ are each independently a hydrogen atom, an alkyl group, —OH, an alkoxy group, or in combination form

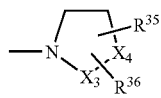

($X_3$, $X_4$, $R^{35}$ and $R^{36}$ are as defined above), $V_2$ is =CH— or =N— and $W_2$ is —C(R$^{44}$)(R$^{45}$)—, —O— or —N(R$^{46}$)— wherein $R^{44}$ and $R^{45}$ are each independently a hydrogen atom, an alkyl group, an alkoxy group, a haloalkyl group, —(CH$_2$)$_r$—OH, —CO—R$^{47}$ or —N(R$^{48}$)(R$^{49}$)

wherein r is as defined above, $R^{47}$ is —OH, an alkoxy group, an alkoxyalkyl group, —N(R$^{50}$)(R$^{51}$)

wherein $R^{50}$ and $R^{51}$ are each independently a hydrogen atom, an alkyl group, —(CH$_2$)$_s$—OH (s is as defined above) or an alkoxyalkyl group, and $R^{48}$ and $R^{49}$ are each independently a hydrogen atom, an alkyl group, —CO-alkyl or —CO—O-alkyl, and $R^{46}$ is a hydrogen atom, —CO—R$^{52}$ or —SO$_2$—R$^{52}$ wherein $R^{52}$ is an alkyl group, an alkoxy group, —NH-alkyl or —N(-alkyl)$_2$ or $R^{30}$ and $R^{31}$ in combination form

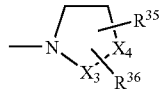

($X_3$, $X_4$, $R^{35}$ and $R^{36}$ are as defined above), or $R^4$ and $R^5$ in combination may form —O-alkylene-O—, a prodrug thereof or a pharmaceutically acceptable salt thereof.

(2) The triazole compound of (1) above, wherein Z is —(CH(R$^{14}$))$_p$— and p is 0, a prodrug thereof or a pharmaceutically acceptable salt thereof.

(3) The triazole compound of (2) above, wherein Y is a $C_{3-8}$ cycloalkyl group, a prodrug thereof or a pharmaceutically acceptable salt thereof.

(4) The triazole compound of (3) above, wherein Ar$^1$ is a phenyl group, a prodrug thereof or a pharmaceutically acceptable salt thereof.

(5) The triazole compound of (4) above, wherein $R^2$ and $R^3$ are each independently a halogen atom or a hydrogen atom, a prodrug thereof or a pharmaceutically acceptable salt thereof.

(6) The triazole compound of any of (1) to (5) above, wherein Ar$^2$ is a phenyl group, $R^4$ is a hydrogen atom, a halogen atom or an alkoxy group and $R^5$ is —CO—N(R$^{28}$)(R$^{29}$), a prodrug thereof or a pharmaceutically acceptable salt thereof.

(7) The triazole compound of (6) above, wherein $R^{28}$ and $R^{29}$ are each independently a hydrogen atom or an alkyl group, a prodrug thereof or a pharmaceutically acceptable salt thereof.

(8) The triazole compound of any of (1) to (5) above, wherein Ar$^2$ is a phenyl group, $R^4$ is a hydrogen atom or a halogen atom and $R^5$ is —N(R$^{30}$)(R$^{31}$) wherein $R^{30}$ is a hydrogen atom and $R^{31}$ is —(CH$_2$)$_x$—CO—R$^{41}$, a prodrug thereof or a pharmaceutically. acceptable salt thereof.

(9) The triazole compound of (8) above, wherein X is 0 and $R^{41}$ is an alkoxy group, a prodrug thereof or a pharmaceutically acceptable salt thereof.

(10) The triazole compound of (8) above, wherein X is 0 and $R^{41}$ is —(CH$_2$)$_s$—N(R$^{42}$)(R$^{43}$), a prodrug thereof or a pharmaceutically acceptable salt thereof.

(11) The triazole compound of (10) above, wherein s is 0, $R^{42}$ is a hydrogen atom and $R^{43}$ is an alkoxy group, a prodrug hereof or a pharmaceutically acceptable salt thereof.

(12) The triazole compound of any of (1) to (5) above, wherein Ar$^2$ is a phenyl group, $R^4$ is a hydrogen atom and $R^5$ is —N(R$^{30}$)(R$^{31}$) wherein $R^{30}$ and $R^{31}$ are joined to form

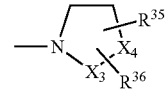

and $X_3$ is —CO—, a prodrug thereof or a pharmaceutically acceptable salt thereof.

(13) The triazole compound of (12) above, wherein $X_4$ is —O—, a prodrug thereof or a pharmaceutically acceptable salt thereof.

(14) The triazole compound of (1) above, which is 3-chloro-4-[4-methyl-5-(1-phenyl-cyclopropyl)-4H-[1,2,4]triazol-3-yl]-benzamide, {3-chloro-4-[4-methyl-5-(1-phenylcyclopropyl)-4H-[1,2,4]triazol-3-yl]benzoyl}morpholine, 3-chloro-N-methyl-4-[4-methyl-5-(1-phenylcyclopropyl)-4H-[1,2,4]triazol-3-yl]benzamide, 3-chloro-N,N-dimethyl-4-[4-methyl-5-(1-phenylcyclopropyl)-4H-[1,2,4]triazol-3-yl]benzamide, 3-chloro-N-(2-hydroxy-ethyl)-4-[4-methyl-5-(1-phenylcyclopropyl)-4H-[1,2,4]triazol-3-yl]benzamide, 3-chloro-N-isopropyl-4-[4-methyl-5-(1-phenylcyclopropyl)$_4$H-[1,2,4]triazol-3-yl]benzamide, {3-chloro-4-[4-methyl-5-(1-phenyl-cyclopropyl)-4H[1,2,4]triazol-3-yl]benzoyl}piperidine, {3-chloro-4-[4-methyl-5-(1-phenylcyclopropyl)-4H[1,2,4]triazol-3-yl]benzoyl}-(4-hydroxy)piperidine, N-carbamoylmethyl-3-chloro-4-[4-methyl-5-(1-phenylcyclopropyl)-4H-[1,2,4]triazol-3-yl]benzamide, 3-chloro-4-[4-methyl-5-(1-phenylcyclopropyl)-4H-[1,2,4]triazol-3-yl]-N-(2,2,2-trifluoro-ethyl)-benzamide, N-(2-acetylamino)ethyl-3-chloro-4-[4-methyl-5-(1-phenyl-cyclopropyl)-4H-[1,2,4]triazol-3-yl]benzamide, 3-chloro-N-(2-methoxy)ethyl-4-[4-methyl-5-(1-phenylcyclopropyl)-4H-[1,2,4]triazol-3-yl]benzamide,
1-acetyl-(4-{3-Chloro-4-[(4-methyl-5-(1-phenylcyclopropyl)-4H-[1,2,4]triazol-3-yl]benzoyl}piperazine,
3-chloro-N-(2-dimethylamino)ethyl-4-[4-methyl-5-(1-phenylcyclopropyl)-4H-[1,2,4]triazol-3-yl]benzamide,
3-chloro-4-[4-methyl-5-(1-phenylcyclopropyl)-4H-[1,2,4]triazol-3-yl]-N-(2-morpholin-4-yl)ethylbenzamide,
4-[4-methyl-5-(1-phenylcyclopropyl)-4H-[1,2,4]triazol-3-yl]-3-methoxybenzamide,
3-chloro-4-{4-methyl-5-[1-(4-fluorophenyl)cyclopropyl]-4H-[1,2,4]triazol-3-yl}benzamide,
3-chloro-N-methyl-4-{4-methyl-5-[1-(4-fluoro-phenyl)cyclopropyl]-4H-[1,2,4]triazol-3-yl}benzamide,
4-[4-isopropyl-5-(1-phenylcyclopropyl)-4H-[1,2,4]triazol-3-yl]benzamide,
4-{5-[1-(4-fluorophenyl)cyclopropyl]-4-isopropyl-4H-[1,2,4]triazol-3-yl}benzamide,
4-chloro-3-{5-[1-(4-fluorophenyl)cyclopropyl]-4-methyl-4H-[1,2,4]triazol-3-yl}benzamide,
4-chloro-3-{5-[1-phenylcyclopropyl]-4-methyl-4H-[1,2,4]triazol-3-yl}benzamide,
3-chloro-4-[4-ethyl-5-(1-phenylcyclopropyl)-4H-[1,2,4]triazol-3-yl]benzamide,
3-chloro-4-{4-ethyl-5-[1-(4-fluorophenyl)cyclopropyl]-4H-[1,2,4]triazol-3-yl}benzamide,
3-[4-isopropyl-5-(1-phenylcyclopropyl)-4H-[1,2,4]triazol-3-yl]benzamide,
3-{5-[1-(4-fluoro-phenyl)cyclopropyl]-4-isopropyl-4H-[1,2,4]triazol-3-yl}benzamide,
N-{3-chloro-4-[4-methyl-5-(1-phenylcycloproppyl)-4H-[1,2,4]triazol-3-yl]phenyl}-1-morpholinecarboxamide,
3-{3-chloro-4-[4-methyl-5-(1-phenylcyclopropyl)-4H-[1,2,4]triazol-3-yl]-phenyl}-1,1-dimethylurea,
{3-chloro-4-[4-methyl-5-(1-phenylcyclopropyl)-4H-[1,2,4]triazol-3-yl]-phenyl}urea,
ethyl N-{3-Chloro-4-[(4-methyl-5-(1-phenyl-cyclopropyl)-4H-[1,2,4]triazol-3-yl]-phenyl}-carbamate,
N-{3-chloro-4-[4-methyl-5-(1-phenylcycloproppyl)-4H-[1,2,4]triazol-3-yl]phenyl}-1-(4-methoxypiperidine)carboxamide,
N-{3-chloro-4-[4-methyl-5-(1-phenylcyclopropyl)-4H-[1,2,4]triazol-3-yl]phenyl}-1-(3-hydroxypiperidine)carboxamide,
N-{3-chloro-4-[4-methyl-5-(1-phenylcycloproppyl)-4H-[1,2,4]triazol-3-yl]phenyl}-1-(4-hydroxypiperidine)carboxamide,
1-{3-chloro-4-[4-methyl-5-(1-phenylcyclopropyl)-4H-[1,2,4]triazol-3-yl]-phenyl}-3-methoxyurea,
1-{3-chloro-4-[4-methyl-5-(1-phenylcyclopropyl)-4H-[1,2,4]triazol-3-yl]phenyl}-3-hydroxy-3-methylurea,
1-(3-chloro-4-{5-[1-(4-fluorophenyl)cyclopropyl]-4-methyl-4H-[1,2,4]triazol-3-yl}phenyl)-3-methoxyurea,
1-(4-{5-[1-(4-fluorophenyl)cyclopropyl]-4-isopropyl-4H-[1,2,4]triazol-3-yl}phenyl)-3-methoxyurea,
1-(3-{5-[1-(4-fluorophenyl)cyclopropyl]-4-isopropyl-4H-[1,2,4]triazol-3-yl}phenyl)-3-methoxyurea,
3-{3-chloro-4-[4-methyl-5-(1-phenylcyclopropyl)-4H-[1,2,4]triazol-3-yl]-phenyl}oxazolidin-2-one,
1-{3-chloro-4-[4-methyl-5-(1-phenylcyclopropyl)-4H-[1,2,4]triazol-3-yl]phenyl}imidazolidin-2-one,
3-(3-chloro-4-{5-[1-(4-fluoro-phenyl)cyclopropyl]-4-methyl-4H-[1,2,4]triazol-3-yl}phenyl)oxazolidin-2-one,
3-(4-{5-[1-(4-fluorophenyl)cyclopropyl]-4-isopropyl-4H-[1,2,4]triazol-3-yl}phenyl)oxazolidin-2-one,
3-(4-chloro-3-{5-[1-(4-fluoro-phenyl)cyclopropyl]-4-methyl-4H-[1,2,4]triazol-3-yl}phenyl)oxazolidin-2-one,
3-(3-{5-[1-(4-fluorophenyl)cyclopropyl]-4-isopropyl-4H-[1,2,4]triazol-3-yl}phenyl)oxazolidin-2-one,
methyl N-(4-chloro-3-{5-[1-(4-fluorophenyl)cyclopropyl]-4-methyl-4H-[1,2,4]triazol-3-yl}phenyl)carbamate, a prodrug thereof or a pharmaceutically acceptable salt thereof.

(15) The triazole compound of (1) above, which is
3-chloro-4-[4-methyl-5-(1-phenyl-cyclopropyl)-4H-[1,2,4]triazol-3-yl]-benzamide,
{3-chloro-4-[4-methyl-5-(1-phenylcyclopropyl)-4H-[1,2,4]triazol-3-yl]benzoyl}morpholine,
3-chloro-N-methyl-4-[4-methyl-5-(1-phenylcyclopropyl)-4H-[1,2,4]triazol-3-yl]benzamide,
3-chloro-N N-dimethyl-4-[4-methyl-5-(1-phenylcyclopropyl)-4H-[1,2,4]triazol-3-yl]benzamide,
3-chloro-N-(2-hydroxy-ethyl)-4-[4-methyl-5-(1-phenylcyclopropyl)-4H-[1,2,4]triazol-3-yl]benzamide,
3-chloro-N-isopropyl-4-[4-methyl-5-(1-phenylcyclopropyl)$_4$H-[1,2,4]triazol-3-yl]benzamide,
{3-chloro-4-[4-methyl-5-(1-phenyl-cyclopropyl)-4H[1,2,4]triazol-3-yl]benzoyl}piperidine,
{3-chloro-4-[4-methyl-5-(1-phenylcyclopropyl)-4H[1,2,4]triazol-3-yl]benzoyl}-(4-hydroxy)piperidine,
N-carbamoylmethyl-3-chloro-4-[4-methyl-5-(1-phenylcyclopropyl)-4H-[1,2,4]triazol-3-yl]benzamide,
3-chloro-4-[4-methyl-5-(1-phenylcyclopropyl)-4H-[1,2,4]triazol-3-yl]-N-(2,2,2-trifluoro-ethyl)-benzamide,
N-(2-acetylamino)ethyl-3-chloro-4-[4-methyl-5-(1-phenylcyclopropyl)-4H-[1,2,4]triazol-3-yl]benzamide,
3-chloro-N-(2-methoxy)ethyl-4-[4-methyl-5-(1-phenylcyclopropyl)-4H-[1,2,4]triazol-3-yl]benzamide,
1-acetyl-(4-{3-Chloro-4-[4-methyl-5-(1-phenylcyclopropyl)-4H-[1,2,4]triazol-3-yl]benzoyl}piperazine,
3-chloro-N-(2-dimethylamino)ethyl-4-[4-methyl-5-(1-phenylcyclopropyl)-4H-[1,2,4]triazol-3-yl]benzamide,
3-chloro-4-[4-methyl-5-(1-phenylcyclopropyl)-4H-[1,2,4]triazol-3-yl]-N-(2-morpholin-4-yl)ethylbenzamide,
4-[4-methyl-5-(1-phenylcyclopropyl)-4H-[1,2,4]triazol-3-yl]-3-methoxybenzamide,
3-chloro-4-{4-methyl-5-[1-(4-fluorophenyl)cyclopropyl]-4H-[1,2,4]triazol-3-yl}benzamide,
3-chloro-N-methyl-4-{4-methyl-5-[(1-(4-fluoro-phenyl)cyclopropyl]-4H-[1,2,4]triazol-3-yl}benzamide,
4-[4-isopropyl-5-(1-phenylcyclopropyl)-4H-[1,2,4]triazol-3-yl]benzamide,
4-{5-[1-(4-fluorophenyl)cyclopropyl]-4-isopropyl-4H-[1,2,4]triazol-3-yl}benzamide,
4-chloro-3-{5-[1-(4-fluorophenyl)cyclopropyl]-4-methyl-4H-[1,2,4]triazol-3-yl}benzamide,
4-chloro-3-{5-[1-phenylcyclopropyl]-4-methyl-4H-[1,2,4]triazol-3-yl}benzamide,
3-chloro-4-[4-ethyl-5-(1-phenylcyclopropyl)-4H-[1,2,4]triazol-3-yl]benzamide,
3-chloro-4-{4-ethyl-5-[1-(4-fluorophenyl)cyclopropyl]-4H-[1,2,4]triazol-3-yl}benzamide,
3-[4-isopropyl-5-(1-phenylcyclopropyl)-4H-[1,2,4]triazol-3-yl]benzamide,
3-{5-[1-(4-fluoro-phenyl)cyclopropyl]-4-isopropyl-4H-[1,2,4]triazol-3-yl}benzamide, a prodrug thereof or a pharmaceutically acceptable salt thereof.
(16) The triazole compound of (1) above, which is
N-{3-chloro-4-[4-methyl-5-(1-phenylcycloproppyl)-4H-[1,2,4]triazol-3-yl]phenyl}-1-morpholinecarboxamide,
3-{3-chloro-4-[4-methyl-5-(1-phenylcyclopropyl)-4H-[1,2,4]triazol-3-yl]-phenyl}-1,1-dimethylurea, {3-chloro-4-[4-methyl-5-(1-phenylcyclopropyl)-4H-[1,2,4]triazol-3-yl]-phenyl}urea, N-{3-chloro-4-[4-methyl-5-(1-phenylcycloproppyl)-4H-[1,2,4]triazol-3-yl]phenyl}-1-(4-methoxypiperidine)carboxamide, N-{3-chloro-4-[4-methyl-5-(1-phenylcycloproppyl)-4H-[1,2,4]triazol-3-yl]phenyl}-1-(3-hydroxypiperidine)carboxamide, N-{3-chloro-4-[4-methyl-5-(1-phenylcycloproppyl)-4H-[1,2,4]triazol-3-yl]phenyl}-1-(4-hydroxypiperidine)carboxamide, 1-{3-chloro-4-[4-methyl-5-(1-phenylcyclopropyl)-4H-[1,2,4]triazol-3-yl]-phenyl}-3-methoxyurea, 1-{3-chloro-4-[4-methyl-5-(1-phenylcyclopropyl)-4H-[1,2,4]triazol-3-yl]phenyl}-3-hydroxy-3-methylurea, 1-(3-chloro-4-{5-[1-(4-fluorophenyl)cyclopropyl]-4-methyl-4H-[1,2,4]triazol-3-yl}phenyl)-3-methoxyurea, 1-(4-{5-[1-(4-fluorophenyl)cyclopropyl]-4-isopropyl-4H-[1,2,4]triazol-3-yl}phenyl)-3-methoxyurea, 1-(3-{5-[1-(4-fluorophenyl)cyclopropyl]-4-isopropyl-4H-[1,2,4]triazol-3-yl}phenyl)-3-methoxyurea, a prodrug thereof or a pharmaceutically acceptable salt thereof.

(17) The triazol compound of (1) above, which is 3-{3-chloro-4-[4-methyl-5-(1-phenylcyclopropyl)-4H-[1,2,4]triazol-3-yl]-phenyl}oxazolidin-2-one, 1-{3-chloro-4-[4-methyl-5-(1-phenylcyclopropyl)-4H-[1,2,4]triazol-3-yl]phenyl}imidazolidin-2-one, 3-(3-chloro-4-{5-[1-(4-fluoro-phenyl)cyclopropyl]-4-methyl-4H-[1,2,4]triazol-3-yl}phenyl)oxazolidin-2-one, 3-(4-{5-[1-(4-fluorophenyl)cyclopropyl]-4-isopropyl-4H-[1,2,4]triazol-3-yl}phenyl)oxazolidin-2-one, 3-(4-chloro-3-{5-[1-(4-fluorophenyl)cyclopropyl]-4-methyl-4H-[1,2,4]triazol-3-yl}phenyl)oxazolidin-2-one, 3-(3-{5-[1-(4-fluorophenyl)cyclopropyl]-4-isopropyl-4H-[1,2,4]triazol-3-yl}phenyl)oxazolidin-2-one, prodrug thereof or a pharmaceutically acceptable salt thereof.

(18) A pharmaceutical composition comprising the triazole compound of any of (1) to (17) above, a prodrug thereof or a pharmaceutically acceptable salt thereof, and a pharmaceutically acceptable carrier.

(19) An HSD1 (11beta-hydroxysteroid dehydrogenase 1) inhibitor comprising the triazole compound of any of (1) to (17) above, a prodrug thereof or a pharmaceutically acceptable salt thereof as an effective component.

(20) A therapeutic or prophylactic drug of diabetes, which comprises the triazole compound of any of (1) to (17) above, a prodrug thereof or a pharmaceutically acceptable salt thereof as an effective component.

(21) A therapeutic or prophylactic drug of obesity, which comprises the triazole compound of any of (1) to (17) above, a prodrug thereof or a pharmaceutically acceptable salt thereof as an effective component.

(22) A therapeutic or prophylactic drug of metabolic syndrome, which comprises the triazole compound of any of (1) to (17) above, a prodrug thereof or a pharmaceutically acceptable salt thereof as an effective component.

(23) A method for the treatment or prophylaxis of diabetes, which comprises administering an effective amount of the triazole compound of any of (1) to (17) above, a prodrug thereof or a pharmaceutically acceptable salt thereof to a mammal.

(24) A method for the treatment or prophylaxis of obesity, which comprises administering an effective amount of the triazole compound of any of (1) to (17) above, a prodrug thereof or a pharmaceutically acceptable salt thereof to a mammal.

(25) A method for the treatment or prophylaxis of metabolic syndrome, which comprises administering an effective amount of the triazole compound of any of (1) to (17) above, a prodrug thereof or a pharmaceutically acceptable salt thereof to a mammal.

(26) The method of (23) above, wherein a different therapeutic drug of diabetes is used in combination.

(27) The method of (26) above, wherein the different therapeutic drug of diabetes is one or more pharmaceutical agents selected from the group consisting of an insulin preparation, a sulfonylurea, an insulin secretagogue, a sulfonamide, a biguanide, an α-glucosidase inhibitor and an insulin sensitizer.

(28) The method of (27) above, wherein the different therapeutic drug of diabetes is one or more pharmaceutical agents selected from the group consisting of insulin, glibenclamide, tolbutamide, glyclopyramide, acetohexamide, glimepiride, tolazamide, gliclazide, nateglinide, glybuzole, metformin hydrochloride, buformine hydrochloride, voglibose, acarbose and pioglitazone hydrochloride.

(29) The method of (24) above, wherein a different therapeutic drug of diabetes is used in combination.

(30) The method of (29) above, wherein the different therapeutic drug of diabetes is one or more pharmaceutical agents selected from the group consisting of an insulin preparation, a sulfonylurea, an insulin secretagogue, a sulfonamide, a biguanide, an α-glucosidase inhibitor and an insulin sensitizer.

(31) The method of (30) above, wherein the different therapeutic drug of diabetes is. one or more pharmaceutical agents selected from the group consisting of insulin, glibenclamide, tolbutamide, glyclopyramide, acetohexamide, glimepiride, tolazamide, gliclazide, nateglinide, glybuzole, metformin hydrochloride, buformine hydrochloride, voglibose, acarbose and pioglitazone hydrochloride.

(32) The method of (25) above, wherein a different therapeutic drug of diabetes is used in combination.

(33) The method of (32) above, wherein the different therapeutic drug of diabetes is one or more pharmaceutical agents selected from the group consisting of an insulin preparation, a sulfonylurea, an insulin secretagogue, a sulfonamide, a biguanide, an α-glucosidase inhibitor and an insulin sensitizer.

(34) The method of (33) above, wherein the different therapeutic drug of diabetes is one or more pharmaceutical agents selected from the group consisting of insulin, glibenclamide, tolbutamide, glyclopyramide, acetohexamide, glimepiride, tolazamide, gliclazide, nateglinide, glybuzole, metformin hydrochloride, buformine hydrochloride, voglibose, so acarbose and pioglitazone hydrochloride.

(35) The method of (23) above, wherein a different therapeutic drug of obesity is used in combination.

(36) The method of (35) above, wherein the different therapeutic drug of obesity is Mazindol.

(37) The method of (24) above, wherein a different therapeutic drug of obesity is used in combination.

(38) The method of (37) above, wherein the different therapeutic drug of obesity is Mazindol.

(39) The method of (25) above, wherein a different therapeutic drug of obesity is used in combination.

(40) The method of (39) above, wherein the different therapeutic drug of obesity is Mazindol.

The triazole compound of the present invention shows a markedly enhanced HSD1 inhibitory activity in vivo, which results from improved metabolic resistance.

DETAILED DESCRIPTION OF THE INVENTION

Respective substituents and moieties used in the present specification are defined in the following.

The "alkyl group" means a straight chain or branched chain alkyl group. Examples thereof include methyl group, ethyl group, propyl group, isopropyl group, butyl group, isobutyl group, sec-butyl group, tert-butyl group, pentyl group, isopentyl group, neopentyl group, tert-pentyl group, 1-ethylpropyl group, hexyl group and the like. It is preferably a straight chain or branched chain alkyl group having 1 to 6, more preferably 1 to 4, carbon atoms.

For $R^1$, preferred are methyl, ethyl, propyl, isopropyl, butyl and isobutyl, and particularly preferred are methyl and isopropyl.

The "cycloalkyl group" means a saturated cyclic alkyl group. Examples thereof include cyclopropyl group, cyclobutyl group, cyclopentyl group, cyclohexyl group, cycloheptyl group, cyclooctyl group and the like. It is preferably a cycloalkyl group having 3 to 8, more preferably 3 to 6, carbon atoms.

For $R^1$, preferred is cyclopropyl.

When $R^1$ is alkyl, cycloalkyl group as a substituent on alkyl is preferably cyclopropyl.

For Y, preferred are cyclopropyl, cyclobutyl and cyclopentyl, and particularly preferred is cyclopropyl.

For $Y_1$, preferred are cyclopropyl, cyclobutyl and cyclopentyl, and particularly preferred is cyclopropyl.

The "heterocycloalkyl group" means a saturated 5- to 7-membered heterocyclic group containing 1 to 3 heteroatoms selected from the group consisting of nitrogen atom, oxygen atom and sulfur atom. Examples thereof include tetrahydrofuryl group, tetrahydrothienyl group, pyrrolidinyl group, pyrazolidinyl group, imidazolidinyl group, oxazolidinyl group, thiazolidinyl group, tetrahydropyranyl group, dioxolanyl group, dioxanyl group, piperidinyl group, piperazinyl group, morpholinyl group and the like.

For Y, preferred is piperidinyl.

For $Y_2$, preferred is dioxolanyl.

The "alkenyl group" means a straight chain or branched chain alkenyl group. Examples thereof include vinyl group, 1-propenyl group, allyl group, 1-methyl-2-propenyl group, 1-butenyl group, 2-butenyl group, 3-butenyl group, 1-pentenyl group, 2-pentenyl group, 1-hexenyl group, 2-hexenyl group and the like. It is preferably a straight chain or branched chain alkenyl group having 2 to 6, more preferably 2 to 4, carbon atoms.

When $R^1$ is alkyl, alkenyl group as a substituent on alkyl is preferably vinyl.

The "aryl group" means an aromatic hydrocarbon group. Examples thereof include phenyl group, naphthyl group, anthryl group and the like. It is preferably a phenyl group or naphthyl group.

For $Ar^1$, $Ar^2$, $Ar^3$ and $Ar^4$, preferred are phenyl and naphthyl, and particularly preferred is phenyl.

The "heteroaryl group" means a monocyclic or fused 5- to 14-membered aromatic heterocyclic group containing 1 to 3 heteroatoms selected from the group consisting of nitrogen atom, oxygen atom and sulfur atom. Examples thereof include furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, indolyl group, isoindolyl group, benzofuranyl group, benzothienyl group, benzoimidazolyl group, benzothiazolyl group, benzoxazolyl group, indolizinyl group, quinolyl group, isoquinolyl group, quinazolinyl group, cinnolinyl group, quinoxalinyl group, phthalazinyl group, acridinyl group, phenazinyl group, naphthyridinyl group and the like. It is preferably a monocyclic or fused 5- to 10-membered aromatic heterocyclic group containing 1 to 3 heteroatoms selected from the group consisting of nitrogen atom, oxygen atom and sulfur atom, which includes furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, indolyl group, isoindolyl group, benzofuranyl group, benzothienyl group, benzoimidazolyl group, benzothiazolyl group, benzooxazolyl group and the like.

For $Ar^1$, preferred are thienyl, pyrrolyl and pyridyl.

For $Ar^2$, preferred are thienyl, pyrrolyl, oxazolyl, isooxazolyl, thiazolyl, imidazolyl, pyrazolyl and pyridyl, and particularly preferred are thienyl and pyridyl.

For $Ar^3$ and $Ar^4$, preferred is pyridyl.

The "halogen atom" means fluorine atom, chlorine atom, bromine atom or iodine atom. It is preferably fluorine atom or chlorine atom.

For $R^2$ and $R^3$, preferred is fluorine atom. In this case, $Ar^1$ is particularly preferably phenyl, where only the 4-position of the phenyl is substituted by fluorine atom.

For $R^4$ and $R^5$, preferred is chlorine atom. In this case, $Ar^2$ is particularly preferably phenyl, where at least the 2-position of the phenyl is substituted by chlorine atom.

The "haloalkyl group" means a haloalkyl group wherein the above-defined "alkyl group" is substituted by the above-defined "halogen atom". Examples thereof include fluoromethyl group, difluoromethyl group, trifluoromethyl group, bromomethyl group, chloromethyl group, 1,2-dichloroethyl group, 2,2-dichloroethyl group, 2,2,2-trifluoroethyl group and the like. It is preferably a straight chain or branched chain haloalkyl group having 1 to 6, more preferably 1 to 4, carbon atoms, particularly preferably a trifluoromethyl group.

The "alkoxy group" means a straight chain or branched chain alkoxy group. Examples thereof include methoxy group, ethoxy group, propoxy group, isopropoxy group, butoxy group, isobutoxy group, tert-butoxy group, pentyloxy group, hexyloxy group and the like. It is preferably a straight chain or branched chain alkoxy group having 1 to 6, more preferably 1 to 4, carbon atoms.

For $R^2$ and $R^3$, preferred is methoxy.

For $R^4$ and $R^5$, preferred are methoxy, ethoxy and isopropoxy.

The "haloalkoxy group" means a haloalkoxy group wherein the above-defined "alkoxy group" is substituted by the above-defined "halogen atom". Examples thereof include fluoromethoxy group, difluoromethoxy group, trifluoromethoxy group, bromomethoxy group, chloromethoxy group, 1,2-dichloroethoxy group, 2,2-dichloroethoxy group, 2,2,2-trifluoroethoxy group and the like. It is preferably a straight chain or branched chain haloalkoxy group having 1 to 6, more preferably 1 to 4, carbon atoms.

The "alkoxyalkyl group" means an alkoxyalkyl group wherein the above-defined "alkyl group" is substituted by the above-defined "alkoxy group". Examples thereof include methoxymethyl group, ethoxymethyl group, propoxymethyl group, isopropoxymethyl group, butoxymethyl group, isobutoxymethyl group, tert-butoxymethyl group, 2-methoxyethyl group, pentyloxymethyl group, hexyloxymethyl group and the like. It is preferably an alkoxyalkyl group wherein the alkyl group is a straight chain or branched chain alkyl group having 1 to 6, more preferably 1 to 4, carbon atoms and the alkoxy group is a straight chain or branched chain alkoxy group having 1 to 6, more preferably 1 to 4, carbon atoms.

For $R^{23}$, $R^{24}$ and $R^{41}$, preferred are methoxymethyl and 2-methoxyethyl.

The "—CO-alkyl" means an alkylcarbonyl group having the above-defined "alkyl group" as the alkyl moiety. Examples thereof include acetyl group, propionyl group, butyryl group, isobutyryl group, valeryl group, isovaleryl group, pivaloyl group, pentanoyl group, hexanoyl group and the like. It is preferably an alkylcarbonyl group wherein the alkyl moiety is a straight chain or branched chain alkyl group having 1 to 6, more preferably 1 to 4, carbon atoms.

For $R^9$, $R^{10}$, $R^{21}$, $R^{22}$, $R^{33}$, $R^{34}$, $R^{38}$, $R^{39}$, $R^{48}$ and $R^{49}$ particularly preferred are acetyl, propionyl, butyryl and isobutyryl.

The "—CO—O-alkyl" means an alkyloxycarbonyl group having the above-defined "alkyl group" as the alkyl moiety. Examples thereof include methyloxycarbonyl group, ethyloxycarbonyl group, propyloxycarbonyl group, isopropyloxycarbonyl group, butyloxycarbonyl group, isobutyloxycarbonyl group, sec-butyloxycarbonyl group, tert-butyloxycarbonyl group, pentyloxycarbonyl group, isopentyloxycarbonyl group, neopentyloxycarbonyl group, tert-pentyloxycarbonyl group, 1-ethylpropyloxycarbonyl group, hexyloxycarbonyl group and the like. It is preferably an alkyloxycarbonyl group wherein the "alkyl moiety" is a straight chain or branched chain alkyl group having 1 to 6, more preferably 1 to 4, carbon atoms.

For $R^{21}$, $R^{22}$, $R^{38}$, $R^{39}$, $R^{48}$ and $R^{49}$, particularly preferred are methyloxycarbonyl, ethyloxycarbonyl, propyloxycarbonyl, isopropyloxycarbonyl and tert-butyloxycarbonyl.

The "—NH-alkyl" means an alkylamino group having the above-defined "alkyl group" as the alkyl moiety. Examples thereof include methylamino group, ethylamino group, propylamino group, isopropylamino group, butylamino group, isobutylamino group, sec-butylamino group, tert-butylamino group, pentylamino group, isopentylamino group, tert-pentylamino group, hexylamino group and the like. It is preferably an alkylamino group wherein the alkyl moiety is a straight chain or branched chain alkyl group having 1 to 6, more preferably 1 to 4, carbon atoms.

For $R^{26}$, $R^{27}$, $R^{32}$ and $R^{52}$, particularly preferred are methylamino, ethylamino, propylamino and isopropylamino.

The "—N(-alkyl)$_2$" means a dialkylamino group having the above-defined "alkyl group" as the alkyl moiety. Examples thereof include dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like. It is preferably a dialkylamino group wherein the alkyl moiety is a straight chain or branched chain alkyl group having 1 to 6, more preferably 1 to 4, carbon atoms.

For $R^{26}$, $R^{27}$, $R^{32}$ and $R^{52}$, particularly preferred are dimethylamino, diethylamino and N-ethyl-N-methylamino.

The "alkyl" moieties of the "alkylamino group" and "dialkylamino group" are optionally substituted by 1 to 5 substituents each independently selected from halogen atom, —CF$_3$, —OH, alkoxy group, haloalkoxy group, —N(R$^9$)(R$^{10}$) (R$^9$ and R$^{10}$ are each independently hydrogen atom, alkyl group or —CO-alkyl), —CN, —NO$_2$, cycloalkyl group, alkenyl group, —CO—R$^{11}$ (R$^{11}$ is —OH, alkoxy group, alkyl group or —N(R$^{12}$)(R$^{13}$) wherein R$^{12}$ and R$^{13}$ are each independently hydrogen atom or alkyl group), aryl group and heteroaryl group. Here, the substituent "aryl group" and "heteroaryl group" are optionally substituted by 1 to 3 substituents each independently selected from halogen atom, haloalkyl group, alkyl group, —(CH$_2$)$_n$—OH (n=0-3), —N(R$^9$)(R$^{10}$) (R$^9$ and R$^{10}$ are independently hydrogen atom, alkyl group or —CO-alkyl), —CN, —NO$_2$, alkoxy group, cycloalkyl group, alkenyl group, —CO—R$^{11}$ (R$^{11}$ is —OH, alkoxy group, alkyl group or —N(R$^{12}$)(R$^{13}$) wherein R$^{12}$ and R$^{13}$ are each independently hydrogen atom or alkyl group), aryl group and heteroaryl group.

The "aryl group" and the "heteroaryl group" for $R^2$, $R^3$, $R^6$, $R^{14}$, $R^{15}$, $R^{16}$, $Ar^3$ and $Ar^4$ are optionally substituted by 1 to 3 substituents each independently selected from halogen atom, haloalkyl group, alkyl group, —(CH$_2$)$_n$—OH (n=0-3), —N(R$^9$)(R$^{10}$) (R$^9$ and R$^{10}$ are each independently hydrogen atom, alkyl group or —CO-alkyl), —CN, —NO$_2$, alkoxy group, cycloalkyl group, alkenyl group, —CO—R$^{11}$ (R$^{11}$ is —OH, alkoxy group, alkyl group or —N(R$^{12}$)(R$^{13}$) wherein R$^{12}$ and R$^{13}$ are each independently hydrogen atom or alkyl group), aryl group and heteroaryl group.

The "cycloalkyl group" and the "heterocycloalkyl group" for Y and Y$_1$ are optionally substituted by 1 to 3 substituents each independently selected from halogen atom, haloalkyl group, alkyl group, —(CH$_2$)$_n$—OH (n=0-3), —N(R$^9$) (R$^{10}$) (R$^9$ and R$^{10}$ are each independently hydrogen atom, alkyl group or —CO-alkyl), —CN, —NO$_2$, alkoxy group, cycloalkyl group, alkenyl group, —CO—R$^{11}$ (R$^{11}$ is —OH, alkoxy group, alkyl group or —N(R$^{12}$)(R$^{13}$) wherein R$^{12}$ and R$^{13}$ are each independently hydrogen atom or alkyl group), aryl group and heteroaryl group.

The "alkyl group" and the "alkoxy group" for $R^4$ and $R^5$, and the "alkoxy group" for $R^{37}$ are optionally substituted by 1 to 5 substituents each independently selected from halogen atom, —CF$_3$, —OH, alkoxy group, haloalkoxy group, —N(R$^9$)(R$^{10}$) (R$^9$ and R$^{10}$ are each independently hydrogen atom, alkyl group or —CO-alkyl), —CN, —NO$_2$, cycloalkyl group, alkenyl group, —CO—R$^{11}$ (R$^{11}$ is —OH, alkoxy group, alkyl group or —N(R$^{12}$) (R$^{13}$) wherein R$^{12}$ and R$^{13}$ are each independently hydrogen atom or alkyl group), aryl group and heteroaryl group. Here, the substituent "aryl group" and "heteroaryl group" are optionally substituted by 1 to 3 substituents each independently selected from halogen atom, haloalkyl group, alkyl group, —(CH$_2$)$_n$—OH (n=0-3), —N(R$^9$) (R$^{10}$) (R$^9$ and R$^{10}$ are independently hydrogen atom, alkyl group or —CO-alkyl), —CN, —NO$_2$, alkoxy group, cycloalkyl group, alkenyl group, —CO—R$^{11}$ (R$^{11}$ is —OH, alkoxy group, alkyl group or —N(R$^{12}$) (R$^{13}$) wherein R$^{12}$ and R$^{13}$ are each independently hydrogen atom or alkyl group), aryl group and heteroaryl group.

The above-mentioned substituents "halogen atom", "haloalkyl group", "alkyl group", "alkoxy group", "haloalkoxy group", "cycloalkyl group", "alkenyl group", "aryl group" and "heteroaryl group" are as defined above.

$R^4$ and $R^5$ in combination may form —O-alkylene-O—. Here, the "alkylene" means a divalent hydrocarbon. Examples thereof include methylene, ethylene, propylene, butylene, pentylene, hexylene and the like. It is preferably an alkylene having 1 to 6, more preferably 1 to 4, carbon atoms, particularly preferably methylene.

In the above-mentioned formulas, Z is preferably —(CH(R$^{14}$))$_p$— and p is 0; Y is preferably a C$_{3-8}$ cycloalkyl group; Ar$^1$ is preferably a phenyl group; Ar$^2$ is preferably a phenyl group; R$^1$ is preferably an alkyl group; R$^2$ is preferably a hydrogen atom; R$^3$ is preferably a halogen atom; R$^4$ is preferably a hydrogen atom, a halogen atom or an alkoxy group; $R^5$ is preferably —CO—N($R^{28}$)($R^{29}$) (wherein $R^{28}$ and $R^{29}$ are preferably each independently a hydrogen atom or an alkyl group) or —N($R^{30}$)($R^{31}$) (wherein $R^{30}$ is preferably a hydrogen atom and $R^{31}$ is preferably —$(CH_2)_x$—CO—$R^{41}$ wherein X is preferably 0 and $R^{41}$ is preferably an alkoxy group, or X is preferably 0 and $R^{41}$ is preferably —$(CH_2)_s$—N($R^{42}$)($R^{43}$) wherein s is preferably 0, $R^{42}$ is preferably a hydrogen atom and $R^{43}$ is preferably an alkoxy group, or $R^{30}$ and $R^{31}$ are preferably joined to form

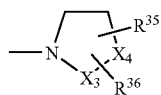

wherein $X_3$ is preferably —CO— and $X_4$ is preferably —O—).

The "pharmaceutically acceptable salt" may be any salt as long as it forms a non-toxic salt with a triazole compound represented by the above-mentioned formula. For example, it can be obtained by reaction with inorganic acids such as hydrochloric acid, sulfuric acid, phosphoric acid, hydrobromic acid and the like; organic acids such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid and the like; inorganic bases such as sodium hydroxide, potassium hydroxide, calcium hydroxide, magnesium hydroxide, ammonium hydroxide and the like; organic bases such as methylamine, diethylamine, triethylamine, triethanolamine, ethylenediamine, tris(hydroxymethyl)methylamine, guanidine, choline, cinchonine, N-methyl-D-glucamine and the like; or amino acids such as lysin, histidine, arginine, alanine and the like. In the present invention, a water-containing form, a hydrate and a solvate of each compound are also encompassed therein.

In addition, the triazole compound represented by the above-mentioned formula includes various isomers. For example, E form and Z form are present as geometric isomers, and when an asymmetric carbon atom is present, enantiomers and diastereomers are present as stereoisomers based thereon. In some cases, a tautomer may be present. Accordingly, the present invention encompasses all these isomers and mixtures thereof.

The present invention also encompasses prodrugs and metabolites of the triazole compound represented by the formula. A "prodrug" is a derivative of the compound of the present invention, which has a chemically or metabolically decomposable group, which, after being administered to a living organism, restores to its original compound form and exhibit its intrinsic efficacy, and which includes complexes and salts free of a covalent bond. For example, ester derivatives known as prodrugs in the field of pharmaceutical agents can be used.

When the compound of the present invention is used as a pharmaceutical preparation, it is generally admixed with a pharmaceutically acceptable carrier, excipient, diluent, extender, disintegrant, stabilizer, preservative, buffer, emulsifier, fragrance, coloring agent, sweetening agent, thickening agent, corrigent, dissolution aids and other additives known per se, such as water, vegetable oil, alcohols such as ethanol, benzyl alcohol and the like, polyethylene glycol, glycerol triacetate, gelatin, lactose, carbohydrates such as starch and the like, magnesium stearate, talc, lanolin, vaseline and the like, and produced in the form of tablet, pill, powder, granule, suppository, injection, eye drop, liquid, capsule, troche, aerosol, elixir, suspension, emulsion, syrup and the like by a conventional method for systemic or local, oral or parenteral administration.

While the dose of the compound of the present invention varies depending on the age, body weight, symptom, disease to be treated, administration method and the like, it is generally 50 mg to 800 mg for an adult per administration, which is given once to several times a day.

The compound of the present invention can be administered to a mammal (human, mouse, rat, rabbit, dog, cat, bovine, pig, monkey etc.) as an HSD1 inhibitor, a prophylactic or therapeutic drug of diabetes, a prophylactic or therapeutic drug of diabetic complication (retinopathy, nephropathy, neuropathy, cardiac infarction and cerebral infarction based on arteriosclerosis etc.), a prophylactic or therapeutic drug of hyperlipemia, a prophylactic or therapeutic drug of obesity, neurodegenerative disease and the like, or a prophylactic or therapeutic drug of diseases mediated by HSD1.

The compound of the present invention can be administered to a mammal concurrently with other therapeutic drug of diabetes or obesity with the aim of the prophylaxis or treatment of diabetes. In the present invention, the "therapeutic drug of diabetes" encompasses therapeutic drugs of diabetic complications. Furthermore, the compound of the present invention can be administered in combination with other therapeutic drugs of diabetes or obesity to a mammal for the prophylaxis or treatment of obesity.

In the case of a combined administration, the compound of the present invention may be administered simultaneously with other therapeutic drugs of diabetes or other therapeutic drugs of obesity (hereinafter to be referred to as a combined pharmaceutical agent) or may be administered at time intervals. In the case of a combined administration, a pharmaceutical composition containing the compound of the present invention and a combined pharmaceutical agent can be administered. Alternatively, a pharmaceutical composition containing the compound of the present invention and a pharmaceutical composition containing a combined pharmaceutical agent may be administered separately. The administration routes of respective pharmaceutical compositions may be the same or different.

In the case of a combined administration, the compound of the present invention may be administered at a dose of 50 mg to 800 mg per administration, which is given once to several times a day. In addition, the compound may be administered at a smaller dose. The combined pharmaceutical agent can be administered at a dose generally employed for the prophylaxis or treatment of diabetes or obesity or at a smaller dose than that.

As other therapeutic drug of diabetes to be used for the combined administration, insulin preparation, sulfonylurea, insulin secretagogue, sulfonamide, biguanide, α-glucosidase inhibitor, insulin sensitizer and the like can be mentioned. For example, insulin, glibenclamide, tolbutamide, glyclopyramide, acetohexamide, glimepiride, tolazamide, gliclazide, nateglinide, glybuzole, metformin hydrochloride, buformine hydrochloride, voglibose, acarbose, pioglitazone hydrochloride and the like can be used for combined administration with the compound of the present invention.

As other therapeutic drug of obesity to be used for the combined administration, for example, mazindol can be mentioned.

Now one example of the production method of the triazole compound of the present invention is described in the following, which does not limit the production method of the compound of the present invention. Even in the absence of description in the production method, efficient production can be afforded by introducing, where necessary, a protecting group into a functional group followed by deprotection in a subsequent step, exchanging the order of respective production methods and steps, and the like. The post-reaction treatment can be applied by a typical method by selecting or combining conventional methods as necessary, such as isolation and purification, crystallization, recrystallization, silica gel chromatography, preparative HPLC and the like.

Production Method 1: In this production method, a triazole compound, wherein the atom linked to the 2- or 5-position (where the substituent Z is linked) of the triazole ring is carbon, is produced, and the method includes any of the following steps.

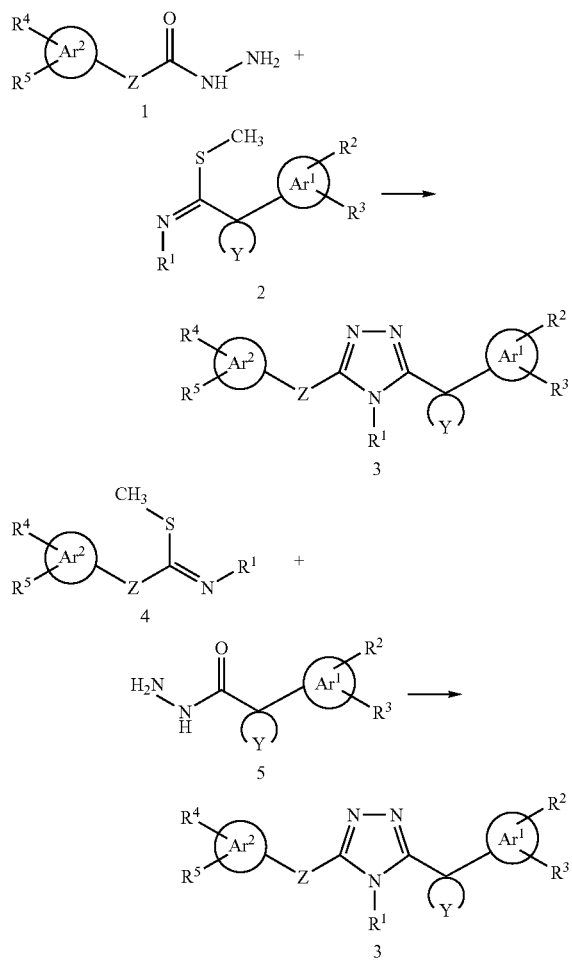

wherein each symbol is as defined above, provided that the atom linked to the 2- or 5-position (where the substituent Z is linked) of the triazole ring of the triazole compound to be formed is carbon.

Acylhydrazide (1) synthesized by a known method and thioimidate (2) synthesized by a known method are reacted in a solvent to give triazole (3). As the solvent, methanol, ethanol, n-propanol, n-butanol, isopropanol, acetonitrile, diethyl ether, tetrahydrofuran (THF), 1,4-dioxane, N,N-dimethylformamide, dimethyl sulfoxide, dichloromethane, 1,2-dichloroethane, chloroform, benzene, chlorobenzene, o-dichlorobenzene, toluene, xylene, pyridine, 2,6-lutidine, 2,4,6-collidine, acetic acid, water, or a mixed solvent thereof can be mentioned. The reaction temperature is preferably 20° C.-250° C.

When acylhydrazide (1) or thioimidate (2) is a salt, the reaction is carried out in the presence of a base such as sodium hydroxide, potassium hydroxide, lithium hydroxide, sodium carbonate, potassium carbonate, sodium bicarbonate, potassium bicarbonate, sodium acetate, potassium acetate, sodium hydride, potassium hydride, triethylamine, N,N-diisopropylethylamine, pyridine and the like.

Alternatively, triazole (3) can be obtained according to a similar method from thioimidate (4) synthesized by a known method and acylhydrazide (5) synthesized by a known method.

Production Method 2: In this production method, a triazole compound, wherein the atom linked to the 2- or 5-position (where the substituent Z is linked) of the triazole ring is nitrogen, is produced, and the method includes the following steps.

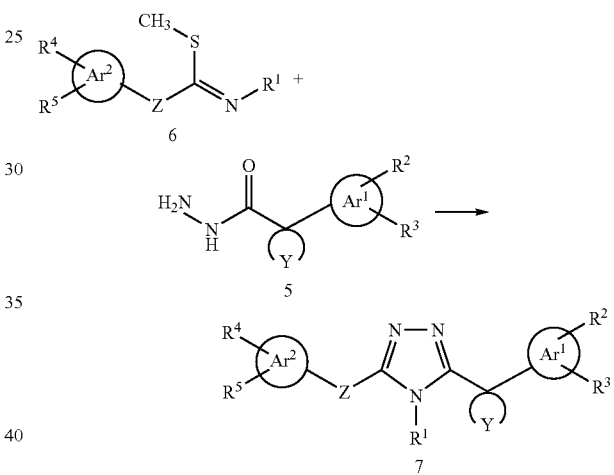

wherein each symbol is as defined above, provided that the atom linked to the 2- or 5-position (where the substituent Z is linked) of the triazole ring of the triazole compound to be formed is nitrogen.

Triazole (7) can be obtained by reacting isothiourea (6) synthesized by a known method with acylhydrazide (5) synthesized by a known method in a solvent. As the solvent, methanol, ethanol, n-propanol, n-butanol, isopropanol, acetonitrile, diethyl ether, tetrahydrofuran (THF), 1,4-dioxane, N,N-dimethylformamide, dimethyl sulfoxide, dichloromethane, 1,2-dichloroethane, chloroform, benzene, chlorobenzene, o-dichlorobenzene, toluene, xylene, pyridine, 2,6-lutidine, 2,4,6-collidine, acetic acid, water, or a mixed solvent thereof can be mentioned. The reaction temperature is preferably 20° C.-250° C.

When isothiourea (6) or acylhydrazide (5) is a salt, the reaction is carried out in the presence of a base such as sodium hydroxide, potassium hydroxide, lithium hydroxide, sodium carbonate, potassium carbonate, sodium bicarbonate, potassium bicarbonate, sodium acetate, potassium acetate, sodium hydride, potassium hydride, triethylamine, N,N-diisopropylethylamine, pyridine and the like.

The production methods described in this specification are examples of the production methods of the compounds of the present invention, and compounds other than the compounds explained above can be produced by combining conventional methods known in the field of organic synthetic chemistry.

EXAMPLES

The triazole compound represented by the formula of the present invention and the production method thereof are explained in detail in the following by referring to Examples, which are not to be construed as limitative.

Example 1-1

Production of 3',5'-dichloro-4-(5-(1-(4-chlorophenyl) cyclopropyl)-4-methyl-4H-[1,2,4]triazol-3-yl)-3,4,5, 6-tetrahydro-2H-[1,4']bipyridyl hydrochloride

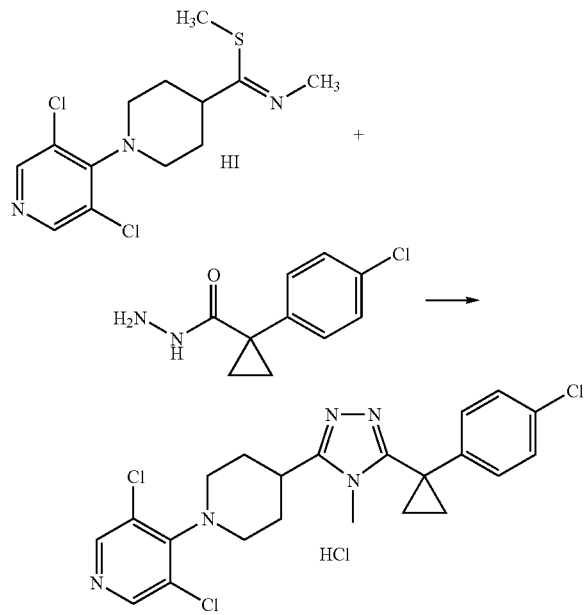

Methyl 3',5'-dichloro-N-methyl-3,4,5,6-tetrahydro-2H-[1, 4']bipyridinyl-4-imidethiocarboxylate hydroiodide (452 mg) and 1-(4-chlorophenyl)-cyclopropane carbohydrazide (178 mg) were suspended in 1,4-dioxane (1.8 ml) and water (0.4 ml), sodium acetate (83 mg) was added and the mixture was heated under reflux overnight. The reaction solution was concentrated and extracted with ethyl acetate. The ethyl acetate layer was washed successively with saturated aqueous sodium hydrogencarbonate solution, water and saturated brine, dried over anhydrous sodium sulfate and concentrated to dryness. The obtained residue was purified by silica gel chromatography (chloroform:acetone=1:1). Thereto was added 4N solution of hydrogen chloride in ethyl acetate (0.16 ml) and the mixture was concentrated to dryness to give the title compound (203 mg).

$^1$H-NMR (400 MHz, DMSO-$d_6$) δ 1.53-1.69 (4H, m), 1.91-2.08 (4H, m), 3.34-3.62 (5H, m), 3.62 (3H, s), 7.22 (2H, d, J=6.0 Hz), 7.38-7.41 (2H, m), 8.47 (2H, s).

Example 2-1

Production of 1-[4-methyl-5-(1-phenylcyclopropyl)- 4H-[1,2,4]triazol-3-yl]-4-phenylpiperidine

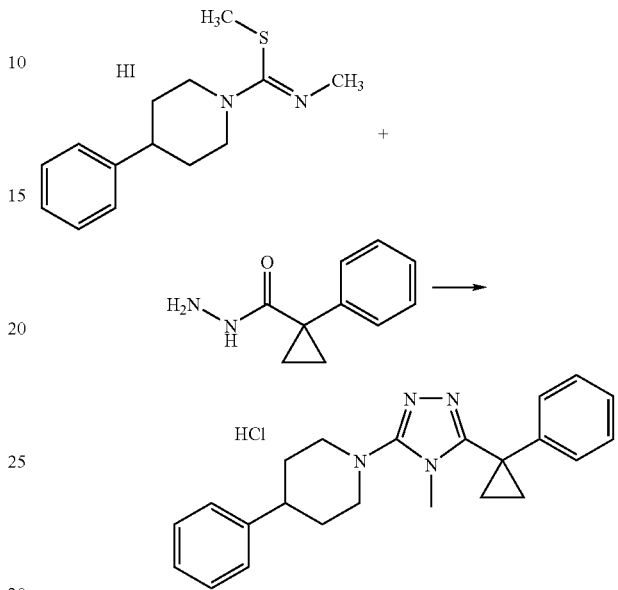

Methyl N-methyl-4-phenylpiperidine-1-imidethiocarboxylate hydroiodide (452 mg) and 1-phenylcyclopropane carbohydrazide (176 mg) were suspended in 1,4-dioxane (2 ml) and water (0.4 ml), sodium acetate (98 mg) was added and the mixture was heated under reflux overnight. The reaction solution was concentrated and extracted with ethyl acetate. The ethyl acetate layer was washed successively with saturated aqueous sodium hydrogencarbonate solution, water and saturated brine, dried over anhydrous sodium sulfate and concentrated to dryness. The obtained residue was purified by silica gel chromatography (chloroform:acetone=1:1). Thereto was added 4N solution of hydrogen chloride in ethyl acetate (0.25 ml) and the mixture was concentrated to dryness. Acetone was added and insoluble solids were collected by filtration and dried to give the title compound (117 mg).

$^1$H-NMR (300 MHz, DMSO-$d_6$) δ 1.50-1.66 (4H, m), 1.76-1.91 (4H, m), 2.70-2.80 (1H, m), 3.19-3.28 (2H, m), 3.43 (3H, s), 3.77 (2H, d, J=12.8 Hz), 7.20-7.39 (10H, m).

Examples 1-2 to 1-161

In the same manner as in Example 1-1, and using other conventional methods as necessary, a triazole compound was produced. The structural formula and property values of each Example compound are shown in the following Table.

Examples 2-2 to 2-99

In the same manner as in Example 2-1, and using other conventional methods as necessary, a triazole compound was produced. The structural formula and property values of each Example compound are shown in the following Table.

| Examples | Molecular Structure | 1H-NMR |
|---|---|---|
| Ex. 1-1 | 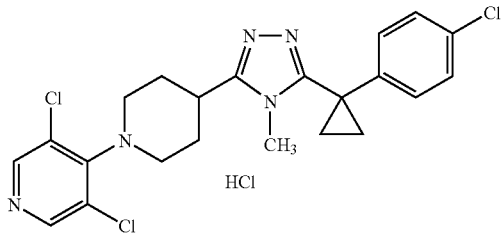 | (400 MHz, DMSO-D6), 1.53-1.69 (4H, m), 1.91-2.08 (4H, m), 3.34-3.62 (5H, m), 3.62 (3H, s), 7.22 (2H, d, J = 6.0 Hz), 7.38-7.41 (2H, m), 8.47 (2H, s) |
| Ex. 1-2 | 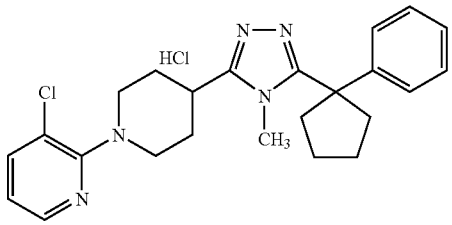 | 400 MHz, DMSO-d6, 1.72-1.82 (4H, m), 1.93-2.12 (4H, m), 2.30-2.39 (2H, m), 2.47-2.58 (2H, m), 2.87-2.98 (2H, m), 3.26-3.38 (4H, m), 3.80-3.87 (2H, m), 6.99-7.04 (1H, m), 7.21-7.26 (2H, m), 7.29-7.42 (3H, m), 7.81-7.86 (1H, m), 8.20-8.23 (1H, m) |
| Ex. 1-3 | 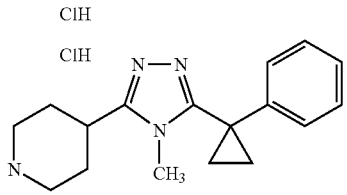 | 400 MHz, DMSO-d6, 1.51-1.69 (4H, m), 1.95-2.14 (4H, m), 2.94-3.06 (2H, m), 3.31-3.40 (3H, m), 3.56 (3H, s), 7.15-7.36 (5H, m), 9.14-9.37 (2H, br) |
| Ex. 1-4 | 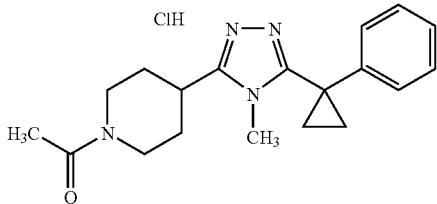 | 300 MHz, DMSO-d6, 1.50-1.77 (5H, m), 1.93-2.05 (4H, m), 2.63-2.73 (1H, m), 3.12-3.20 (1H, m), 3.27-3.33 (1H, m), 3.58 (3H, s), 3.89-3.96 (1H, m), 4.40-4.47 (1H, m), 7.13-7.37 (5H, m) |
| Ex. 1-5 | 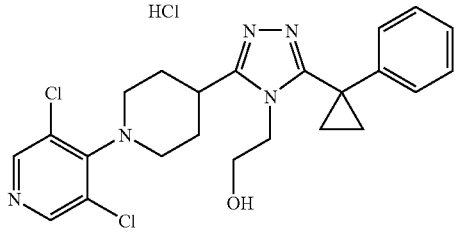 | (DMSO-D6) 1.51-1.78 (4H, m), 1.88-2.14 (4H, m), 3.28-3.54 (7H, m) 4.14 (2H, t, J = 5.5 Hz), 7.22-7.42 (5H, m), 8.47 (2H, s) |
| Ex. 1-6 | 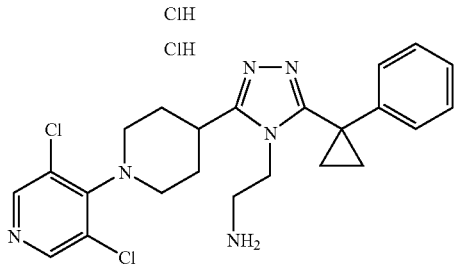 | (DMSO-D6) 1.51-1.79 (4H, m), 1.92-2.16 (4H, m), 2.27-2.90 (2H, m), 3.36-3.65 (5H, m), 4.32-4.48 (2H, m), 7.22-7.42 (5H, m), 8.40-8.61 (4H, m) |

-continued
| Examples | Molecular Structure | 1H-NMR |
|---|---|---|
| Ex. 1-7 | 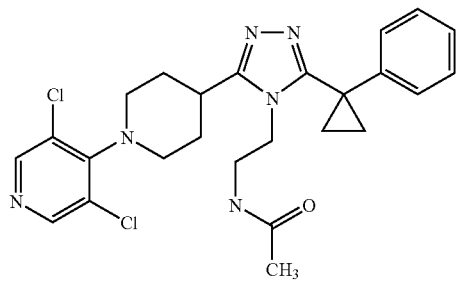 | (DMSO-D6) 1.30-1.40 (2H, m), 1.50-1.58 (2H, m), 1.77 (3H, s), 1.82-2.01 (4H, m), 2.92-3.13 (3H, m), 3.26-3.48 (4H, m), 3.69-3.80 (2H, m), 7.04-7.37 (5H, m), 7.98-8.07 (1H, m), 8.43 (2H, s) |
| Ex. 1-8 | 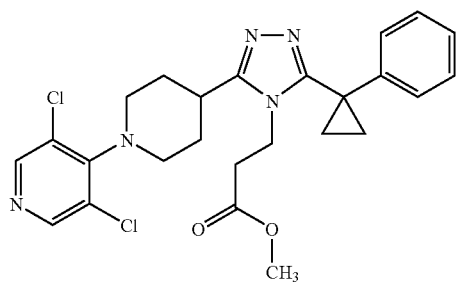 | (CDCl3) 1.40-1.47 (2H, m), 1.60-1.65 (2H, m), 1.84-1.97 (2H, m), 2.18-2.36 (4H, m), 2.77-2.84 (1H, m), 3.32-3.56 (4H, m), 3.65 (3H, s), 3.98-4.08 (2H, m), 7.20-7.32 (5H, m), 8.32 (2H, s) |
| Ex. 1-9 | 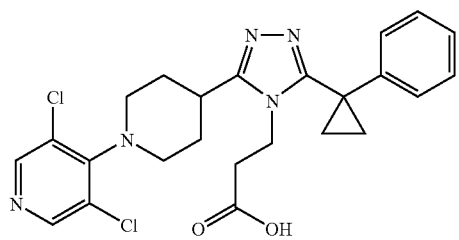 | (DMSO-D6) 1.33-1.57 (4H, m), 1.81-2.02 (4H, m), 2.26 (2H, t, J = 7.8 Hz), 2.98-3.10 (1H, m), 3.20-3.43 (4H, m), 3.95 (2H, t, J = 7.8 Hz), 7.04-7.37 (5H, m), 8.44 (2H, s) |
| Ex. 1-10 | 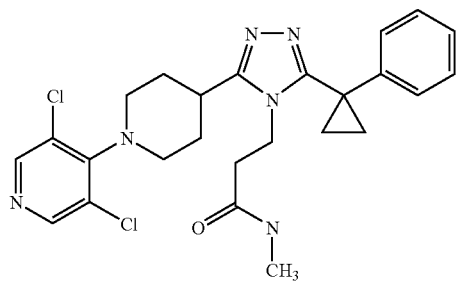 | (DMSO-D6) 1.33-1.53 (4H, m), 1.82-2.02 (4H, m), 2.26 (2H, t, J = 8.1 Hz), 2.54 (3H, d, J = 4.4 Hz), 2.95-3.05 (1H, m), 3.28-3.44 (4H, m), 3.97 (2H, t, J = 8.1 Hz), 7.04-7.32 (5H, m), 7.77-7.83 (1H, m), 8.43 (2H, s) |
| Ex. 1-11 | 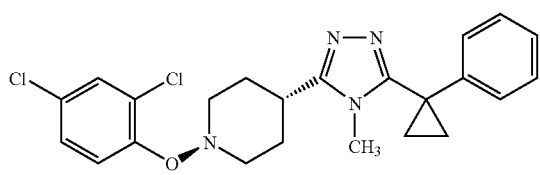 | (DMSO-D6) 1.36-1.47 (4H, m), 1.50-1.61 (2H, m), 1.62-1.80 (2H, m), 2.78-2.89 (1H, m), 3.39 (3H, s), 4.44-4.57 (1H, m), 6.97-7.03 (2H, m), 7.16-7.40 (5H, m), 7.52-7.59 (1H, m) |
| Ex. 1-12 | 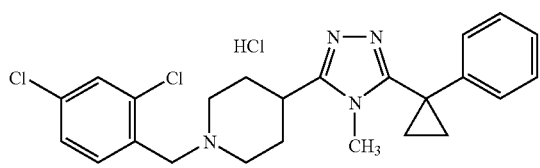 | 400 MHz, DMSO-d6, 1.50-1.69 (4H, m), 2.08-2.37 (4H, m), 3.11-3.38 (4H, m), 3.46-3.57 (4H, m), 4.44 (2H, s), 7.15-7.37 (5H, m), 7.57-7.62 (1H, m), 7.77-7.81 (1H, m), 8.01-8.07 (1H, m), 11.6 (1H, brs) |

-continued
| Examples | Molecular Structure | 1H-NMR |
|---|---|---|
| Ex. 1-13 | 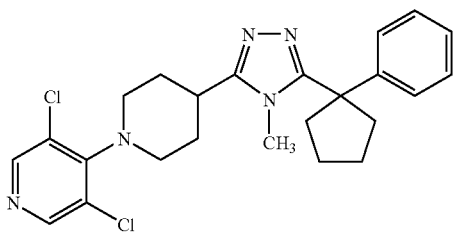 | 400 MHz, DMSO-d6, 1.64-1.76 (4H, m), 1.83-1.93 (4H, m), 2.12-2.23 (2H, m), 2.42-2.55 (2H, m), 2.90-2.99 (1H, m), 3.08 (3H, s), 3.25-3.46 (4H, m), 7.08-7.15 (2H, m), 7.19-7.26 (1H, m), 7.28-7.36 (2H, m), 8.43 (2H, s) |
| Ex. 1-14 | 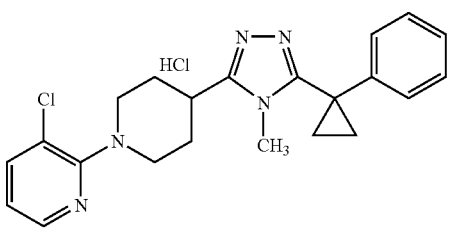 | 400 MHz, DMSO-d6, 1.54-1.76 (4H, m), 1.88-2.16 (5H, m), 2.89-3.03 (2H, m), 3.26-3.41 (1H, m), 3.64 (3H, s), 3.77-3.91 (2H, m), 6.98-7.05 (1H, m), 7.16-7.41 (5H, m), 7.80-7.89 (1H, m), 8.20-8.27 (1H, m) |
| Ex. 1-15 | 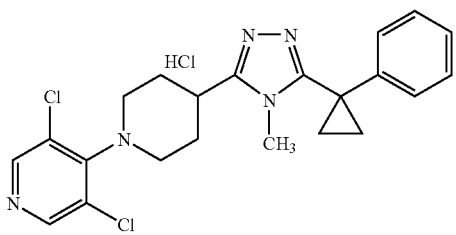 | 400 MHz, DMSO-d6, 1.50-1.72 (4H, m), 1.86-2.12 (5H, m), 3.27-3.49 (4H, m), 3.62 (3H, s), 7.14-7.39 (5H, m), 8.47 (2H, s) |
| Ex. 1-16 | 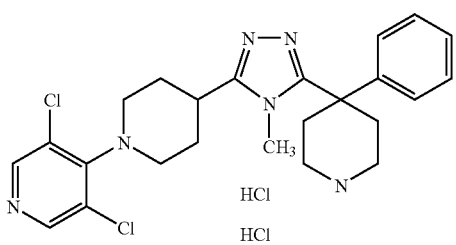 | (400 MHz, DMSO-D6), 1.91-2.05 (4H, m), 2.42-2.54 (2H, m), 2.62-2.72 (2H, m), 3.07-3.31 (4H, m), 3.23 (3H, s), 3.32-3.46 (5H, m), 7.20-7.54 (5H, m), 8.47 (2H, s), 9.15-9.37 (2H, m) |
| Ex. 1-17 | 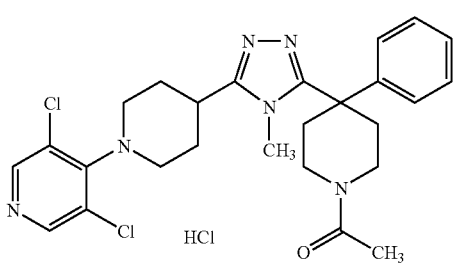 | (400 MHz, DMSO-D6), 1.94-2.07 (4H, m), 2.02 (3H, s), 2.09-2.30 (2H, m), 2.44-2.53 (2H, m), 3.30 (3H, s), 3.31-3.52 (5H, m), 4.06-4.14 (4H, m), 7.23-7.48 (5H, m), 8.48 (2H, s) |
| Ex. 1-18 | 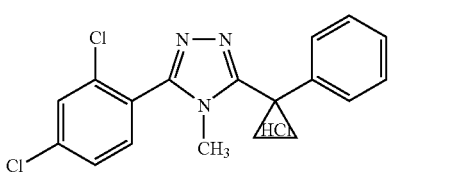 | (300 MHz, DMSO-D6), 1.50-1.70 (4H, m), 3.29 (3H, s), 7.09-7.17 (2H, m), 7.22-7.29 (1H, m), 7.31-7.38 (2H, m), 7.65 (2H, m), 7.91-7.95 (1H, m) |

-continued

| Examples | Molecular Structure | 1H-NMR |
|---|---|---|
| Ex. 1-19 | 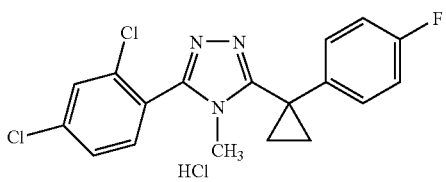 | (300 MHz, DMSO-D6), 1.44-1.64 (4H, m), 3.27 (3H, s), 7.17 (2H, s), 7.19 (2H, s), 7.66 (2H, m), 7.91 (1H, m) |
| Ex. 1-20 | 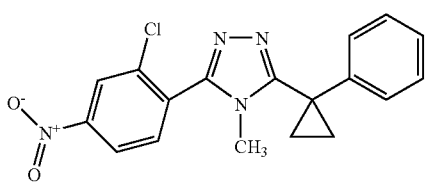 | (300 MHz, CDCl3), 1.49-1.53 (2H, m), 1.67-1.71 (2H, m), 3.27 (3H, s), 7.15-7.18 (2H, m), 7.21-7.26 (1H, m), 7.30-7.35 (2H, m), 7.77 (1H, d, J = 8.4 Hz), 8.26 (1H, dd, J = 2.3, 8.4 Hz), 8.38 (1H, d, J = 2.3 Hz) |
| Ex. 1-21 | 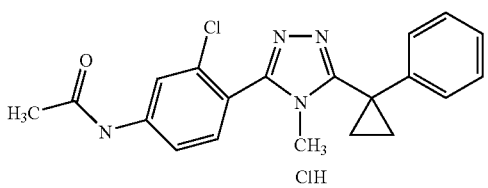 | (300 MHz, DMSO-D6), 1.53-1.57 (2H, m), 1.65-1.69 (2H, m), 2.11 (3H, s), 3.30 (3H, s), 7.13-7.15 (2H, m), 7.24-7.29 (1H, m), 7.33-7.38 (2H, m), 7.58 (1H, d, J = 8.4 Hz), 7.68 (1H, dd, J = 2.2, 8.4 Hz), 8.06 (1H, d, J = 2.2 Hz) |
| Ex. 1-22 | 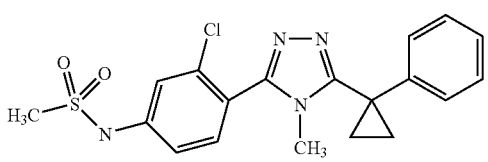 | (300 MHz, DMSO-D6) 1.44-1.57 (4H, m), 3.15 (3H, s), 3.19 (3H, s), 7.03-7.07 (2H, m), 7.19-7.35 (4H, m), 7.40 (1H, d, J = 2.1 Hz), 7.54 (1H, d, J = 8.4 Hz), 10.35 (1H, s) |
| Ex. 1-23 | 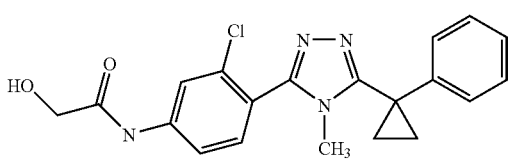 | (300 MHz, DMSO-D6) 1.44-3.57 ((4H, m), 3.19 (3H, s), 4.04 (2H, s), 5.75 (1H, brs), 7.05 (2H, d, J = 7.8 Hz), 7.19-7.35 (3H, m), 7.51 (1H, d, J = 8.7 Hz), 7.82 (1H, dd, J = 1.8, 8.9 Hz), 8.13 (1H, d, J = 1.8 Hz) 10.12 (1H, s) |
| Ex. 1-24 | 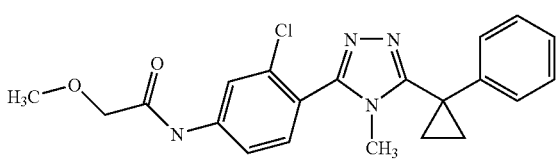 | (300 MHz, DMSO-D6) 1.44-1.57 (4H, m), 3.19 (3H, s), 3.39 (3H, s), 4.06 (2H, s), 7.05 (2H, d, J = 7.2 Hz), 7.19-7.35 (3H, m), 7.52 (1H, d, J = 8.4 Hz), 7.77 (1H, dd, J = 1.8, 8.4 Hz), 8.08 (1H, d, J = 1.8 Hz), 10.19 (1H, s) |
| Ex. 1-25 | 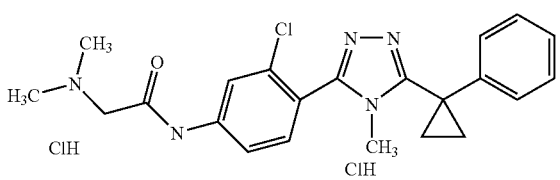 | (300 MHz, DMSO-D6) 1.53-1.70 (4H, m), 2.89-2.90 (6H, m), 3.30 (3H, s), 4.27 (2H, brs), 7.13-7.17 (2H, m), 7.24-7.37 (3H, m), 8.11 (1H, d, J = 1.8 Hz), 10.24 (1H, brs), 11.84 (1H, s) |
| Ex. 1-26 | 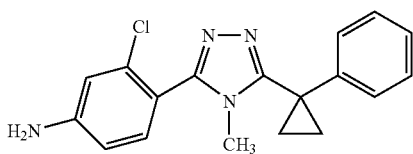 | (300 MHz, CDCl3), 1.43-1.47 (2H, m), 1.65-1.68 (2H, m), 3.23 (3H, s), 3.99 (2H, brs), 6.62 (1H, dd, J = 2.2, 8.3 Hz), 6.75 (1H, d, J = 2.2 Hz), 7.12-7.15 (2H, m), 7.18-7.25 (1H, m), 7.26 (1H, d, J = 8.3 Hz), 7.27-7.32 (2H, m) |

-continued

| Examples | Molecular Structure | 1H-NMR |
|---|---|---|
| Ex. 1-27 | 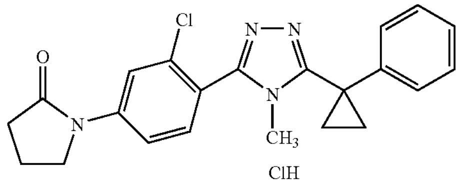 | (300 MHz, DMSO-D6), 1.52-1.56 (2H, m), 1.64-1.68 (2H, m), 2.09 (2H, tt, J = 6.9, 7.8 Hz), 2.56 (2H, t, J = 7.8 Hz), 3.29 (3H, s), 3.90 (2H, t, J = 6.9 Hz),7.12(-7.15 (2H, m), 7.24-7.29 (1H, m), 7.33-7.38 (2H, m), 7.65 (1H, d, J = 8.6 Hz), 7.80 (1H, dd, J = 2.2, 8.6 Hz), 8.12 (1H, d, J = 2.2 Hz) |
| Ex. 1-28 | 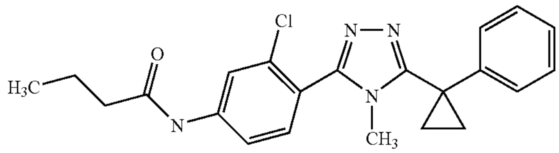 | (300 MHz, DMSO-D6), 0.92 (3H, t, J = 7.5 Hz), 1.54-1.70 (6H, m), 2.36 (2H, t, J = 7.4 Hz), 3.31 (3H, s), 7.13-7.17 (2H, m), 7.24-7.39 (3H, m), 7.56 (1H, d, J = 8.4 Hz), 7.71 (1H, dd, J = 2.1, 8.4 Hz), 8.09 (1H, d, J = 1.8 Hz), 10.55 (1H, s) |
| Ex. 1-29 | 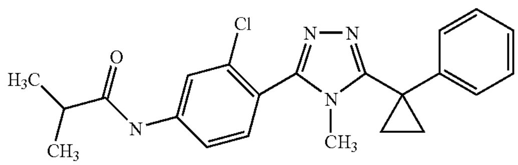 | (300 MHz, DMSO-D6) 1.12 (6H, d, J = 6.9 Hz), 1.43-1.58 (4H, m), 2.57-2.67 (1H, m), 3.18 (3H, s), 7.05 (2H, m), 7.19-7.35 (3H, m), 7.49 (1H, d, J = 8.4 Hz), 7.63 (1H, dd, J = 2.3, 8.6 Hz), 8.04 (1H, d, J = 1.8 Hz), 10.23 (1H, s) |
| Ex. 1-30 | 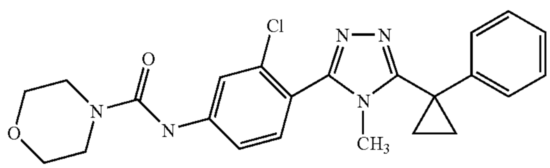 | (300 MHz, DMSO-D6) 1.45-1.60 (4H, m), 3.18 (3H, s), 3.43-3.47 (4H, m), 3.60-3.64 (4H, m), 7.03-7.06 (2H, m), 7.19-7.35 (3H, m), 7.42 (1H, d, J = 8.4 Hz), 7.57 (1H, dd, J = 1.8, 8.4 Hz), 7.86 (1H, d, J = 1.8 Hz) ,8.94 (1H, s) |
| Ex. 1-31 | 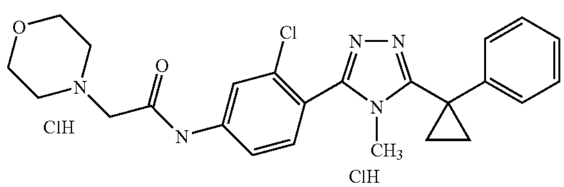 | (300 MHz, DMSO-D6) 1.53-1.66 (4H, m), 3.30 (3H, s), 3.47 (4H, br), 3.93 (4H, br), 4.32 (2H, s), 7.13 (2H, d, J = 7.2 Hz), 7.23-7.38 (3H, m), 7.65 (1H, d, J = 8.7 Hz), 7.76 (1H, dd, J = 2.1, 8.7 Hz), 8.09 (1H, d, J = 2.1 Hz), 11.74 (1H, s) |
| Ex. 1-32 | 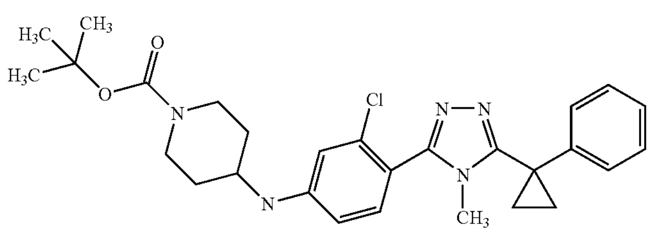 | (300 MHz, DMSO-D6) 1.15-1.30 (2H, m), 1.41 (9H, s), 1.42-1.55 (4H, m), 1.87-1.91 (2H, m), 2.93 (2H, m), 3.16 (3H, s), 3.49 (1H, m), 3.85-3.90 (2H, m), 6.29 (1H, d, J = 8.1 Hz), 6.66 (1H, dd, J = 2.1, 8.4 Hz), 6.77 (1H, d, J = 2.1 Hz), 7.02-7.05 (2H, m), 7.17-7.34 (4H, m) |
| Ex. 1-33 | 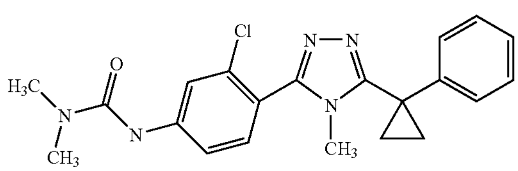 | (300 MHz, DMSO-D6) 1.40-1.60 (4H, m), 2.95 (6H, s), 3.18 (3H, s), 7.05 (2H, d, J = 7.5 Hz), 7.19-7.35 (3H, m), 7.40 (1H, d, J = 8.4 Hz), 7.60 (1H, dd, J = 1.8, 8.4 Hz), 7.88 (1H, J = 1.8 Hz), 8.69 (1H, s) |
| Ex. 1-34 | 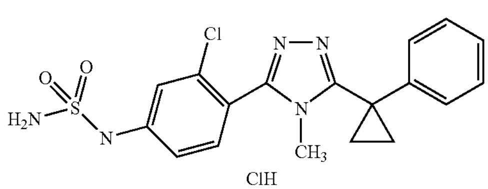 | (300 Mhz, DMSO-D6) 1.53-1.71 (4H, m), 3.32 (3H, s), 7.12-7.59 (10H, m), 10.31 (1H, s) |

-continued

| Examples | Molecular Structure | 1H-NMR |
| --- | --- | --- |
| Ex. 1-35 | 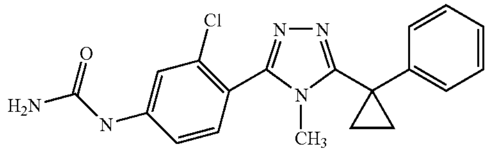 | (300 MHz, DMSO-D6) 1.40-1.60 (4H, m), 3.18 (3H, s), 6.09 (2H, br.s), 7.03-7.06 (2H, m), 7.19-7.41 (5H, m), 7.89 (1H, br.s), 9.02 (1H, br.s) |
| Ex. 1-36 | 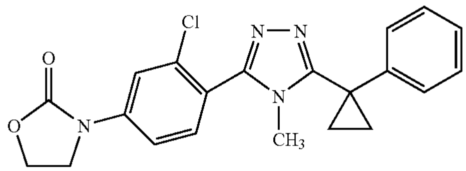 | (300 MHz, DMSO-D6) 1.44-1.58 (4H, m), 3.19 (3H, s), 4.10-4.16 (2H, m), 4.46-4.51 (2H, m), 7.06 (2H, m), 7.19-7.35 (3H, m), 7.60 (1H, d, J = 8.4 Hz), 7.67 (1H, dd, J = 2.1, 8.4 Hz), 7.92 (1H, d, J = 2.1 Hz) |
| Ex. 1-37 | 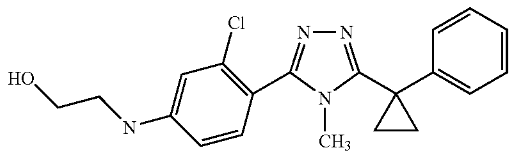 | (300 MHz, DMSO-D6) 1.41-1.55 (4H, m), 3.12-3.18 (2H, m), 3.16 (3H, s), 3.53-3.59 (2H, m), 4.74 (1H, t, J = 5.4 Hz), 6.36 (1H, t, J = 5.7 Hz), 6.66 (1H, dd, J = 2.1, 8.7 Hz), 6.76 (1H, J = 2.1 Hz) ,7.03 (2H, d, 7.5 Hz), 7.17-7.34 (4H, m) |
| Ex. 1-38 | 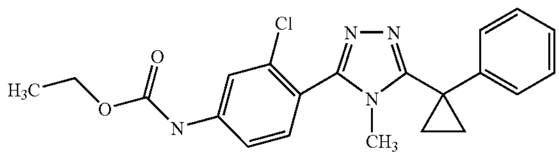 | (300 MHz, DMSO-D6) 1.26 (3H, t, J = 6.9 Hz), 1.43-1.57 (4H, m), 3.18 (3H, s), 4.17 (2H, q, J = 6.9 Hz), 7.05 (2H, m), 7.19-7.34 (3H, m), 7.47 (1H, d, J = 8.4 Hz), 7.54 (1H, dd, J = 1.8, 8.4 Hz), 7.89 (1H, d, J = 1.8 Hz), 10.09 (1H, s) |
| Ex. 1-39 | 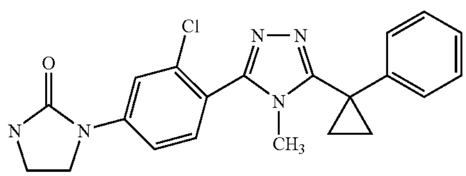 | (300 MHz, DMSO-D6) 1.43-1.58 (4H, m), 3.18 (3H, s), 3.41-3.47 (2H, m), 3.88-3.94 (2H, m), 7.06 (2H, m), 7.19-7.35 (4H, m), 7.49 (1H, d, J = 8.4 Hz), 7.58 (1H, dd, J = 2.4, 8.4 Hz), 7.97 (1H, d, J = 2.4 Hz) |
| Ex. 1-40 | 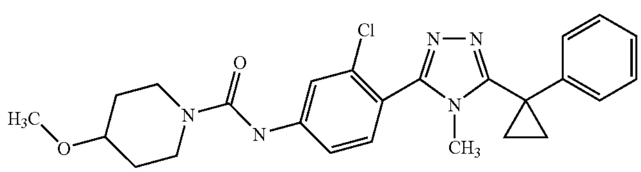 | (300 MHz, DMSO-D6) 1.40-1.57 (6H, m), 1.83-1.90 (2H, m), 3.13-3.21 (5H, m), 3.27 (3H, s), 3.40 (1H, m), 3.74-3.79 (2H, m), 7.05 (2H, m), 7.19-7.35 (3H, m), 7.40 (1H, d, J = 8.4 Hz), 7.57 (1H, dd, J = 1.8, 8.4 Hz), 7.86 (1H, d, J = 1.8 Hz) ,8.92 (1H, s) |
| Ex. 1-41 | 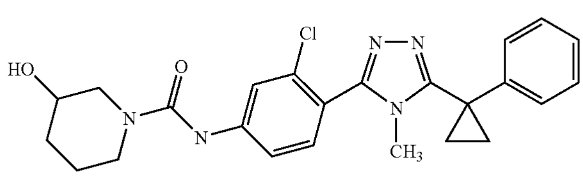 | (300 MHz, DMSO-D6) 1.35-1.57 (6H, m), 1. 70 (1H, m), 1.87 (1H, m), 2. 2.81 (1H, dd, J = 8.4, 12.9 Hz), 3. 2.99 (1H, m), 3.18 (3H, s), 3.48 (1H, m, 4. 3.74 (1H, m), 3.91 (1H, m), 5. 3.85 (1H, d, 4.2 Hz), 7.05 (2H, m), 6. 7.19-7.35 (3H, m), 7. 7.40 (1H, d, J = 8.4 Hz), 8. 7.57 (1H, dd, J = 2.1, 8.4 Hz), 9. 7.86 (1H, J = 2.1 Hz), 8.87 (1H, s) |
| Ex. 1-42 | 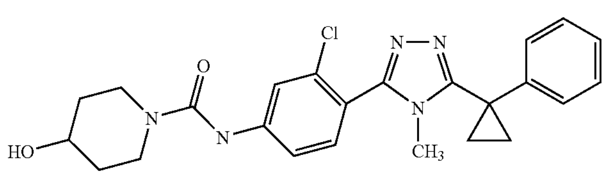 | (300 MHz, DMSO-D6) 1.32-1.57 (6H, m), 1.65-1.80 (2H, m), 3.10-3.18 (2H, m), 3.18 (3H, s), 3.68 (1H, m), 3.80-3.85 (2H, m), 4.27 (1H, d, J = 4.5 Hz), 7.05 (2H, m), 7.19-7.35 (3H, m), 7.40 (1H, d, J = 8.7 Hz), 7.56 (1H, dd, J = 2.1, 8.4 Hz), 7.87 (1H, d, J = 1.8 Hz), 8.92 (1H, s) |

| Examples | Molecular Structure | 1H-NMR |
|---|---|---|
| Ex. 1-43 | 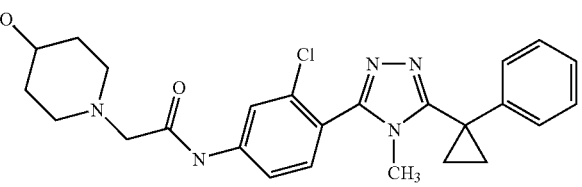 | (300 MHz, DMSO-D6) 1.46-1.55 (6H, m), 1.72-1.80 (2H, m), 2.21-2.28 (2H, m), 2.72-2.76 (2H, m), 3.13 (2H, s), 3.19 (3H, s), 3.49 (1H, m), 4.56 (1H, d, J = 4.2 Hz), 7.05 (2H, d, J = 7.5 Hz), 7.19-7.35 (3H, m), 7.50 (1H, d, J = 8.4 Hz), 7.74 (1H, J = 1.8, 8.4 Hz), 8.07 (1H, d, J = 1.5 Hz), 10.07 (1H, s) |
| Ex. 1-44 | 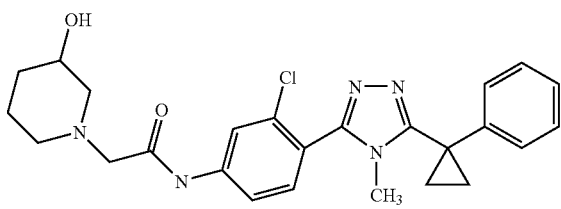 | (300 MHz, DMSO-D6) 1.17-1.21 (1H, m), 1.43-1.58 (5H, m), 1.69-1.73 (2H, m), 2.06-2.25 (2H, m), 2.57-2.61 (1H, m), 2.73-2.77 (1H, m), 3.15 (2H, s), 3.19 (3H, s), 3.62 (1H, m), 4.70 (1H, d, J = 5.4 Hz), 7.06 (2H, m), 7.19-7.35 (3H, m), 7.52 (1H, d, J = 8.4 Hz), 7.75 (1H, dd, J = 1.8, 8.4 Hz), 8.05 (1H, d, J = 1.8 Hz), 10.08 (1H, s) |
| Ex. 1-45 | 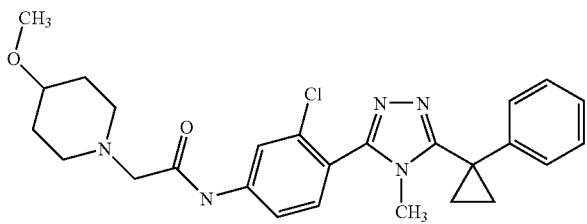 | (300 MHz, DMSO-D6) 1.43-1.59 (6H, m), 1.84-1.90 (2H, m), 2.25-2.32 (2H, m), 2.71-2.75 (2H, m), 3.14 (2H, s), 3.19 (3H, s), 3.21 (1H, br), 3.23 (3H, s), 7.05 (2H, m), 7.19-7.35 (3H, m), 7.50 (1H, d, J = 8.4 Hz), 7.76 (1H, dd, J = 1.8, 8.4 Hz), 8.07 (1H, d, J = 2.1 Hz), 10.07 (1H, s) |
| Ex. 1-46 | 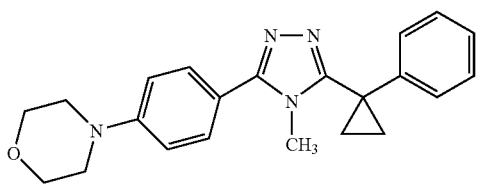 | (DMSO-D6) 1.41-1.57 (4H, m), 3.16-3.23 (4H, m), 3.43 (3H, s), 3.70-3.79 (4H, m), 7.00-7.12 (4H, m), 7.17-7.7.32 (3H, m) 7.51-7.79 (2H, m) |
| Ex. 1-47 | 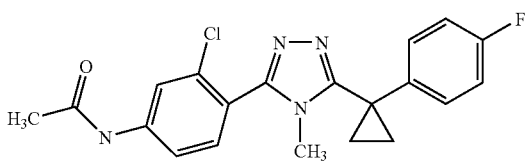 | (400 MHz, CDCl3) 1.40-1.50 (2H, m), 1.60-1.74 (2H, m), 2.22 (3H, s), 3.24 (3H, s), 6.98-7.29 (6H, m), 7.70 (1H, s), 9.24 (1H, d, J = 5.6 Hz) |
| Ex. 1-48 | 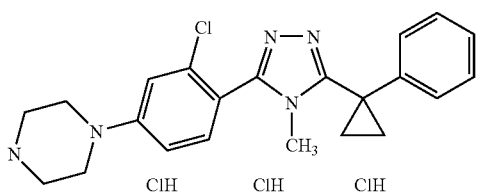 | (300 MHz, DMSO-D6) 1.48-1.67 (4H, m), 3.13-3.22 (4H, m), 3.44-3.63 (7H, m), 4.81 (2H, br.s), 7.13-7.52 (8H, m), 9.35 (2H, br.s) |
| Ex. 1-49 | 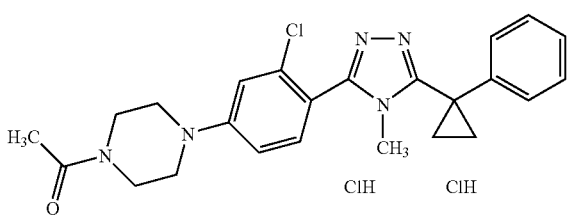 | (400 MHz, DMSO-D6) 1.50-1.73 (4H, m), 2.04 (3H, s), 3.23-3.44 (7H, m), 3.55-3.67 (4H, m), 7.01-7.49 (8H, m) |

-continued
| Examples | Molecular Structure | 1H-NMR |
|---|---|---|
| Ex. 1-50 | 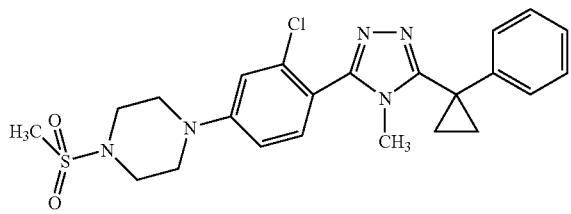 | (400 MHz, DMSO-D6) 1.41-1.59 (4H, m), 2.88 (3H, s), 3.24 (3H, s), 3.20-3.33 (4H, m), 3.40-3.51 (4H, m), 7.00-7.41 (8H, m) |
| Ex. 1-51 | 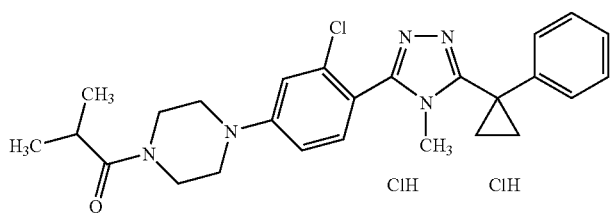 | (300 MHz, DMSO-D6) 1.02 (12H, d, J = 6.6 Hz), 1.52-1.73 (4H, m), 2.92 (1H, septet, J = 6.6 Hz), 3.29-3.48 (7H, m), 3.55-3.76 (4H, m), 7.06-7.59 (8H, m) |
| Ex. 1-52 | 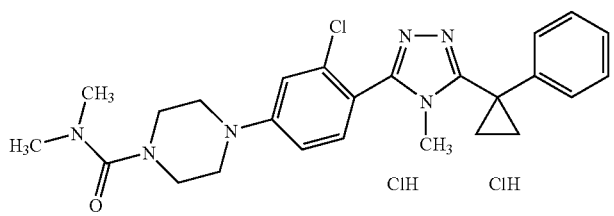 | (300 MHz, DMSO-D6) 1.50-1.71 (4H, m), 2.78 (6H, s), 3.19-3.40 (7H, m), 7.02-7.48 (8H, m) |
| Ex. 1-53 | 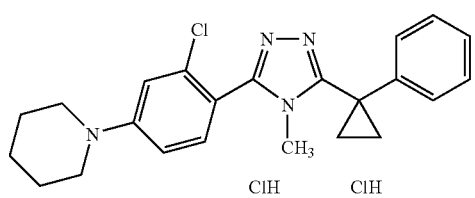 | (300 MHz, DMSO-d6) 1.60 (5H, m), 1.70 (2H, m), 3.28-3.38 (7H, m), 7.08 (1H, dd, J = 8.8, 2.2 Hz), 7.17-7.19 (3H, m), 7.29 (1H, t, J = 7.4 Hz), 7.38 (2H, t, J = 7.4 Hz), 7.46 (1H, d, J = 8.8 Hz) |
| Ex. 1-54 | 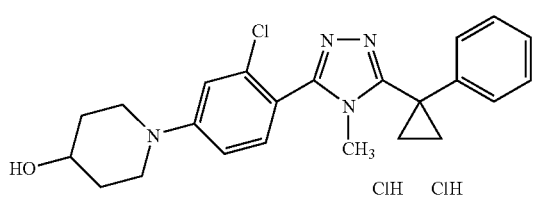 | (300 MHz, DMSO-d6) 1.43 (2H, m), 1.59 (2H, m), 1.69 (2H, m), 1.80 (2H, m), 3.12 (2H, m), 3.36 (3H, s), 3.73 (4H, m), 7.08-7.48 (8H, m) |
| Ex. 1-55 | 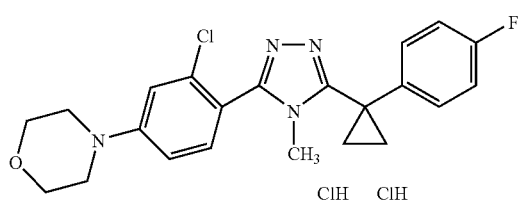 | (300 MHz, DMSO-d6) 1.57 (2H, m), 1.70 (2H, m), 3.32 (4H, t, J = 4.8 Hz), 3.37 (3H, s), 3.74 (4H, t, J = 4.8 Hz), 7.12 (1H, dd, J = 8.8, 2.5 Hz), 7.18-7.30 (5H, m), 7.49 (1H, d, J = 8.8 Hz) |
| Ex. 1-56 | 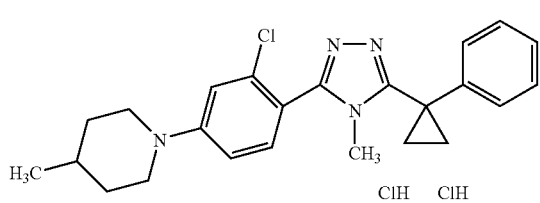 | (300 MHz, DMSO-d6) −0.93 (3H, d, J = 14.6 Hz), 1.18 (2H, m), 1.54-1.69 (7H, m), 2.86 (2H, m), 3.33 (3H, s), 3.90 (2H, m), 7.07 (1H, dd, J = 8.8, 1.8 Hz), 7.14-7.16 (3H, m), 7.28-7.44 (4H, m) |

-continued

| Examples | Molecular Structure | 1H-NMR |
|---|---|---|
| Ex. 1-57 | 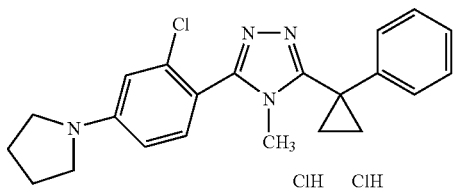<br>ClH   ClH | (300 MHz, DMSO-d6) 1.60 (2H, m), 1.70 (2H, m), 19.8 (4H, quint, J = 3.4 Hz), 3.30 (7H, m), 6.68 (1H, dd, J = 8.8, 2.4 Hz), 6.76 (1H, d, J = 2.2 Hz), 7.18 (2H, m), 7.29 (2H, m), 7.35 (1H, m), 7.43 (1H, d, J = 8.8 Hz) |
| Ex. 1-58 | 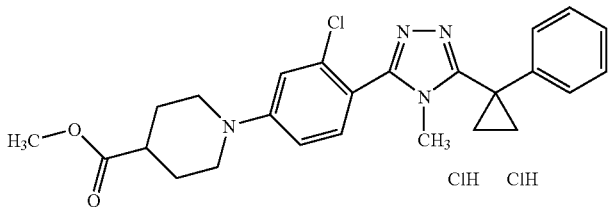<br>ClH   ClH | (300 MHz, DMSO-d6) 1.55-1.64 (5H, m), 1.92 (2H, m), 3.02 (2H, m), 3.38 (3H, s), 3.63 (3H, s), 3.89 (2H, m), 7.12 (1H, dd, J = 8.8, 2.4 Hz), 7.19-7.21 (2H, m), 7.31 (2H, m), 7.39 (2H, m), 7.49 (1H, d, J = 8.8 Hz) |
| Ex. 1-59 | 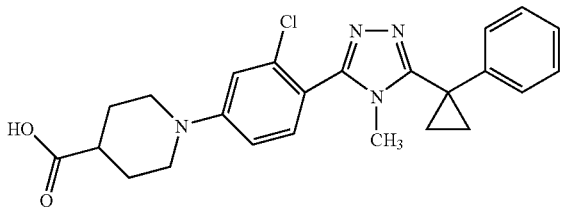 | (300 MHz, DMSO-d6) 1.42 (2H, m), 1.52 (2H, m), 1.63 (2H, m), 1.90 (2H, m), 2.94 (2H, m), 3.17 (3H, s), 7.00-7.05 (3H, m), 7.11 (1H, d, J = 2.6 Hz), 7.22 (1H, m), 7.29-7.34 (3H, m), 12.21 (1H, brs) |
| Ex. 1-60 | 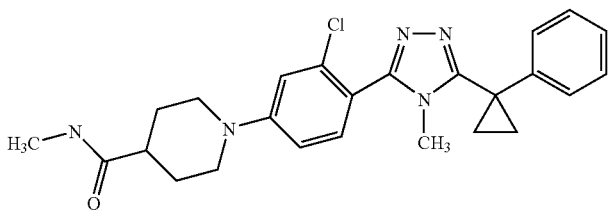 | (300 MHz, DMSO-d6) 1.45 (2H, m), 1.53 (2H, m), 1.64 (2H, m), 1.76 (2H, m), 2.33 (1H, m), 2.57 (3H, d, J = 3.6 Hz), 2.84 (2H, m), 3.17 (3H, s), 3.88 (2H, m), 7.00 (1H, d, J = 2.6 Hz), 7.04 (2H, m), 7.10 (1H, d, J = 2.5 Hz), 7.22 (1H, m), 7.32 (3H, m), 7.74 (1H, d, J = 4.8 Hz) |
| Ex. 1-61 | 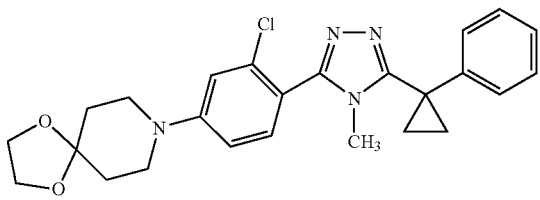 | (300 MHz, DMSO-d6) 1.45 (2H, m), 1.53 (2H, m), 1.69 (4H, t, J = 5.6 Hz), 3.30 (3H, s), 3.43 (4H, t, J = 5.6 Hz), 3.92 (4H, s), 7.01-7.05 (3H, m), 7.14 (1H, d, J = 2.5 Hz), 7.22 (1H, tt, J = 7.4, 2.2 Hz), 7.29-7.34 (3H, m) |
| Ex. 1-62 | 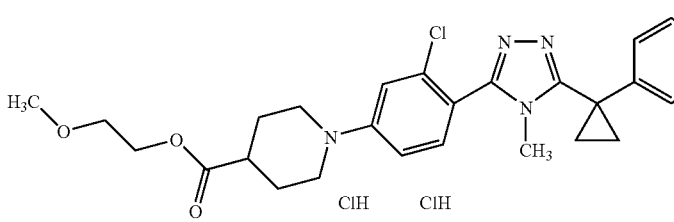<br>ClH   ClH | (300 MHz, DMSO-d6) 1.55-1.71 (5H, m), 1.92 (2H, m), 3.01 (2H, m), 3.26 (3H, s), 3.34 (3H, s), 3.53 (2H, t, J = 4.8 Hz), 3.86 (2H, m), 4.16 (2H, t, J = 4.6 Hz), 7.10 (1H, dd, J = 8.8, 2.6 Hz), 7.08-7.11 (3H, m), 7.29 (1H, m), 7.37 (2H, m), 7.46 (1H, d, J = 8.8 Hz) |
| Ex. 1-63 | 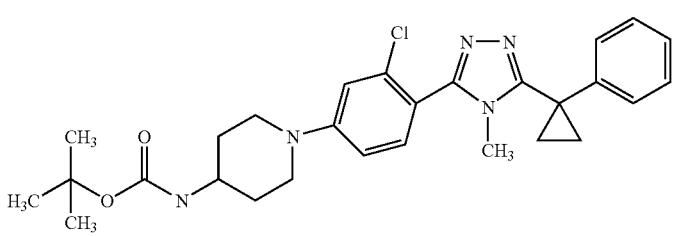 | (300 MHz, DMSO-d6) 1.34-1.56 (16H, m), 1.78 (2H, m), 2.89 (2H, m), 3.26 (3H, s), 3.80 (2H, m), 6.85 (1H, brs), 6.99 (1H, d, J = 2.6 Hz), 7.03 (2H, m), 7.10 (1H, d, J = 2.6 Hz), 7.22 (1H, tt, J = 7.3, 2.2 Hz), 7.30-7.42 (3H, m) |

| Examples | Molecular Structure | 1H-NMR |
|---|---|---|
| Ex. 1-64 | 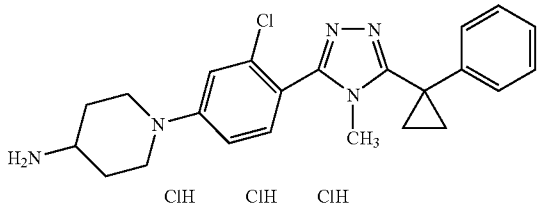 | (300 MHz, DMSO-d6) 1.53-1.68 (6H, m), 1.99 (2H, m), 2.96 (2H, m), 3.25-3.30 (4H, m), 3.98 (2H, m), 7.08 (1H, d, J = 2.2 Hz), 7.13 (2H, m), 7.21 (1H, d, J = 2.2 Hz), 7.26 (1H, m), 7.39 (2H, m), 7.45 (1H, d, J = 8.8 Hz), 8.29 (2H, brs) |
| Ex. 1-65 | 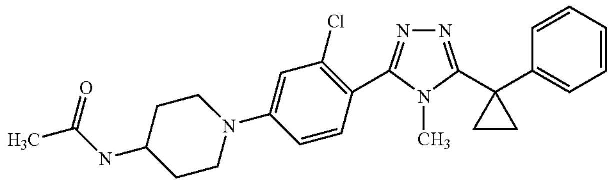 | (300 MHz, DMSO-d6) 1.43-1.48 (4H, m), 1.53 (2H, m), 1.79-1.83 (5H, m), 2.98 (2H, m), 3.30 (3H, s), 3.79-3.83 (3H, m), 7.00-7.05 (3H, m), 7.12 (1H, d, J = 2.2 Hz), 7.22 (1H, m), 7.29-7.34 (3H, m), 7.79 (1H, d, J = 7.7 Hz) |
| Ex. 1-66 | 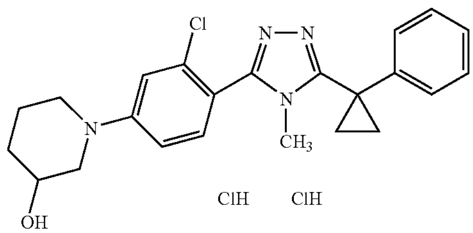 | (300 MHz, DMSO-d6) 1.38-1.55 (4H, m), 1.64 (2H, m), 1.72-1.88 (2H, m), 2.83 (1H, m), 2.96 (1H, m), 3.30 (3H, s), 3.52-3.70 (4H, m), 7.01 (1H, dd, J = 8.8, 2.4 Hz), 7.09 (1H, d, J = 2.6 Hz), 7.11 (2H, m), 7.24 (1H, tt, J = 7.2, 2.1 Hz), 7.32 (2H, m), 7.39 (1H, d, J = 8.9 Hz) |
| Ex. 1-67 | 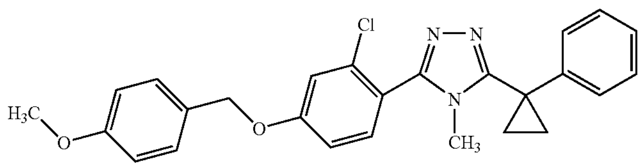 | (300 MHz, DMSO-D6) 1.42-1.59 (4H, m), 3.17 (3H, s), 3.76 (3H, s), 5.14 (2H, s), 6.93-7.51 (12H, m) |
| Ex. 1-68 | 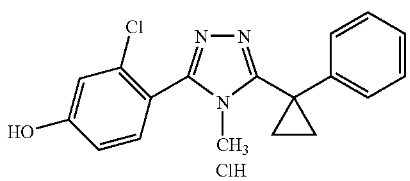 | (400 MHz, DMSO-D6) 1.47-1.72 (4H, m), 3.29 (3H, s), 6.93-7.51 (8H, m), 10.74 (1H, br.s) |
| Ex. 1-69 | 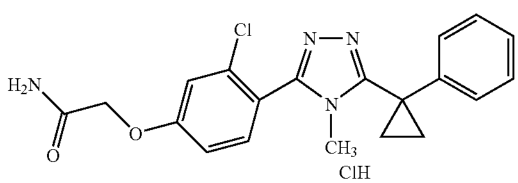 | (300 MHz, DMSO-D6) 1.49-1.73 (4H, m), 3.29 (3H, s), 4.59 (2H, s), 6.16 (1H, br.s), 7.08-7.67 (10H, m) |
| Ex. 1-70 | 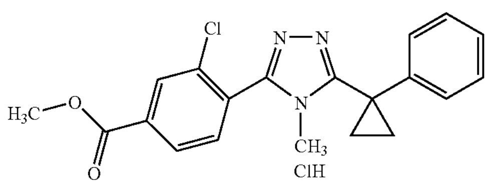 | (300 MHz, DMSO-D6), 1.51-1.55 (2H, m), 1.62-1.66 (2H, m), 3.28 (3H, s), 7.10-7.13 (2H, m), 7.22-7.27 (1H, m), 7.32-7.37 (2H, m), 7.81 (1H, d, J = 7.9 Hz), 8.08 (1H, dd, J = 1.5, 7.9 Hz), 8.14 (1H, d, J = 1.5 Hz) |
| Ex. 1-71 | 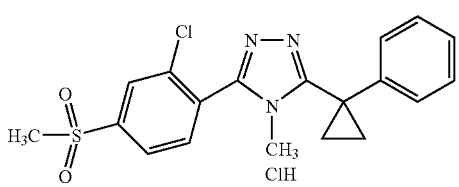 | (300 MHz, DMSO-D6) 1.51-1.55 (2H, m), 1.62-1.66 (2H, m), 3.30 (3H, s), 3.38 (3H, s), 7.11-7.13 (2H, m), 7.23-7.28 (1H, m), 7.33-7.38 (2H, m), 7.94 (1H, d, J = 8.1 Hz), 8.09 (1H, dd, J = 1.6, 8.1 Hz), 8.24 (1H, d, J = 1.6 Hz) |

-continued

| Examples | Molecular Structure | 1H-NMR |
|---|---|---|
| Ex. 1-72 | 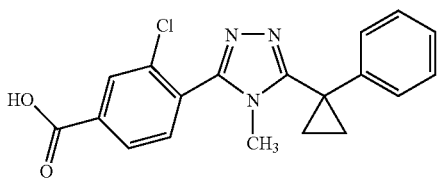 | (300 MHz, DMSO-D6), 1.46-1.51 (2H, m), 1.54-1.60 (2H, m), 3.22 (3H, s), 7.05-7.08 (2H, m), 7.20-7.25 (1H, m), 7.30-7.36 (2H, m), 7.74 (1H, d, J = 8.1 Hz), 8.03 (1H, dd, J = 1.4, 8.1 Hz), 8.09 (1H, d, J = 1.4 Hz) |
| Ex. 1-73 | 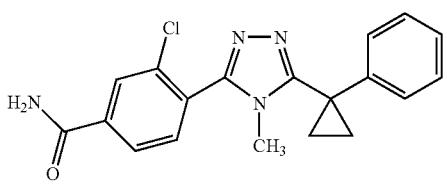 | (300 MHz, DMSO-D6), 1.46-1.49 (2H, m), 1.55-1.59 (2H, m), 3.21 (3H, s), 7.05-7.08 (2H, m), 7.20-7.25 (1H, m), 7.30-7.35 (2H, m), 7.66 (1H, brs), 7.69 (1H, d, J = 8.1 Hz), 7.98 (1H, dd, J = 1.6, 8.1 Hz), 8.11 (1H, d, J = 1.6 Hz), 8.21 (1H, brs) |
| Ex. 1-74 | 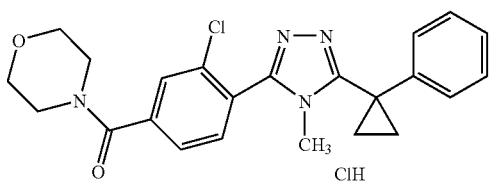 | (300 MHz, DMSO-D6), 1.50-1.54 (2H, m), 1.60-1.64 (2H, m), 3.28 (3H, s), 3.37 (2H, brs), 3.63 (6H, brs), 7.09-7.12 (2H, m), 7.22-7.27 (1H, m), 7.32-7.37 (2H, m), 7.57 (1H, dd, J = 1.5, 7.8 Hz), 7.70 (1H, d, J = 7.8 Hz), 7.74 (1H, d, J = 1.5 Hz) |
| Ex. 1-75 | 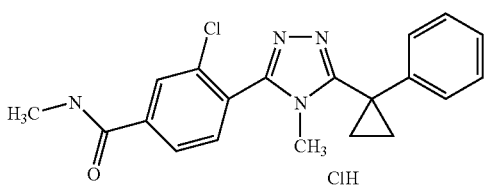 | (300 MHz, DMSO-D6), 1.49-1.54 (2H, m), 1.57-1.63 (2H, m), 2.82 (3H, d, J = 4.5 Hz), 3.25 (3H, s), 7.09-7.11 (2H, m), 7.22-7.27 (1H, m), 7.32-7.37 (2H, m), 7.72 (1H, d, J = 8.1 Hz), 7.96 (1H, dd, J = 1.5, 8.1 Hz), 8.09 (1H, d, J = 1.5 Hz), 8.74 (1H, q, J = 4.5 Hz) |
| Ex. 1-76 | 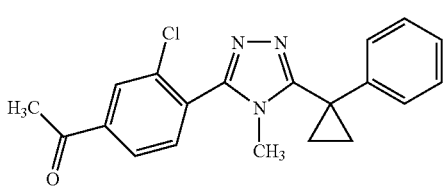 | (300 MHz, DMSO-D6), 1.44-1.47 (2H, m), 1.53-1.57 (2H, m), 3.17 (3H, s), 3.85 (3H, s), 7.04-7.10 (3H, m), 7.19-7.25 (2H, m), 7.30-7.35 (2H, m), 7.48 (1H, d, J = 9.0 Hz) |
| Ex. 1-77 | 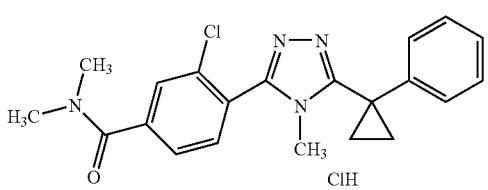 | (300 MHz, DMSO-D6), 1.50-3.54 (2H, m), 1.61-1.64 (2H, m), 2.94 (3H, s), 3.01 (3H, s), 3.28 (3H, s), 7.09-7.12 (2H, m), 7.22-7.27 (1H, m), 7.32-7.37 (2H, m), 7.56 (1H, d, J = 7.8 Hz), 7.69 (1H, d, J = 7.8 Hz), 7.72 (1H, s) |
| Ex. 1-78 | 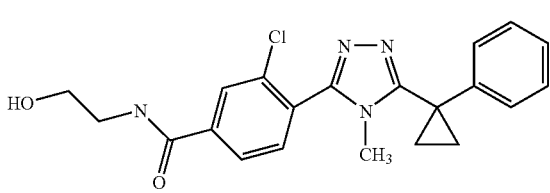 | (300 MHz, DMSO-D6), 1.46-1.49 (2H, m), 1.55-1.59 (2H, m), 3.21 (3H, s), 3.35 (2H, dt, J = 5.8, 5.8 Hz), 3.53 (2H, dt, J = 5.8, 5.8 Hz), 4.74 (1H, t, J = 5.8 Hz), 7.06-7.08 (2H, m), 7.20-7.25 (1H, m), 7.31-7.35 (2H, m), 7.69 (1H, d, J = 8.1 Hz), 7.96 (1H, dd, J = 1.6, 8.1 Hz), 8.11 (1H, d, J = 1.6 Hz), 8.70 (1H, t, J = 5.8 Hz) |

| Examples | Molecular Structure | 1H-NMR |
|---|---|---|
| Ex. 1-79 | 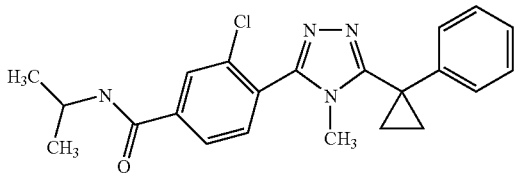 | (300 MHz, DMSO-6), 1.18 (6H, d, J = 6.6 Hz), 1.45-1.51 (2H, m), 1.54-1.59 (2H, m), 3.20 (3H, s), 4.11 (1H, m), 7.06-7.08 (2H, m), 7.20-7.25 (1H, m), 7.30-7.36 (2H, m), 7.68 (1H, d, J = 8.1 Hz), 7.95 (1H, dd, J = 1.7, 8.1 Hz), 8.09 (1H, d, J = 1.7 Hz), 8.48 (1H, d, J = 7.5 Hz) |
| Ex. 1-80 | 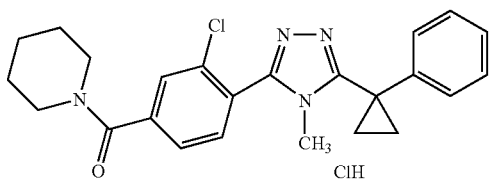 | (300 MHz, DMSO-D6), 1.50-1.64 (10H, m), 3.28 (5H, brs), 3.60 (2H, brs), 7.09-7.12 (2H, m), 7.22-7.27 (1H, m), 7.32-7.37 (2H, m), 7.52 (1H, dd, J = 1.4, 7.8 Hz), 7.69 (1H, d, J = 1.4 Hz), 7.69 (1H, d, J = 7.8 Hz) |
| Ex. 1-81 | 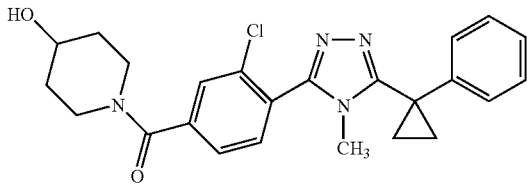 | (300 MHz, DMSO-D6), 1.40 (2H, brs), 1.45-1.51 (2H, m), 1.54-1.59 (2H, m), 1.76 (2H, brs), 3.22 (5H, brs), 3.48 (1H, brs), 3.75 (1H, m), 3.98 (1H, brs), 4.79 (1H, d, J = 4.2 Hz), 7.05-7.07 (2H, m), 7.20-7.25 (1H, m), 7.30-7.35 (2H, m), 7.50 (1H, dd, J = 1.6, 7.6 Hz), 7.64 (1H, d, J = 7.6 Hz), 7.66 (1H, d, J = 1.6 Hz) |
| Ex. 1-82 | 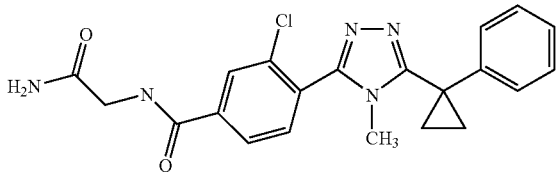 | (300 MHz, DMSO-D6), 1.46-1.51 (2H, m), 1.54-1.59 (2H, m), 3.21 (3H, s), 3.84 (2H, d, J = 5.7 Hz), 7.06-7.09 (3H, m), 7.20-7.25 (1H, m), 7.31-7.36 (2H, m), 7.42 (1H, brs), 7.71 (1H, d, J = 8.0 Hz), 7.98 (1H, dd, J = 1.8, 8.0 Hz), 8.14 (1H, d, J = 1.8 Hz), 8.96 (1H, t, J = 5.7 Hz) |
| Ex. 1-83 | 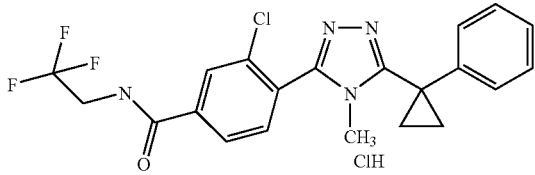 | (300 MHz, DMSO-D6), 1.52-1.56 (2H, m), 1.59-1.64 (2H, m), 3.27 (3H, s), 4.14 (2H, m), 7.10-7.13 (2H, m), 7.22-7.27 (1H, m), 7.32-7.37 (2H, m), 7.78 (1H, d, J = 8.0 Hz), 8.04 (1H, dd, J = 1.5, 8.0 Hz), 8.17 (1H, d, J = 1.5 Hz), 9.42 (1H, t, J = 6.3 Hz) |
| Ex. 1-84 | 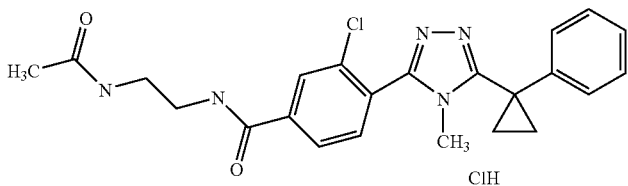 | (300 MHz, DMSO-D6), 1.50-1.55 (2H, m), 1.58-1.64 (2H, m), 1.91 (3H, s), 3.21-3.34 (4H, m), 3.26 (3H, s), 7.10-7.12 (2H, m), 7.22-7.27 (1H, m), 7.32-7.37 (2H, m), 7.74 (1H, d, J = 8.1 Hz), 7.96-8.00 (2H, m), 8.11 (1H, d, J = 1.8 Hz), 8.82 (1H, t, J = 6.2 Hz) |
| Ex. 1-85 | 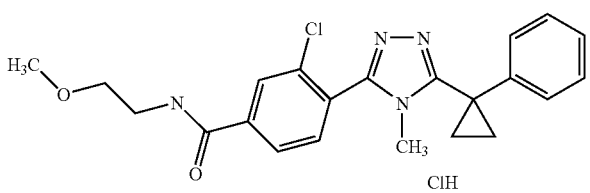 | (300 MHz, DMSO-D6), 1.49-1.55 (2H, m), 1.58-1.63 (2H, m), 3.25 (3H, s), 3.27 (3H, s), 3.42-3.50 (4H, m), 7.09-7.11 (2H, m), 7.22-7.27 (1H, m), 7.32-7.37 (2H, m), 7.73 (1H, d, J = 7.8 Hz), 7.99 (1H, dd, J = 1.5, 7.8 Hz), 8.12 (1H, d, J = 1.5 Hz), 8.82 (1H, brs) |

-continued

| Examples | Molecular Structure | 1H-NMR |
|---|---|---|
| Ex. 1-86 | [structure] ClH | (300 MHz, DMSO-D6), 1.51-1.57 (2H, m), 1.60-1.66 (2H, m), 2.03 (3H, s), 3.20-3.70 (8H, m), 3.29 (3H, s), 7.10-7.12 (2H, m), 7.23-7.27 (1H, m), 7.32-7.37 (2H, m), 7.58 (1H, dd, J = 4.5, 8.0 Hz), 7.72 (1H, d, J = 8.0 Hz), 7.76 (1H, d, J = 1.5 Hz) |
| Ex. 1-87 | [structure] | (300 MHz, DMSO-D6), 1.45-1.50 (2H, m), 1.54-1.59 (2H, m), 2.18 (6H, s), 2.41 (2H, t, J = 6.4 Hz), 3.21 (3H, s), 3.38 (2H, dt, J = 6.4, 6.4 Hz), 7.05-7.08 (2H, m), 7.20-7.25 (1H, m), 7.30-7.35 (2H, m), 7.69 (1H, d, J = 7.8 Hz), 7.94 (1H, dd, J = 1.9, 7.8 Hz), 8.08 (1H, d, J = 1.9 Hz), 8.65 (1H, t, 6.4 Hz) |
| Ex. 1-88 | [structure] | (300 MHz, DMSO-D6), 1.46-1.51 (2H, m), 1.54-1.59 (2H, m), 2.40-2.43 (4H, m), 2.48-2.51 (2H, m), 3.21 (3H, s), 3.41 (2H, dt, J = 5.9, 5.9 Hz), 3.55-3.59 (4H, m), 7.06-7.08 (2H, m), 7.20-7.25 (1H, m), 7.31-7.35 (2H, m), 7.70 (1H, d, J = 8.0 Hz), 7.94 (1H, dd, J = 1.5, 8.0 Hz), 8.07 (1H, d, J = 1.5 Hz), 8.68 (1H, t, J = 5.9 Hz) |
| Ex. 1-89 | [structure] HCl   HCl | (300 MHz, DMSO-d6) 1.56 (2H, m), 1.66 (2H, m) 3.02 (6H, s), 3.32 (3H, s), 6.83 (1H, dd, J = 8.8, 2.6 Hz), 6.91 (1H, d, J = 1.5 Hz), 7.15 (2H, m), 7.27 (1H, m), 7.37 (1H, t, 7.4 Hz), 7.42 (1H, d, 8.8 Hz) |
| Ex. 1-90 | [structure] HCl   HCl | (300 MHz, DMSO-d6) 1.57 (2H, m), 1.66 (2H, m), 3.30 (4H, t, J = 4.9 Hz), 3.32 (3H, s) 3.74 (4H, t, J = 4.9 Hz), 7.09 (1H, dd, J = 8.8, 2.6 Hz), 7.14-7.37 (6H, m), 7.48 (1H, d, J = 7.2 Hz) |
| Ex. 1-91 | [structure] HCl | (300 MHz, DMSO-d6) 1.57 (2H, m), 1.691 (2H, m), 3.34 (3H, s), 3.85 (3H, s), 7.17 (2H, d, J = 7.6 Hz), 7.26-7.31 (2H, m), 7.38 (3H, t, J = 7.4 Hz), 7.56 (1H, d, J = 8.1 Hz) |
| Ex. 1-92 | [structure] HCl | (300 MHz, DMSO-d6) 1.57 (2H, m), 1.68 (2H, m), 3.31 (3H, s), 7.15 (2H, m), 7.27 (1H, tt, J = 7.4, 2.2 Hz), 7.36 (2H, m), 7.50 (1H, m), 7.74-7.80 (2H, m) |

-continued
| Examples | Molecular Structure | 1H-NMR |
|---|---|---|
| Ex. 1-93 | 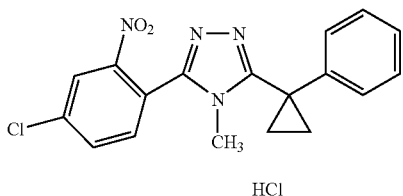 | (300 MHz, DMSO-d6) 1.52 (2H, m), 1.58 (2H, m), 3.27 (3H, s), 7.09-7.12 (2H, m), 7.25 (1H, m), 7.32-7.35 (2H, m), 7.86 (1H, d, J = 8.1 Hz), 8.08 (1H, dd, J = 8.1, 2.2 Hz), 8.41 (1H, d, J = 2.2 Hz) |
| Ex. 1-94 | 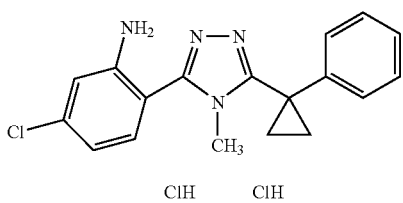 | (300 MHz, DMSO-d6) 1.56 (2H, m), 1.74 (2H, m), 3.40 (3H, s), 5.20 (2H, brs), 6.74 (1H, dd, J = 8.4, 2.2 Hz), 6.93 (1H, d, J = 2.2 Hz), 7.25-7.38 (6H, m) |
| Ex. 1-95 | 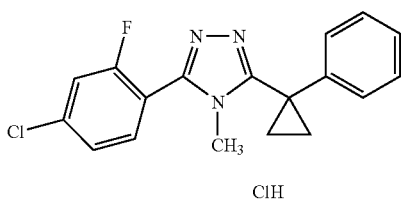 | (300 MHz, DMSO-d6) 1.53 (2H, m), 1.62 (2H, m), 3.36 (3H, d, J = 1.5 Hz), 7.13-7.16 (2H, m), 7.25 (1H, tt, J = 7.4, 2.8 Hz), 7.31-7.37 (2H, m), 7.53 (1H, dd, J = 7.7, 3.4 Hz), 7.69-7.76 (2H, m) |
| Ex. 1-96 | 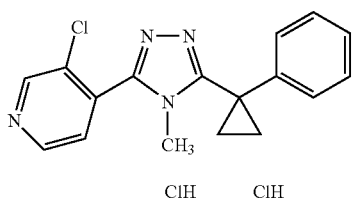 | (300 MHz, DMSO-D6), 1.49-1.55 (2H, m), 1.58-1.63 (2H, m), 3.30 (3H, s), 7.10-7.13 (2H, m), 7.22-7.27 (1H, m), 7.32-7.37 (2H, m), 7.71 (1H, d, J = 4.5 Hz), 8.75 (1H, d, J = 4.5 Hz), 8.90 (1H, s) |
| Ex. 1-97 | 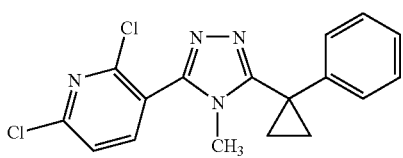 | (300 MHz, DMSO-D6), 1.46-1.50 (2H, m), 1.54-1.58 (2H, m), 3.26 (3H, s), 7.06-7.09 (2H, m), 7.20-7.25 (1H, m), 7.30-7.35 (2H, m), 7.79 (1H, d, J = 8.1 Hz), 8.17 (1H, d, J = 8.1 Hz) |
| Ex. 1-98 | 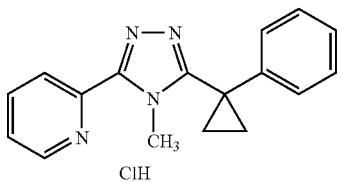 | (300 MHz, DMSO-D6), 1.56-1.72 (4H, m), 3.86 (3H, s), 7.13-7.18 (2H, m), 7.23-7.37 (3H, m), 7.57-7.62 (1H, m), 8.03-8.10 (1H, m), 8.15-8.21 (1H, m), 8.72-8.76 (1H, m) |
| Ex. 1-99 | 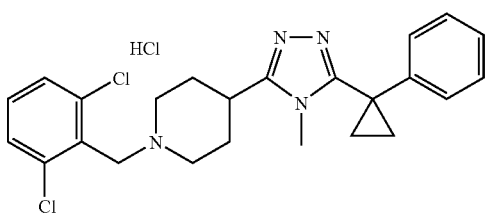 | |

-continued

| Examples | Molecular Structure | 1H-NMR |
| --- | --- | --- |
| Ex. 1-100 | 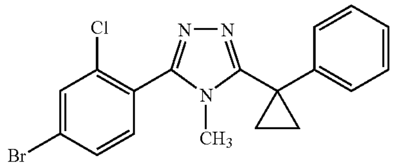 | (CDCl$_3$, 400 MHz) δ: 7.59 (d, J = 1.8 Hz, 1H), 7.52 (m, 1H), 7.31 (d, J = 8.3 Hz, 1H), 7.22 (m, 2H), 7.14 (m, 1H), 7.05 (m, 2H), 3.17 (s, 3H), 1.58 (m, 2H), 1.40 (m, 2H). |
| Ex. 1-101 | 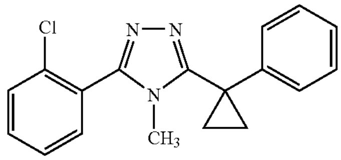 | (CDCl$_3$, 400 MHz) δ: 7.52-7.14 (m, 9H), 3.24 (s, 3H), 1.68 (m, 2H), 1.48 (m, 2H). |
| Ex. 1-102 | 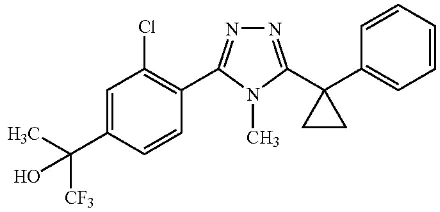 | (CDCl$_3$, 400 MHz) δ: 7.76 (d, J = 1.3 Hz, 1H), 7.53 (m, 1H), 7.44 (d, J = 8.1 Hz, 1H), 7.33-7.14 (m, 4H), 7.14 (m, 1H), 7.09 (m, 2H), 3.24 (s, 3H), 1.68 (m, 2H), 1.49 (m, 2H). |
| Ex. 1-103 | 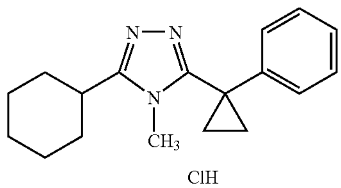 | |
| Ex. 1-104 | 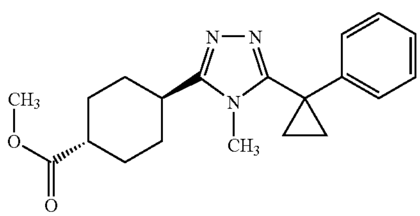 | |
| Ex. 1-105 | 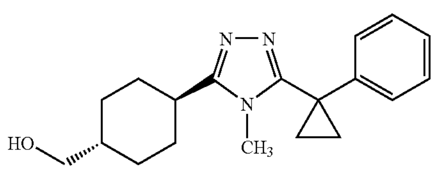 | |
| Ex. 1-106 | 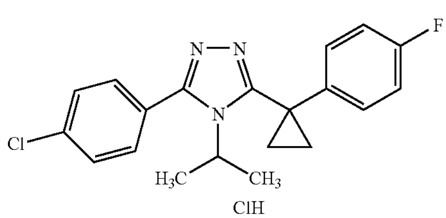 | |
| Ex. 1-107 | 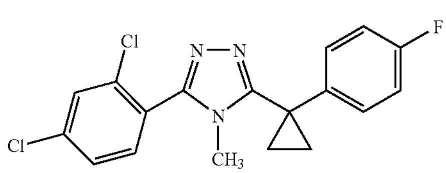 | |

-continued
| Examples | Molecular Structure | 1H-NMR |
|---|---|---|
| Ex. 1-108 | 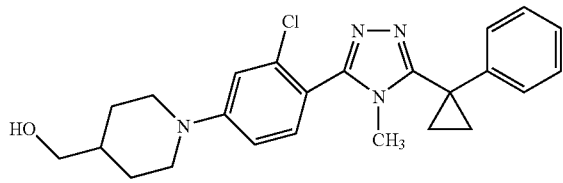 | |
| Ex. 1-109 | 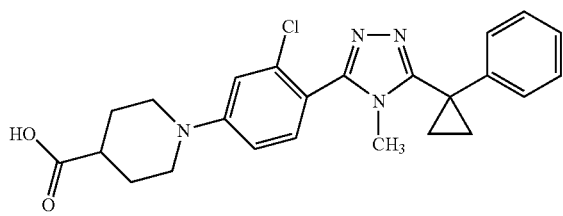 | |
| Ex. 1-110 | 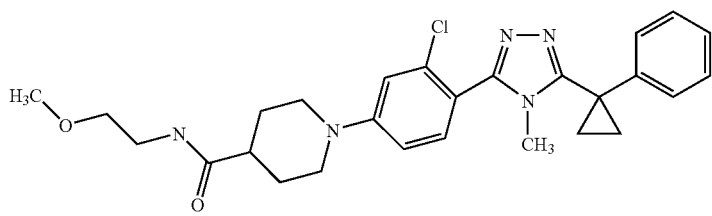 | |
| Ex. 1-111 | 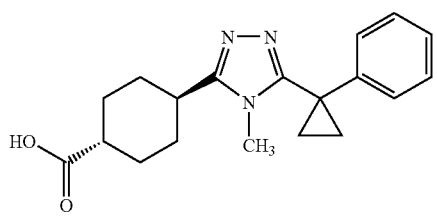 | |
| Ex. 1-112 | 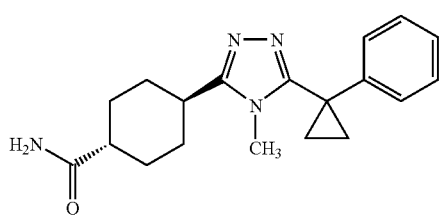 | |
| Ex. 1-113 | 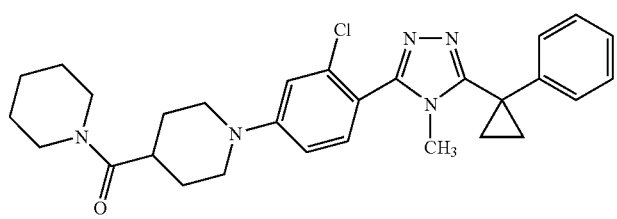 | |
| Ex. 1-114 | 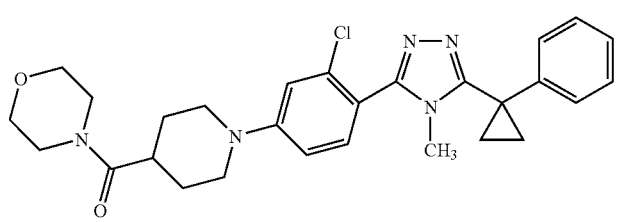 | |

-continued
| Examples | Molecular Structure | 1H-NMR |
|---|---|---|
| Ex. 1-115 | 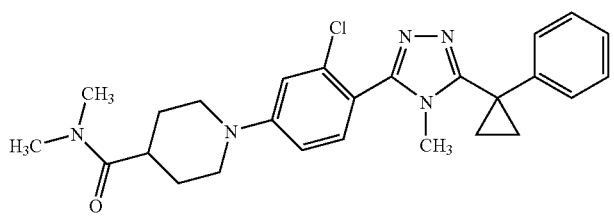 | |
| Ex. 1-116 | 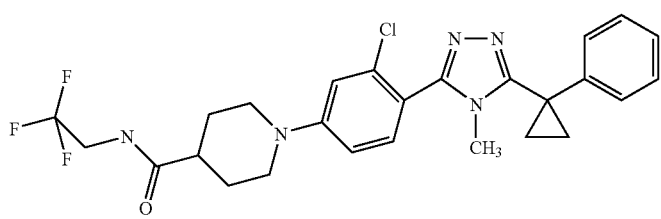 | |
| Ex. 1-117 | 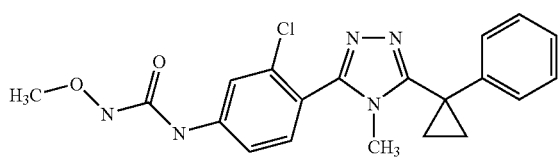 | (400 MHz, DMSO-d6) δ: 1.46-1.48 (2H, m), 1.51-1.61 (2H, m), 3.19 (3H, s), 3.71 (3H, s), 7.04-7.09 (2H, m), 7.22-7.26 (1H, m), 7.31-7.34 (2H, m), 7.44-7.50 (1H, m), 7.74 (1H, dd, J = 8.6, 2.1 Hz), 7.97-8.03 (1H, m), 9.34 (1H, s), 9.82 (1H, s) |
| Ex. 1-118 | 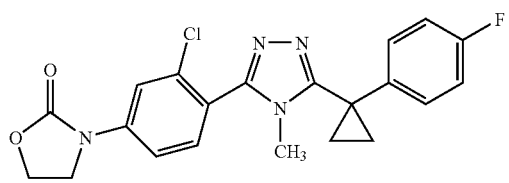 | (400 MHz, DMSO-d6) δ: 1.46-1.47 (2H, m), 1.52-1.56 (2H, m), 3.32 (3H, s), 4.14 (2H, t, J = 8.0 Hz), 4.49 (2H, t, J = 8.0 Hz), 7.11-7.17 (4H, m), 7.59 (1H, d, J = 8.3 Hz), 7.67 (1H, dd, J = 8.3, 1.9 Hz), 7.92 (1H, d, J = 1.9 Hz). |
| Ex. 1-119 | 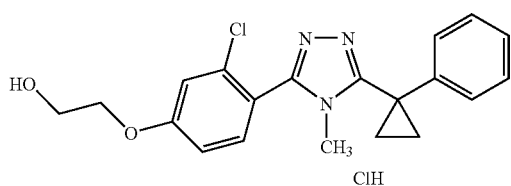 | |
| Ex. 1-120 | 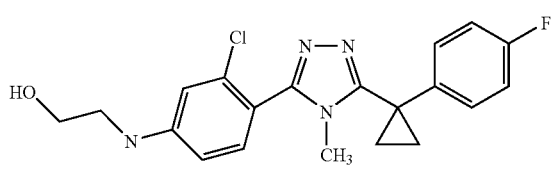 | |
| Ex. 1-121 | 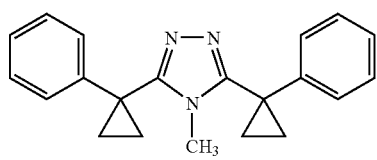 | |
| Ex. 1-122 | 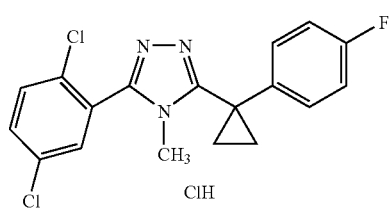 | |

-continued

| Examples | Molecular Structure | 1H-NMR |
|---|---|---|
| Ex. 1-123 | 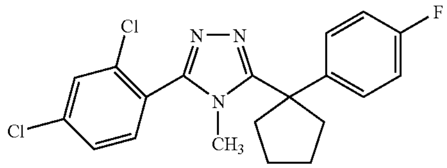 | |
| Ex. 1-124 | 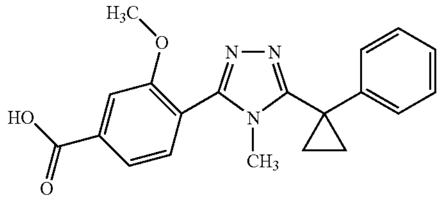 | |
| Ex. 1-125 | 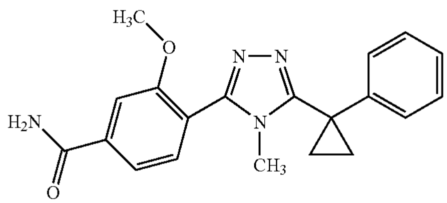 | (300 MHz, DMSO-d6) δ: 1.42-1.56 (4H, m), 3.18 (3H, s), 3.82 (3H, s), 7.02-7.06 (2H, m), 7.19-7.35 (3H, m), 7.50-7.59 (4H, m), 8.10 (1H, s). |
| Ex. 1-126 | 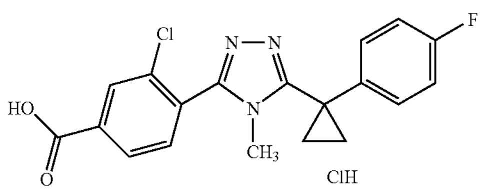 | |
| Ex. 1-127 | 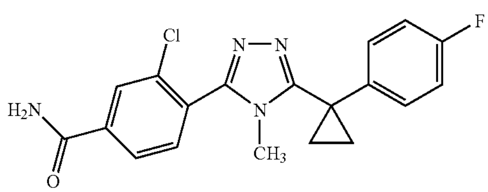 | (300 MHz, DMSO-d6) δ: 1.44-1.58 (4H, m), 3.22 (3H, s), 7.10-7.19 (4H, m), 7.67-7.69 (2H, m), 7.96-7.99 (1H, m), 8.11-8.11 (1H, m), 8.21 (1H, s). |
| Ex. 1-128 | 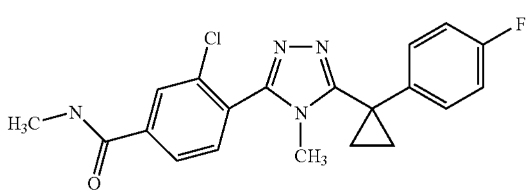 | (400 MHz, DMSO-d6) δ: 1.45-1.57 (4H, m), 2.81 (3H, d, J = 4.6 Hz), 3.15 (3H, s), 7.12-7.15 (4H, m), 7.67-7.69 (1H, m), 7.92-7.94 (1H, m), 8.05-8.06 (1H, m), 8.70 (1H, q, J = 4.6 Hz). |
| Ex. 1-129 | 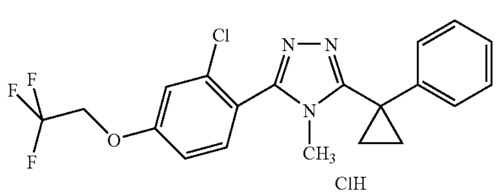 | |
| Ex. 1-130 | 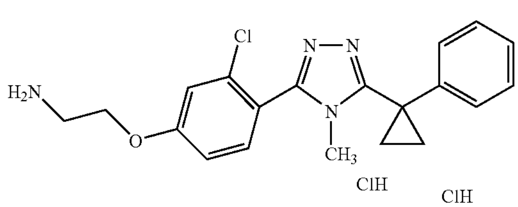 | |

| Examples | Molecular Structure | 1H-NMR |
|---|---|---|
| Ex. 1-131 | 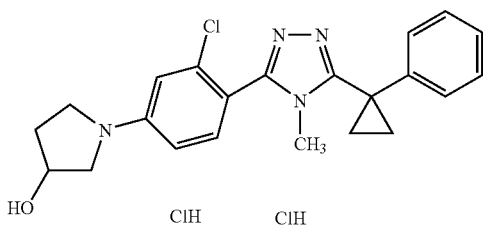 | |
| Ex. 1-132 | 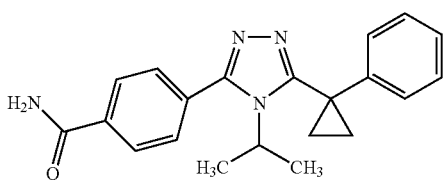 | (300 MHz, DMSO-d6) δ: 0.94 (6H, d, J =7.0 Hz), 1.46-1.60 (4H, m), 4.52 (1H, septet. J = 7.0 Hz), 7.13-7.35 (5H, m), 7.48 (1H, s), 7.59 (2H, d, J = 8.4 Hz), 7.98 (2H, d, J = 8.4 Hz), 8.09 (1H, s). |
| Ex. 1-133 | 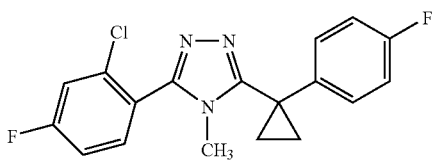 | |
| Ex. 1-134 | 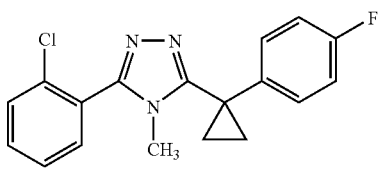 | (CDCl₃, 400 MHz) δ: 7.48 (m, 3H), 7.39 (m, 1H), 7.14 (m, 2H), 6.98 (m, 2H), 3.24 (s, 3H), 1.67 (m, 2H), 1.43 (m, 2H). |
| Ex. 1-135 | 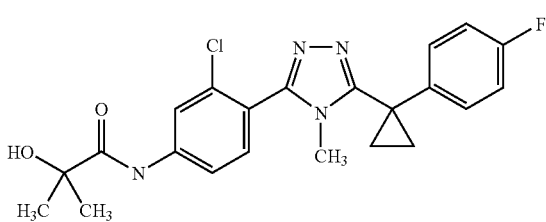 | |
| Ex. 1-136 | 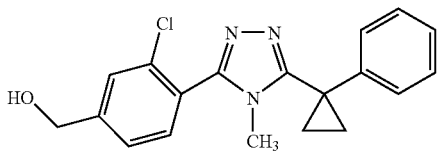 | |
| Ex. 1-137 | 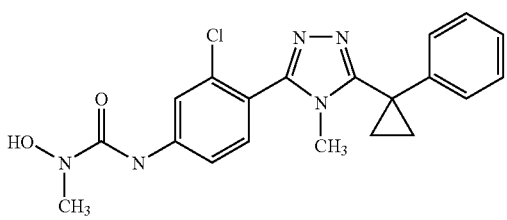 | (400 MHz, DMSO-d6) δ: 1.45-1.46 (2H, m), 1.51-1.55 (2H, m), 3.01 (3H, s), 3.19 (3H, s), 7.03-7.14 (2H, m), 7.17-7.20 (1H, m), 7.31 (2H, t, J = 7.7 Hz), 7.43-7.46 (1H, m), 7.76 (1H, dd, J = 8.3, 1.9 Hz), 8.04 (1H, d, J = 1.9 Hz), 9.43 (1H, s), 9.90 (1H, s). |

| Examples | Molecular Structure | 1H-NMR |
|---|---|---|
| Ex. 1-138 | 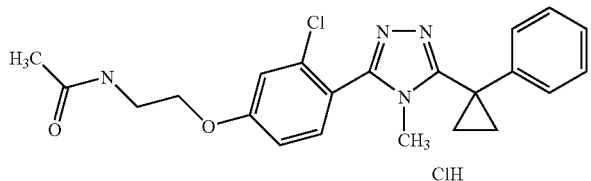 ClH | |
| Ex. 1-139 | 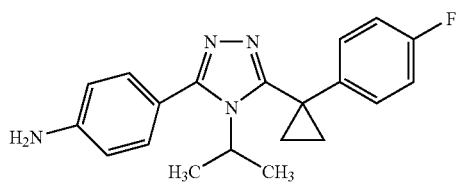 | |
| Ex. 1-140 | 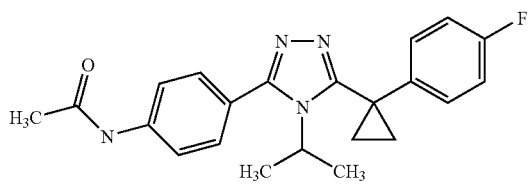 | |
| Ex. 1-141 | 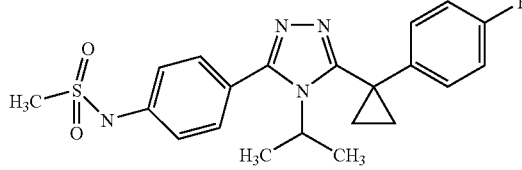 | |
| Ex. 1-142 | 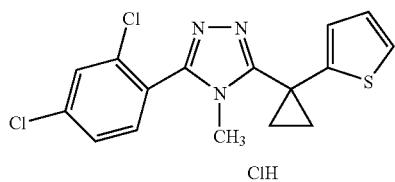 ClH | |
| Ex. 1-143 | 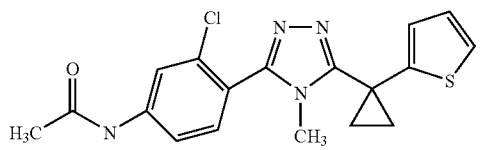 | |
| Ex. 1-144 | 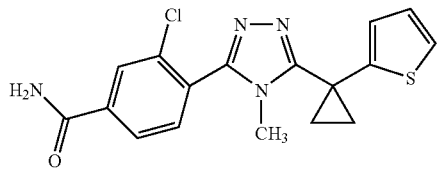 | (400 MHz, DMSO-d6) δ: 1.47-1.70 (4H, m), 3.37 (3H, s), 6.85-6.95 (2H, m), 7.37-7.38 (1H, m), 7.65-7.67 (2H, m), 7.94-7.98 (1H, m), 8.10-8.11 (1H, m), 8.22 (1H, s). |
| Ex. 1-145 | 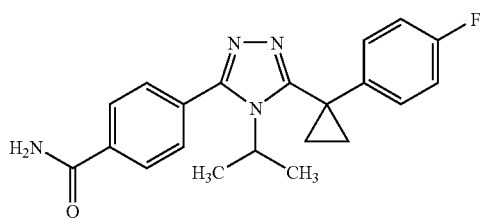 | (300 MHz, DMSO-d6) δ: 1.02 (6H, J = 7.0 Hz)), 1.48-1.56 (4H, m), 4.53 (1H, septet. J = 7.0 Hz), 7.14-7.21 (4H, m), 7.50 (1H, s), 7.57-7.60 (2H, m), 7.98-8.01 (2H, m), 8.10 (1H, s). |

-continued
| Examples | Molecular Structure | 1H-NMR |
|---|---|---|
| Ex. 1-146 | 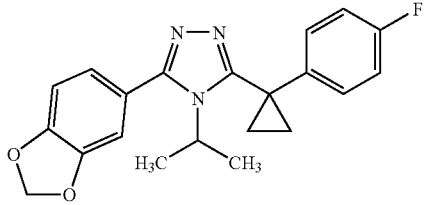 | |
| Ex. 1-147 | 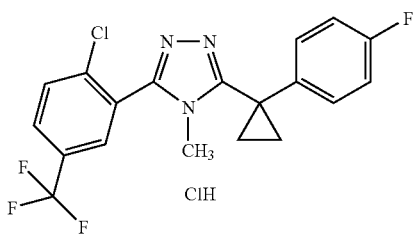 | |
| Ex. 1-148 | 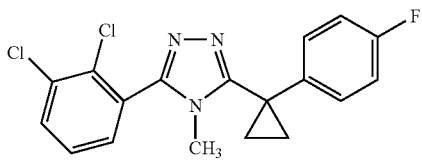 | |
| Ex. 1-149 | 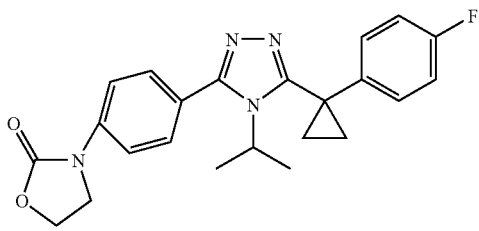 | (300 MHz, DMSO-d6) δ: 0.98 (6H, d, J = 7.0 Hz), 1.45-1.47 (2H, m), 1.50-1.58 (2H, m), 4.11-4.14 (2H, m), 4.45-4.56 (3H, m), 7.12-7.23 (4H, m), 7.51 (2H, d, J = 8.8 Hz), 7.65 (2H, d, J = 8.8 Hz). |
| Ex. 1-150 | 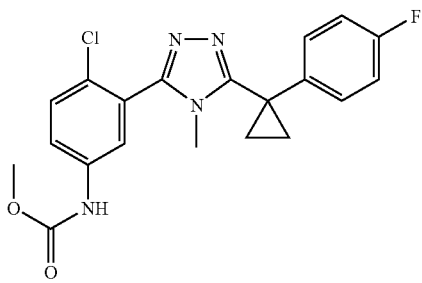 | (400 MHz, DMSO-d6) δ: 1.44-1.50 (2H, m), 1.52-1.58 (2H, m), 3.13 (3H, s), 3.70 (3H, s), 7.11-7.16 (4H, m), 7.56-7.57 (1H, m), 7.65 (2H, dd, J = 7.2, 2.6 Hz), 10.01 (1H, s). |
| Ex. 1-151 | 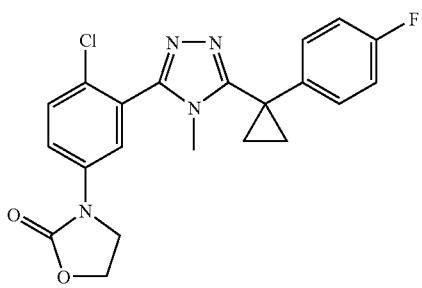 | (400 MHz, DMSO-d6) δ: 1.45-1.47 (2H, m), 1.51-1.58 (2H, m), 3.21 (3H, s), 4.09 (2H, t, J = 7.9 Hz), 4.46 (2H, t, J = 7.9 Hz), 7.10-7.18 (4H, m), 7.67 (1H, d, J = 8.8 Hz), 7.78 (2H, dt, J = 14.7, 5.1 Hz). |

-continued
| Examples | Molecular Structure | 1H-NMR |
|---|---|---|
| Ex. 1-152 | 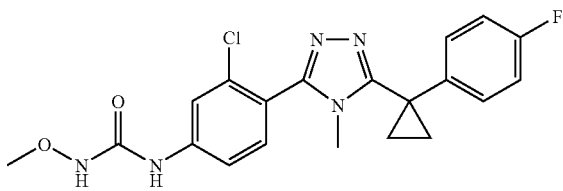 | (300 MHz, DMSO-d6) δ: 1.42-1.45 (2H, m), 1.52-1.55 (2H, m), 3.19 (3H, s), 3.64 (3H, s), 7.09-7.19 (4H, m), 7.45 (1H, d, J = 8.4 Hz), 7.74 (1H, dd, J = 8.4, 2.2 Hz), 8.00 9.83 (1H, s). |
| Ex. 1-153 | 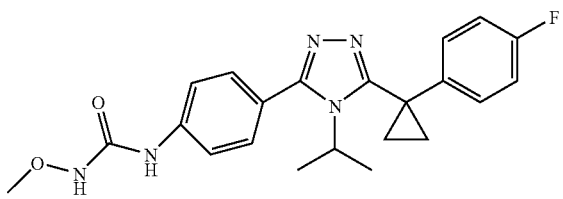 | (300 MHz, DMSO-d6) δ: 0.98 (6H, d, J = 7.0 Hz), 1.44-1.46 (2H, m), 1.49-1.57 (2H, m), 3.64 (3H, s), 4.50 (1H, sept, J = 7.0 Hz), 7.09-7.17 (4H, m), 7.36 (2H, d, J = 8.4 Hz), 7.72 (2H, d, J = 8.8 Hz), 9.09 (1H, s), 9.63 (1H, s). |
| Ex. 1-154 | 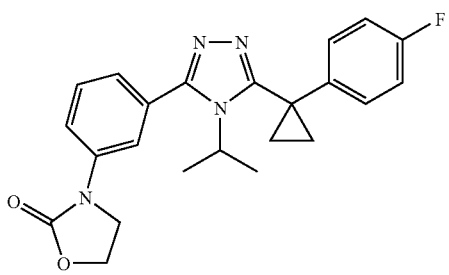 | (300 MHz, DMSO-d6) δ: 1.00 (6H, d, J = 7.0 Hz), 1.44-1.51 (2H, m), 1.53-1.59 (2H, m), 4.04-4.10 (2H, m), 4.41-4.50 (2H, m), 4.53 (1H, sept, J = 7.0 Hz), 7.12-7.25 (5H, m), 7.53 (1H, t, J = 7.9 Hz), 7.65-7.68 (1H, m), 7.78 (1H, t, J = 1.8 Hz). |
| Ex. 1-155 | 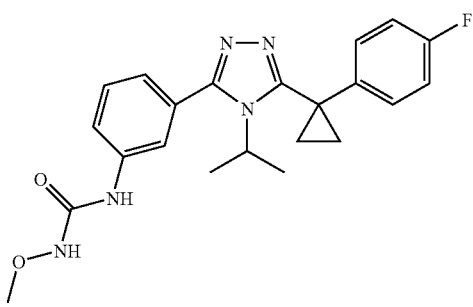 | (400 MHz, DMSO-d6) δ: 0.99 (6H, d, J = 7.0 Hz), 1.45-1.46 (2H, m), 1.56-1.58 (2H, m), 3.61 (3H, s), 4.51 (1H, sept, J = 7.0 Hz), 7.08 (1H, d, J = 7.4 Hz), 7.14-7.18 (4H, m), 7.38 (1H, t, J = 7.9 Hz), 7.71 (1H, d, J = 7.4 Hz), 7.78 (1H, t, J = 1.9 Hz), 9.06 (1H, s), 9.59 (1H, s). |
| Ex. 1-156 | 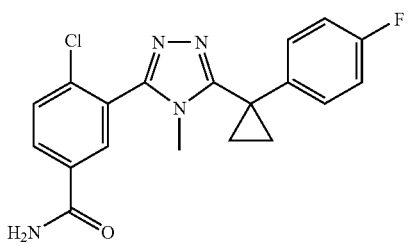 | (300 MHz, DMSO-d6) δ: 1.44-1.57 (4H, m), 3.24 (3H, s), 7.14-7.17 (4H, m), 7.56 (1H, s), 7.76-7.79 (1H, m), 8.05-8.13 (3H, m). |
| Ex. 1-157 | 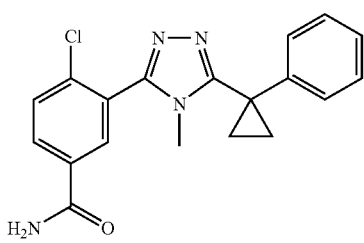 | (400 MHz, DMSO-d6) δ: 1.47-1.58 (4H, m), 2.99 (3H, s), 7.06-7.07 (2H, m), 7.21-7.23 (1H, m), 7.32-7.34 (2H, m), 7.58-7.62 (1H, m), 7.77-7.78 (1H, m), 8.07-8.08 (2H, m), 8.15 (1H, s). |

-continued

| Examples | Molecular Structure | 1H-NMR |
|---|---|---|
| Ex. 1-158 | 3-chloro-4-[4-ethyl-5-(1-phenylcyclopropyl)-4H-1,2,4-triazol-3-yl]benzamide | (400 MHz, DMSO-d6) δ: 0.73 (3H, t, J = 7.2 Hz), 1.48-1.59 (4H, m), 3.66 (2H, q, J = 7.2 Hz), 7.19-7.28 (5H, m), 7.68-7.70 (2H, m), 7.95-7.97 (1H, m), 8.10-8.10 (1H, m), 8.22 (1H, s). |
| Ex. 1-159 | 3-chloro-4-{4-ethyl-5-[1-(4-fluorophenyl)cyclopropyl]-4H-1,2,4-triazol-3-yl}benzamide | (400 MHz, DMSO-d6) δ: 0.73 (3H, t, J = 7.2 Hz), 1.50-1.54 (4H, m), 3.63 (2H, q, J = 7.2 Hz), 7.14-7.22 (4H, m), 7.66-7.69 (2H, m), 7.95-7.97 (1H, m), 8.10-8.10 (1H, m), 8.21 (1H, s). |
| Ex. 1-160 | 3-[4-isopropyl-5-(1-phenylcyclopropyl)-4H-1,2,4-triazol-3-yl]benzamide | (400 MHz, DMSO-d6) δ: 1.00 (6H, d, J = 7.2 Hz), 1.47-1.59 (4H, m), 4.51 (1H, q, J = 7.2 Hz), 7.19-7.28 (5H, m), 7.49 (1H, s), 7.59-7.65 (2H, m), 8.02-8.05 (3H, m). |
| Ex. 1-161 | 3-{5-[1-(4-fluorophenyl)cyclopropyl]-4-isopropyl-4H-1,2,4-triazol-3-yl}benzamide | (400 MHz, DMSO-d6) δ: 0.97 (6H, d, J = 7.0 Hz), 1.46-1.58 (4H, m), 4.52 (1H, q, J = 7.2 Hz), 7.13-7.22 (4H, m), 7.49 (1H, s), 7.60-7.63 (2H, m), 7.97-8.08 (3H, m). |
| Ex. 1-162 | 2-(4-chloro-3-[4-methyl-5-(1-phenylcyclopropyl)-4H-1,2,4-triazol-3-yl]phenyl)-1,1,1-trifluoropropan-2-ol | (CDCl3, 400 MHz) δ: 7.75 (d, J = 2.0 Hz, 1H), 7.69 (m, 1H), 7.42 (d, J = 8.6 Hz, 1H), 7.33-7.23 (m, 3H), 7.12 (d, J = 7.1 Hz, 2H), 3.22 (s, 3H), 1.67 (m, 2H), 1.48 (m, 2H). |
| Ex. 2-1 | 1-[4-methyl-5-(1-phenylcyclopropyl)-4H-1,2,4-triazol-3-yl]-4-phenylpiperidine hydrochloride | 300 MHz, DMSO-d6, 1.50-1.66 (4H, m), 1.76-1.91 (4H, m), 2.70-2.80 (1H, m), 3.19-3.28 (2H, m), 3.43 (3H, s), 3.77 (2H, d, J = 12.8 Hz), 7.20-7.39 (10H, m) |
| Ex. 2-2 | methyl 1-[4-methyl-5-(1-phenylcyclopropyl)-4H-1,2,4-triazol-3-yl]-4-phenylpiperidine-4-carboxylate hydrochloride | 400 MHz, DMSO-d6, 1.48-1.60 (4H, m), 2.07-2.15 (2H, m), 2.51-2.55 (5H, m), 3.19 (2H, t, J = 11.6 Hz), 3.57 (2H, brd, J = 13.7 Hz), 3.64 (3H, s), 7.15-7.40 (10H, m) |

-continued

| Examples | Molecular Structure | 1H-NMR |
|---|---|---|
| Ex. 2-3 | 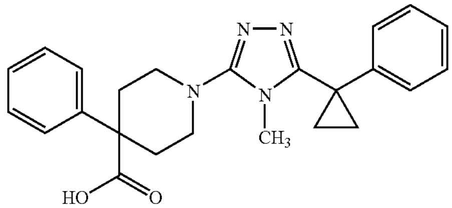 | 400 MHz, DMSO-d6, 1.34-1.48 (4H, m), 1.96-2.06 (2H, m), 2.50 (2H, m), 2.99 (2H, t, J = 11.7 Hz), 3.22 (3H, s), 3.31 (2H, brd, J = 12.5 Hz), 7.03-7.45 (10H, m) |
| Ex. 2-4 | 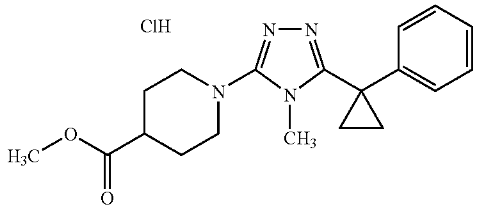 | 400 MHz, DMSO-d6, 1.37-1.50 (4H, m), 1.67-1.77 (2H, m), 1.88-1.93 (2H, m), 2.55-2.62 (1H, m), 2.89-2.95 (2H, m), 3.22 (3H, s), 3.33-3.37 (2H, m), 3.62 (3H, s), 7.04-7.31 (5H, m) |
| Ex. 2-5 | 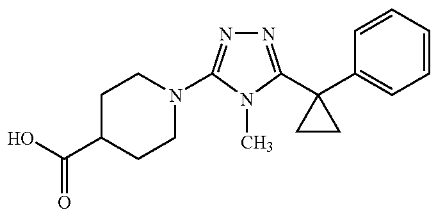 | 400 MHz, DMSO-d6, 1.32-1.46 (4H, m), 1.62-1.75 (2H, m), 1.86-1.91 (2H, m), 2.37-2.46 (1H, m), 2.79-2.88 (2H, m), 3.18 (3H, s), 3.23-3.30 (2H, m), 7.02-7.32 (5H, m), 12.2 (1H, br.s) |
| Ex. 2-6 | 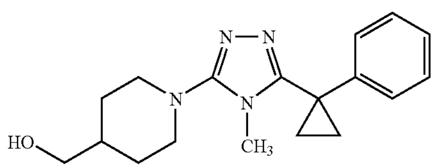 | 400 MHz, DMSO-d6, 1.21-1.57 (7H, m), 1.68-1.75 (2H, m), 2.75 (2H, dt, J = 2.4, 12.0 Hz), 3.17 (3H, s), 3.24-3.37 (4H, m), 4.49 (1H, t, J = 5.2 Hz), 7.00-7.04 (2H, m), 7.16-7.21 (1H, m), 7.26-7.31 (2H, m) |
| Ex. 2-7 | 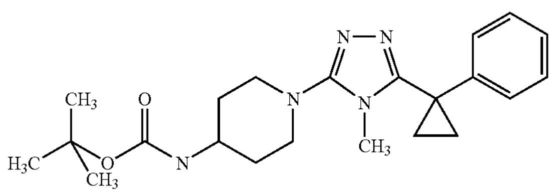 | 400 MHz, DMSO-d6, 1.35-1.64 (14H, m), 1.98-2.05 (2H, m), 2.99-3.07 (2H, m), 3.08 (3H, s), 3.26-3.32 (2H, m), 7.10-7.28 (5H, m) |
| Ex. 2-8 | 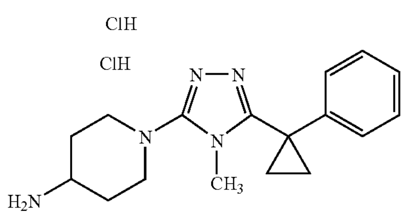 | 400 MHz, DMSO-d6, 1.48-1.62 (4H, m), 1.68-1.79 (2H, m), 1.99-2.07 (2H, m), 3.09-3.18 (2H, m), 3.25-3.38 (4H, m), 3.61-3.68 (2H, m), 7.17-7.36 (5H, m), 8.39 (2H, brs) |
| Ex. 2-9 | 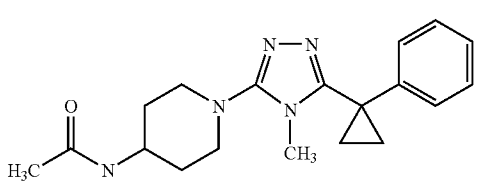 | 300 MHz, DMSO-d6, 1.33-1.60 (6H, m), 1.75-1.85 (5H, m), 2.81-2.91 (2H, m), 3.18 (3H, s), 3.24-3.35 (2H, m), 3.65-3.77 (1H, m), 7.01-7.07 (2H, m), 7.16-7.24 (1H, m), 7.26-7.34 (2H, m), 7.85 (1H, d, J = 7.7 Hz) |

-continued
| Examples | Molecular Structure | 1H-NMR |
|---|---|---|
| Ex. 2-10 | 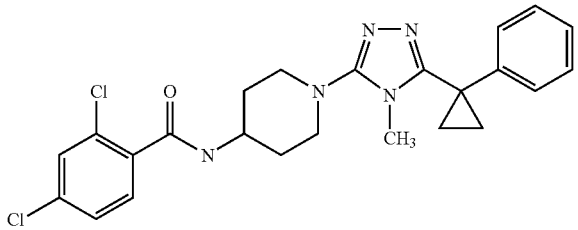 | 300 MHz, DMSO-d6, 1.33-1.46 (4H, m), 1.59-1.73 (2H, m), 1.86-1.97 (2H, m), 2.92 (2H, t, J = 10.6 Hz), 3.19 (3H, s), 3.27-3.37 (2H, m), 3.88-3.97 (1H, m), 7.00-7.68 (8H, m), 8.52 (1H, d, J = 7.7 Hz) |
| Ex. 2-11 | 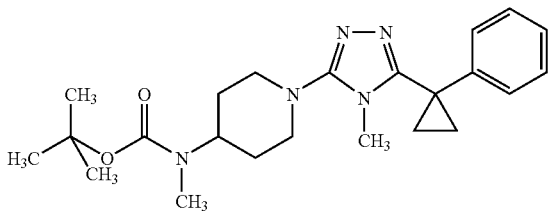 | 300 MHz, DMSO-d6, 1.33-1.47 (14H, m), 1.54-1.64 (2H, m), 1.85 (2H, m), 2.70 (3H, s), 2.85 (2H, m), 3.19 (3H, s), 3.29-3.40 (2H, m), 7.01-7.06 (2H, m), 7.16-7.23 (1H, m), 7.27-7.34 (2H, m) |
| Ex. 2-12 | 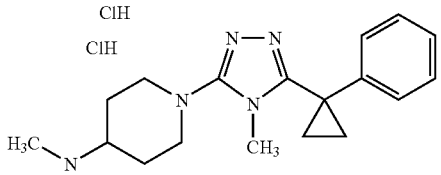 | 400 MHz, DMSO-d6, 1.48-1.64 (4H, m), 1.71-1.83 (2H, m), 2.09-2.18 (2H, m), 2.49-2.53 (3H, m), 3.04-3.27 (3H, m), 3.37 (3H, s), 3.65-3.72 (2H, m), 7.17-7.37 (5H, m), 9.45 (2H, brs) |
| Ex. 2-13 | 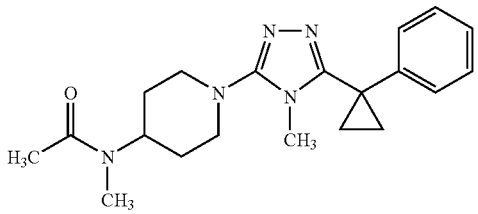 | 300 MHz, DMSO-d6, 120° C., 1.30-1.47 (4H, m), 1.55-1.63 (2H, m), 1.80-1.96 (2H, m), 2.01 (3H, s), 2.79 (3H, s), 2.88-3.00 (2H, m), 3.19 (3H, s), 3.31-3.39 (2H, m), 7.05-7.10 (2H, m), 7.15-7.21 (1H, m), 7.25-7.31 (2H, m), |
| Ex. 2-14 | 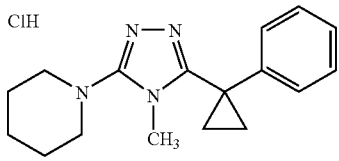 | 300 MHz, DMSO-d6, 1.45-1.71 (10H, m), 3.27-3.41 (7H, m), 7.16-7.39 (5H, m) |
| Ex. 2-15 | 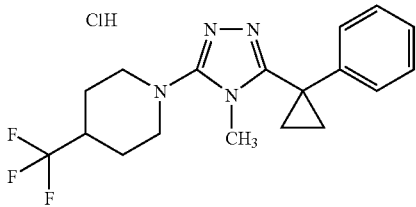 | 300 MHz, DMSO-d6, 1.48-1.73 (6H, m), 1.86-1.96 (2H, m), 2.61-2.73 (1H, m), 3.07-3.18 (2H, m), 3.38 (3H, s), 3.68 (2H, m), 7.18-7.39 (5H, m) |
| Ex. 2-16 | 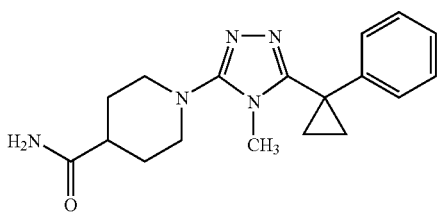 | 400 MHz, DMSO-d6, 1.32-1.46 (4H, m), 1.62-180 (4H, m), 2.21-2.30 (1H, m), 2.72-2.82 (2H, m), 3.17 (3H, s), 3.27-3.31 (2H, m), 6.76 (1H, bs), 7.00-7.05 (2H, m), 7.17-7.20 (1H, m), 7.25-7.31 (3H, m) |

-continued

| Examples | Molecular Structure | 1H-NMR |
|---|---|---|
| Ex. 2-17 | 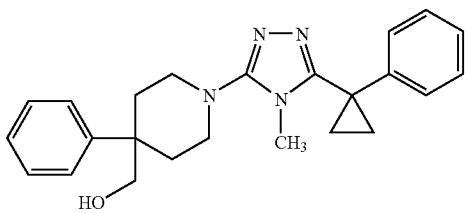 | 300 MHz, DMSO-d6, 1.30-1.45 (4H, m), 1.93-2.22 (4H, m), 2.83 (2H, t, J = 10.1 Hz), 3.09-3.20 (5H, m), 3.38 (2H, d, J = 5.5 Hz), 4.66 (1H, t, J = 5.3 Hz), 6.97-7.04 (2H, m), 7.15-7.43 (3H, m) |
| Ex. 2-18 | 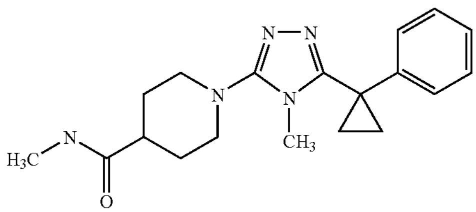 | 300 MHz, DMSO-d6, 1.32-1.46 (4H, m), 1.66-1.77 (4H, m), 2.20-2.31 (1H, m), 2.57 (3H, d, J = 4.8 Hz), 2.72-2.82 (2H, m), 3.18 (3H, s), 3.26-3.34 (2H, m), 7.00-7.06 (2H, m), 7.16-7.23 (1H, m), 7.26-7.33 (2H, m), 7.72 (1H, d, J = 4.4 Hz) |
| Ex. 2-19 | 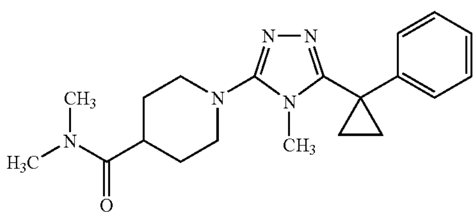 | 300 MHz, DMSO-d6, 1.31-1.47 (4H, m), 1.64-1.75 (4H, m), 2.75-2.92 (6H, m), 3.04 (3H, s), 3.18 (3H, s), 3.26-3.34 (5H, s), 7.01-7.06 (2H, m), 7.16-7.22 (1H, m), 7.26-7.33 (2H, m) |
| Ex. 2-20 | 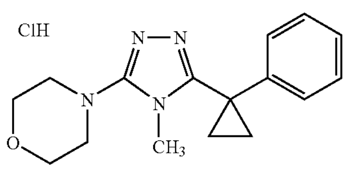 | 300 MHz, DMSO-d6, 1.47-1.64 (4H, m), 3.28-3.35 (4H, m), 3.40 (3H, s), 3.71-3.78 (4H, m), 7.17-7.39 (5H, m) |
| Ex. 2-21 | 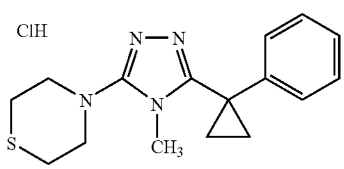 | 300 MHz, DMSO-d6, 1.47-1.63 (4H, m), 2.74-2.81 (4H, m), 3.37 (3H, s), 3.51-3.58 (4H, m), 7.17-7.39 (5H, m) |
| Ex. 2-22 | 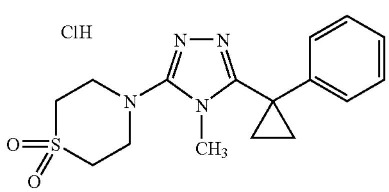 | 300 MHz, DMSO-d6, 1.47-1.65 (4H, m), 3.33-3.44 (7H, m), 3.68-3.76 (4H, m), 7.17-7.39 (5H, m) |
| Ex. 2-23 | 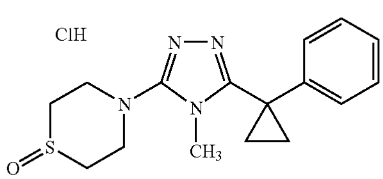 | 300 Hz, DMSO-d6, 1.48-1.65 (4H, m), 2.83-2.93 (2H, m), 3.04-3.16 (2H, m), 3.42 (3H, s), 3.49-3.60 (2H, m), 3.78-3.90 (2H, m), 7.18-7.40 (5H, m) |
| Ex. 2-24 | 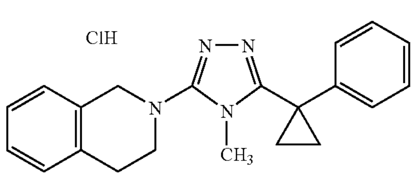 | 400 MHz, DMSO-d6, 1.49-1.63 (4H, m), (2H, t, J = 5.7 Hz), 3.48 (3H, s), 3.66 (2H, t, J = 5.8 Hz), 4.61 (2H, s), 7.15-7.37 (9H, m) |

-continued

| Examples | Molecular Structure | 1H-NMR |
|---|---|---|
| Ex. 2-25 | (ClH) | 300 MHz, DMSO-d6, 1.48-1.72 (4H, m), 1.95-2.05 (2H, m), 2.83 (2H, t, J = 6.4 Hz), 3.19 (3H, s), 3.67 (2H, t, J = 5.5 Hz), 6.49-6.55 (1H, m), 6.86-7.40 (8H, m) |
| Ex. 2-26 | (ClH, ClH) | 400 MHz, DMSO-d6, 1.49-1.64 (4H, m), 3.24 (4H, m), 3.39 (3H, s), 3.53-3.57 (4H, m), 7.18-7.36 (5H, m), 9.70 (1H, brs) |
| Ex. 2-27 | (ClH) | 300 MHz, DMSO-d6, 1.48-1.63 (4H, m), 2.05 (3H, s), 3.24-3.41 (7H, m), 3.57-3.63 (4H, m), 7.17-7.38 (5H, m) |
| Ex. 2-28 | (HCl) | (300 MHz, DMSO-D6), 1.49-1.63 (4H, m), 1.85-1.95 (2H, m), 2.10-2.17 (2H, m), 3.33-3.40 (2H, m), 3.40 (3H, s), 3.52-3.59 (2H, m), 5.35-5.37 (1H, m), 7.19-7.38 (5H, m), 8.20 (1H, d, J = 2.7 Hz), 8.22 (1H, d, J = 2.7 Hz) |
| Ex. 2-29 | (HCl) | (400 MHz, DMSO-D6), 1.49-1.61 (4H, m), 1.85-1.95 (2H, m), 2.08-2.16 (2H, m), 3.16-3.32 (2H, m), 3.32 (3H, s), 3.47-3.55 (2H, m), 5.31-5.33 (1H, m), 7.20-7.23 (2H, m), 7.37-7.40 (2H, m), 8.19 (1H, d, J = 2.4 Hz), 8.22 (1H, d, J = 2.4 Hz) |
| Ex. 2-30 | (HCl) | (400 MHz, DMSO-D6), 1.47-1.62 (4H, m), 1.81-1.91 (2H, m), 2.03-2.13 (2H, m), 3.32-3.40 (2H, m), 3.39 (3H, s), 3.50-3.59 (2H, m), 4.76-4.80 (1H, m), 6.95-7.00 (1H, m), 7.16-7.47 (8H, m) |
| Ex. 2-31 | (HCl) | (300 MHz, DMSO-D6), 1.47-1.62 (4H, m), 1.84-1.95 (2H, m), 2.05-2.21 (2H, m), 3.32-3.43 (2H, m), 3.41 (3H, s), 3.49-3.60 (2H, m), 5.33-5.35 (1H, m), 7.14-7.22 (2H, m), 7.26-7.33 (2H, m), 8.20 (1H, d, J = 2.6 Hz), 8.22 (1H, d, J = 2.6 Hz) |
| Ex. 2-32 | 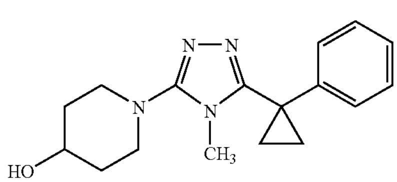 | (300 MHz, CDCl3), 1.35-1.58 (4H, m), 1.63-1.79 (2H, m), 1.97-2.05 (2H, m), 2.96-3.05 (2H, m), 3.20 (3H, s), 3.30-3.37 (2H, m), 3.85-3.91 (1H, m), 7.12-7.31 (5H, m) |

-continued
| Examples | Molecular Structure | 1H-NMR |
|---|---|---|
| Ex. 2-33 | 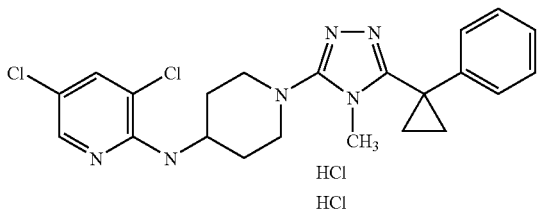 | (400 MHz, DMSO-D6), 1.48-1.67 (4H, m), 1.72-1.85 (2H, m), 1.89-2.00 (2H, m), 3.17-3.27 (2H, m), 3.40 (3H, s), 3.61-3.71 (2H, m), 4.15 (1H, brs), 6.46-6.48 (1H, m), 7.18-7.38 (5H, m), 7.83 (1H, d, J = 1.8 Hz), 8.04 (1H, d, J = 1.8 Hz) |
| Ex. 2-34 | 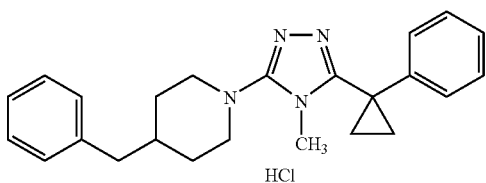 | (400 MHz, DMSO-D6), 1.27-1.83 (9H, m), 2.56 (2H, d, J = 11.4 Hz), 2.95-3.04 (2H, m), 3.34 (3H, s), 3.55-3.62 (2H, m), 7.15-7.35 (5H, m), |
| Ex. 2-35 | 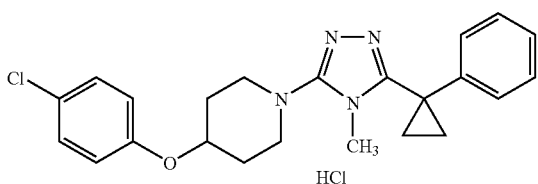 | (300 MHz, DMSO-D6), 1.46-1.63 (4H, m), 1.73-1.87 (2H, m), 2.02-2.14 (2H, m), 3.25-3.37 (2H, m), 3.39 (3H, s), 3.50-3.61 (2H, m), 4.66-4.68 (1H, m), 7.01-7.08 (2H, m), 7.19-7.38 (7H, m) |
| Ex. 2-36 | 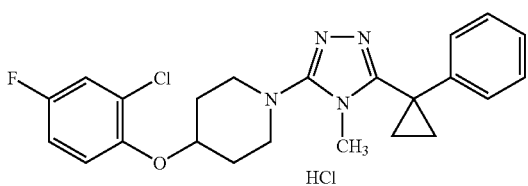 | (300 MHz, DMSO-D6), 1.46-1.62 (4H, m), 1.78-1.91 (2H, m), 2.01-2.13 (2H, m), 3.24-3.36 (2H, m), 3.38 (3H, s), 3.47-3.58 (2H, m), 4.72-4.74 (1H, m), 7.15-7.49 (8H, m) |
| Ex. 2-37 | 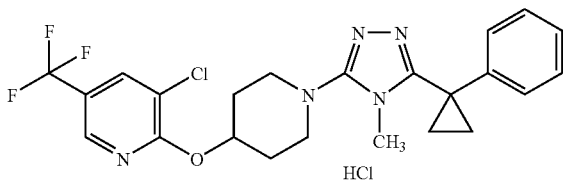 | (400 MHz, DMSO-D6), 1.46-1.67 (4H, m), 1.87-2.03 (2H, m), 2.09-2.22 (2H, m), 3.33-3.46 (2H, m), 3.40 (3H, s), 3.49-3.60 (2H, m), 5.46-5.48 (1H, m), 7.18-7.40 (5H, m), 8.41-8.43 (1H, m), 8.57-8.59 (1H, m) |
| Ex. 2-38 | 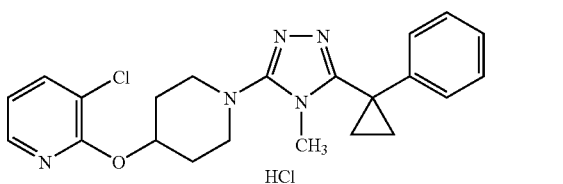 | (300 MHz, DMSO-D6), 1.47-1.63 (4H, m), 1.83-1.97 (2H, m), 2.07-2.18 (2H, m), 3.30-3.42 (2H, m), 3.40 (3H, s), 3.49-3.59 (2H, m), 5.37-5.39 (1H, m), 7.03-7.07 (1H, m), 7.17-7.40 (5H, m), 7.92-7.94 (1H, m), 8.14-8.16 (1H, m) |
| Ex. 2-39 | 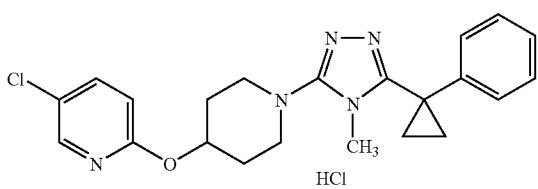 | (300 MHz, DMSO-D6), 1.47-1.63 (4H, m), 1.77-1.92 (2H, m), 2.06-2.19 (2H, m), 3.26-3.41 (2H, m), 3.39 (3H, s), 3.50-3.61 (2H, m), 5.21-5.23 (1H, m), 6.88 (1H, d, J = 9.6 Hz), 7.17-7.39 (5H, m), 7.82 (1H, dd, J = 3 Hz, 8.7 Hz), 8.22 (1H, d, J = 2.4 Hz) |

-continued

| Examples | Molecular Structure | 1H-NMR |
| --- | --- | --- |
| Ex. 2-40 | 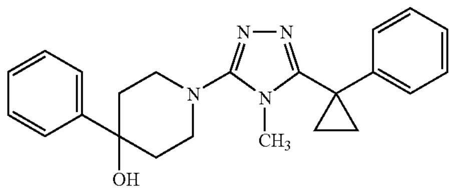 | (300 MHz, DMSO-D6), 1.31-1.50 (4H, m), 1.62-1.73 (2H, m), 2.04-2.18 (2H, m), 3.11-3.35 (4H, m), 3.23 (3H, s), 5.04 (1H, s), 7.03-7.06 (2H, m), 7.17-7.38 (5H, m), 7.49-7.56 (2H, m) |
| Ex. 2-41 | 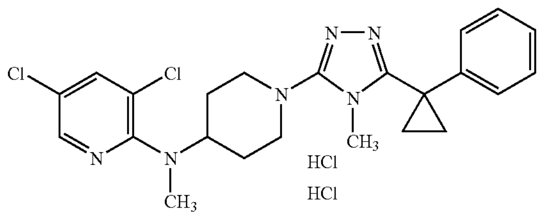 | (300 MHz, DMSO-D6), 1.46-1.66 (4H, m), 1.74-1.86 (2H, m), 1.90-2.07 (2H, m), 2.81 (3H, s), 3.11-3.24 (2H, m), 3.42 (3H, s), 3.67-3.78 (2H, m), 3.87-3.89 (1H, m), 7.19-7.40 (5H, m), 8.02 (1H, d, J = 2.7 Hz), 8.24 (1H, d, J = 2.1 Hz) |
| Ex. 2-42 | 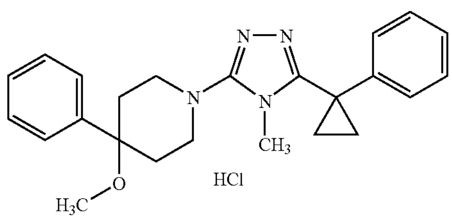 | (300 MHz, DMSO-D6), 1.45-1.64 (4H, m), 2.06-2.13 (4H, m), 2.93 (3H, s), 3.41 (3H, s), 3.43-3.56 (4H, m), 7.16-7.46 (10H, m) |
| Ex. 2-43 | 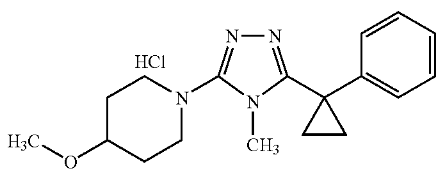 | (300 MHz, DMSO-D6), 1.45-1.70 (6H, m), 1.90-2.01 (2H, m), 3.11-3.23 (2H, m), 3.28 (3H, s), 3.37 (3H, s), 3.40-3.52 (3H, m), 7.15-7.39 (5H, m) |
| Ex. 2-44 | 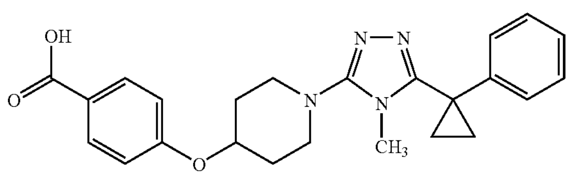 | (300 MHz, DMSO-D6), 1.31-1.49 (4H, m), 1.70-1.88 (2H, m), 2.02-2.15 (2H, m), 2.97-3.08 (2H, m), 3.21 (3H, s), 3.24-3.36 (2H, m), 4.66-4.77 (1H, m), 7.01-7.35 (7H, m), 7.88 (2H, d, J = 9.0 Hz) |
| Ex. 2-45 | 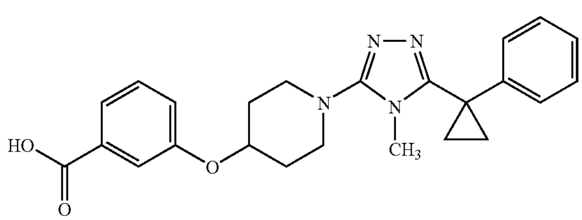 | (300 MHz, DMSO-D6), 1.31-1.49 (4H, m), 1.71-1.87 (2H, m), 2.00-2.12 (2H, m), 2.96-3.15 (2H, m), 3.21 (3H, s), 3.23-3.36 (2H, m), 4.62-4.73 (1H, m), 7.02-7.58 (9H, m) |
| Ex. 2-46 | 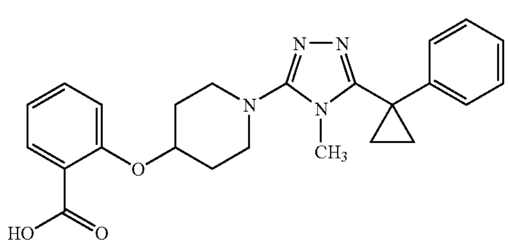 | (300 MHz, DMSO-D6), 1.31-1.48 (4H, m), 1.73-1.89 (2H, m), 1.95-2.09 (2H, m), 2.97-3.07 (2H, m), 3.20 (3H, s), 3.26-3.37 (2H, m), 4.67-4.76 (1H, m), 6.96-7.64 (9H, m) |

| Examples | Molecular Structure | 1H-NMR |
|---|---|---|
| Ex. 2-47 | 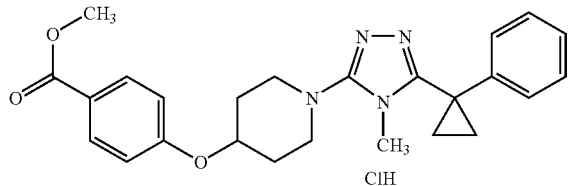 | (300 MHz, DMSO-D6), 1.45-1.65 (4H, m), 1.75-1.90 (2H, m), 2.03-2.18 (2H, m), 3.25-3.58 (4H, m), 3.37 (3H, s), 3.82 (3H, s), 4.76-4.86 (1H, m), 7.10-7.38 (7H, m), 7.92 (2H, d, J = 9.0 Hz) |
| Ex. 2-48 | 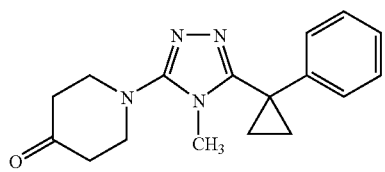 | (300 MHz, CDCl3), 1.38-1.60 (4H, m), 2.64 (4H, J = 6.3 Hz), 3.28 (3H, s), 3.49 (4H, t, J = 6.3 Hz), 7.15-7.32 (5H, m) |
| Ex. 2-49 | 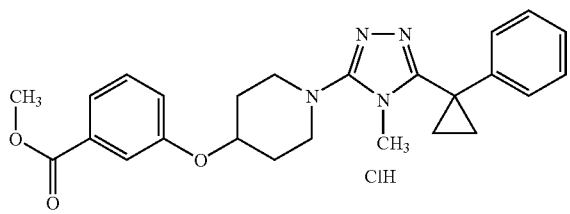 | (300 MHz, DMSO-D6), 1.45-1.61 (4H, m), 1.74-1.89 (2H, m), 2.03-2.16 (2H, m), 3.26-3.59 (4H, m), 3.38 (3H, s), 3.85 (3H, s), 4.72-4.82 (1H, m), 7.15-7.60 (9H, m) |
| Ex. 2-50 | 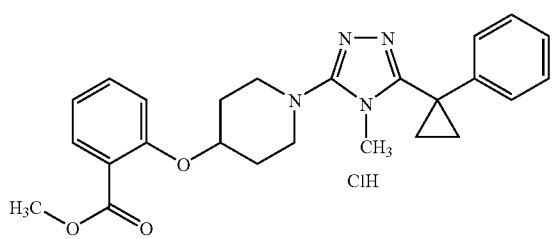 | (300 MHz, DMSO-D6), 1.44-1.64 (4H, m), 1.79-1.94 (2H, m), 1.97-2.12 (2H, m), 3.28-3.41 (2H, m), 3.39 (3H, s), 3.47-3.59 (2H, m), 3.81 (3H, s), 4.81-4.90 (1H, m), 7.00-7.71 (9H, m) |
| Ex. 2-51 | 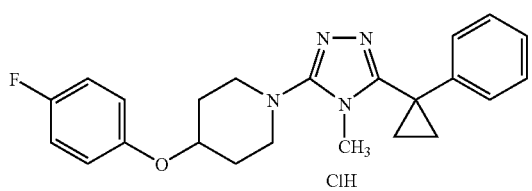 | (400 MHz, DMSO-D6), 1.45-1.65 (4H, m), 1.71-1.85 (2H, m), 2.00-2.11 (2H, m), 3.24-3.33 (2H, m), 3.38 (3H, s), 3.50-3.58 (2H, m), 4.57-4.63 (1H, m), 6.99-7.38 (9H, m) |
| Ex. 2-52 | 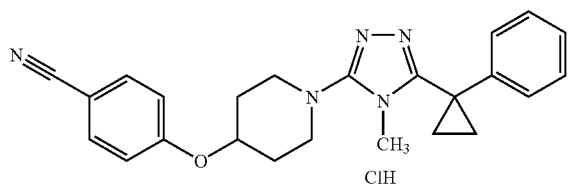 | (400 MHz, DMSO-D6), 1.45-1.62 (4H, m), 1.74-1.88 (2H, m), 2.04-2.17 (2H, m), 3.26-3.34 (2H, m), 3.38 (3H, s), 3.49-3.58 (2H, m), 4.80-4.86 (1H, m), 7.15-7.38 (7H, m), 7.77 (2H, d, J = 8.8 Hz) |
| Ex. 2-53 | 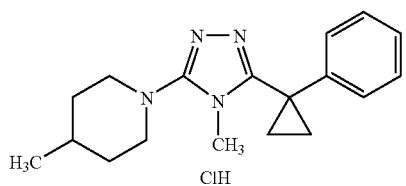 | (300 MHz, DMSO-D6), 0.94 (3H, d, J = 6.6 Hz), 1.15-1.34 (2H, m), 1.47-1.73 (5H, m), 3.02-3.09 (2H, m), 3.37 (3H, s), 3.58-3.63 (2H, m), 7.18-7.37 (5H, m) |

-continued
| Examples | Molecular Structure | 1H-NMR |
|---|---|---|
| Ex. 2-54 | 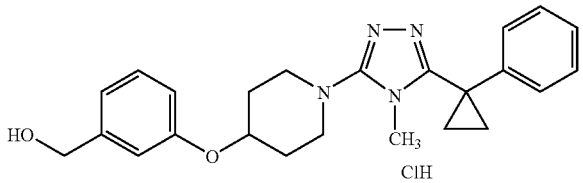 | (300 MHz, DMSO-D6), 1.46-1.64 (4H, m), 1.73-1.89 (2H, m), 2.02-2.14 (2H, m), 3.26-3.36 (2H, m), 3.39 (3H, s), 3.49-3.60 (2H, m), 4.47 (2H, s), 4.62-4.70 (1H, m), 6.83-6.98 (3H, m), 7.17-7.39 (6H, m) |
| Ex. 2-55 | 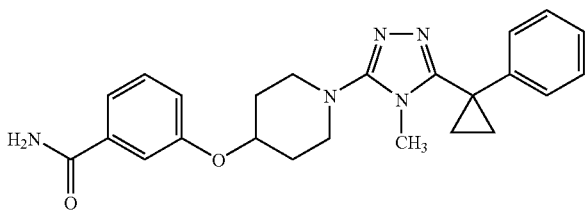 | (300 MHz, CDCl3), 1.32-1.40 (2H, m), 1.54-1.63 (2H, m), 1.87-2.01 (2H, m), 2.04-2.17 (2H, m), 3.04-3.15 (2H, m), 3.22 (3H,s ), 3.34-3.47 (2H, m), 4.54-4.64 (1H, m), 7.07-7.44 (11H, m) |
| Ex. 2-56 | 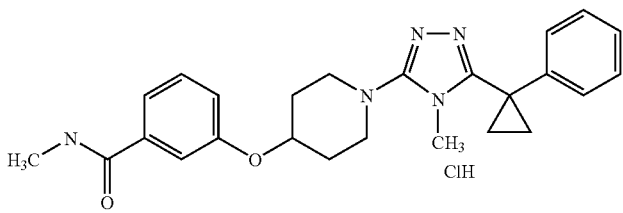 | (300 MHz, DMSO-D6), 1.46-1.64 (4H, m), 1.74-1.89 (2H, m), 2.02-2.17 (2H, m), 2.77 (3H, d, J = 4.5 Hz), 3.25-3.37 (2H, m), 3.40 (3H, s), 3.49-3.62 (2H, m), 4.70-4.79 (1H, m), 7.12-7.47 (9H, m), 8.40-8.47 (1H, m) |
| Ex. 2-57 | 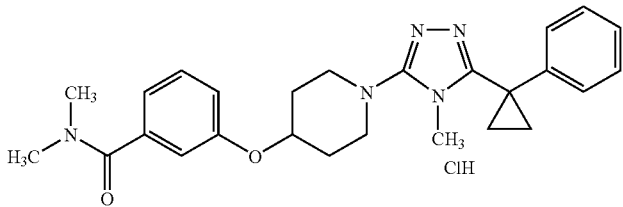 | (300 MHz, DMSO-D6), 1.47-1.66 (4H, m), 1.74-1.88 (2H, m), 2.01-2.16 (2H, m), 2.88-3.00 (6H, m), 3.29-3.39 (2H, m), 3.41 (3H, s), 3.51-3.63 (2H, m), 4.69-4.79 (1H, m), 6.91-7.40 (9H, m) |
| Ex. 2-58 | 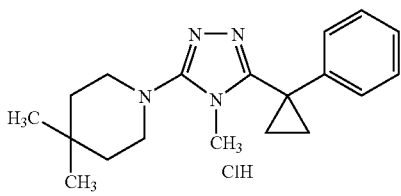 | (300 MHz, DMSO-D6), 0.99 (6H, s), 1.39-1.64 (8H, m), 3.30-3.41 (4H, m), 3.38 (3H, s), 7.16-7.40 (5H, m) |
| Ex. 2-59 | 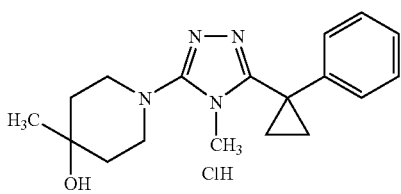 | (300 MHz, DMSO-D6), 1.18 (3H, s), 1.44-1.71 (8H, m), 3.31-3.39 (4H, m, 3.36 (3H, s), 7.14-7.39 (5H, m) |
| Ex. 2-60 | 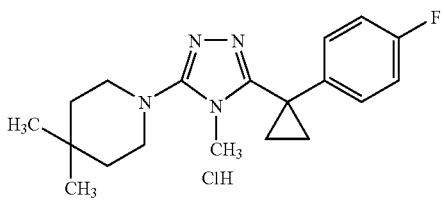 | (300 MHz, DMSO-D6), 0.98 (6H, s), 1.41-1.62 (8H, m), 3.28-3.35 (4H, m), 3.37 (3H, s), 7.13-7.30 (4H, m) |

-continued

| Examples | Molecular Structure | 1H-NMR |
|---|---|---|
| Ex. 2-61 | (structure) | (300 MHz, DMSO-D6), 1.22-1.82 (11H, m), 2.96-3.08 (2H, m), 3.35 (3H, s), 3.47 (2H, t, J = 6.6 Hz), 3.52-3.62 (2H, m), 7.14-7.38 (5H, m) |
| Ex. 2-62 | (structure) | (300 MHz, DMSO-D6), 1.46-1.65 (4H, m), 1.73-1.88 (2H, m), 2.01-2.16 (2H, m), 3.26-3.36 (2H, m), 3.40 (3H, s), 3.49-3.61 (2H, m), 3.86 (3H, s), 4.71-4.79 (1H, m), 7.17-7.51 (8H, m) |
| Ex. 2-63 | (structure) | (300 MHz, DMSO-D6), 1.32-1.49 (4H, m), 1.70-1.85 (2H, m), 2.00-2.10 (2H, m), 2.96-3.08 (2H, m), 3.21 (3H, s), 3.23-3.36 (2H, m), 4.50 (2H, d, J = 6.0 Hz), 4.54-4.64 (1H, m), 5.36 (1H, t, J = 5.7 Hz), 6.88-7.38 (8H, m) |
| Ex. 2-64 | (structure) | (300 MHz, DMSO-D6), 1.31-1.49 (4H, m), 1.69-1.85 (2H, m), 1.97-2.10 (2H, m), 2.97-3.08 (2H, m), 3.20 (3H, s), 3.23-3.34 (2H, m), 4.60-4.71 (1H, m), 7.00-7.48 (8H, m) |
| Ex. 2-65 | (structure) | (300 MHz, DMSO-D6), 0.87 (6H, d, J = 6.9 Hz), 1.26-1.78 (9H, m), 2.96-3.08 (2H, m), 3.37 (3H, s), 3.60-3.71 (2H, m), 7.15-7.40 (5H, m) |
| Ex. 2-66 | (structure) | (300 MHz, DMSO-D6), 1.32-1.48 (4H, m), 1.68-1.84 (2H, m), 1.97-2.10 (2H, m), 2.96-3.07 (2H, m), 3.20 (3H, s), 3.24-3.36 (2H, m), 4.58-4.70 (1H, m), 7.01-7.38 (8H, m), 7.54 (1H, brs), 7.82 (1H, brs) |
| Ex. 2-67 | (structure) | (300 MHz, DMSO-D6), 1.22 (3H, s), 1.45-1.70 (6H, m), 2.01-2.16 (2H, m), 3.07-3.19 (2H, m), 3.37 (3H, s), 3.40-3.51 (2H, m), 3.67 (3H, s), 7.15-7.39 (5H, m) |

-continued

| Examples | Molecular Structure | 1H-NMR |
|---|---|---|
| Ex. 2-68 | (structure) | (400 MHz, DMSO-D6), 0.93 (3H, s), 1.29-1.38 (2H, m), 1.46-1.67 (6H, m), 3.21 (2H, s), 3.22-3.31 (2H, m), 3.34-3.44 (2H, m), 3.36 (3H, s), 7.18-7.34 (5H, m) |
| Ex. 2-69 | (structure) | (400 MHz, DMSO-D6), 1.17 (3H, s), 1.33-1.57 (6H, m), 1.99-2.07 (2H, m), 2.83-2.92 (2H, m), 3.11-3.19 (2H, m), 3.18 (3H, s), 6.99-7.04 (2H, m), 7.17-7.22 (1H, m), 7.25-7.31 (2H, m), 12.36 (1H, brs) |
| Ex. 2-70 | (structure) | (400 MHz, DMSO-D6), 1.12 (3H, s), 1.30-1.54 (6H, m), 1.98-2.12 (2H, m), 2.84-2.93 (2H, m), 3.03-3.10 (2H, m), 3.16 (3H, s), 6.90 (1H, brs), 6.97-7.03 (2H, m), 7.15-7.23 (2H, m), 7.24-7.32 (2H, m) |
| Ex. 2-71 | (structure) | (DMSO-D6) 0.65 (3H, t, J = 7.2 Hz), 1.39-1.63 (6H, m), 1.83-1.95 (2H, m), 2.06-2.19 (2H, m), 3.27-3.37 (2H, m), 3.44-3.55 (2H, m), 3.77 (2H, J = 7.2 Hz), 5.27-5.35 (1H, m), 7.21-7.38 (5H, m), 8.18-8.23 (2H, m) |
| Ex. 2-72 | (structure) | (DMSO-D6) 1.44-1.68 (4H, m), 1.81-1.98 (2H, m), 2.04-2.19 (2H, m), 3.06 (3H, s), 3.24-3.636H, m), 3.44-3.55 (2H, m), 3.77 (2H, t, J = 7.2 Hz), 4.04 (2H, t, J = 5.9 Hz), 5.25-5.38 (1H, m), 7.14-7.42 (5H, m), 8.16-8.27 (2H, m) |
| Ex. 2-73 | (structure) | (DMSO-D6) 1.42-1.63 (4H, m), 1.79-1.92 (2H, m), 2.01-2.16 (2H, m), 3.26-3.41 (5H, m), 3.50-3.68 (2H, m), 4.77-4.83 (1H, m), 7.15-7.42 (7H, m), 7.57-7.62 (1H, m) |
| Ex. 2-74 | (structure) | (DMSO-D6) 1.47-1.59 (2H, m), 1.63-1.77 (2H, m), 2.07-2.18 (2H, m), 3.34-3.45 (2H, m), 3.56-3.67 (4H, m), 3.90-4.00 (2H, m), 5.29-5.38 (1H, m), 7.17-7.39 (5H, m), 8.20-8.27 (2H, m) |

-continued

| Examples | Molecular Structure | 1H-NMR |
|---|---|---|
| Ex. 2-75 | ClH | (DMSO-D6) 1.43-1.66 (4H, m), 1.80-1.94 (2H, m), 2.01-2.17 (2H, m), 3.28-3.40 (2H, m), 3.49-3.59 (2H, m), 4.43-4.57 (2H, m), 5.02-5.18 (2H, m), 5.27-5.36 (1H, m), 5.57-5.71 (1H, m), 7.18-7.19 (5H, m), 8.18-8.26 (2H, m) |
| Ex. 2-76 | ClH | (DMSO-D6) −0.05-0.06 (2H, m), 0.32-0.41 (2H, m), 0.97-1.10 (1H, m), 1.50-1.6684H, m), 1.88-1.96 (2H, m), 2.07-2.19 (2H, m), 3.26-3.40 (2H, m), 3.48-3.57 (2H, m), 3.77 (2H, d, J = 6.0 Hz), 5.26-5.33 (1H, m), 7.21-7.40 (5H, m), 8.16-8.26 (2H, m) |
| Ex. 2-77 | ClH | (DMSO-D6) 0.59 (6H, d, J = 6.7 Hz), 1.48-1.65 (4H, m), 1.79-1.95 (2H, m), 2.00-2.15 (3H, m), 3.23-3.35 (2H, m), 3.38-3.53 (2H, m), 3.66 (2H, d, J = 7.4 Hz), 5.26-5.37 (1H, m), 7.12-7.40 (5H, m), 8.18-8.23 (2H, m) |
| Ex. 2-78 | ClH | (DMSO-D6) 0.88-1.16 (4H, m), 1.46-1.73 (4H, m), 1.83-2.00 (2H, m), 2.08-2.11 (2H, m), 2.60-2.72 (1H, m), 3.20-3.90 (4H, m), 5.29-5.40 (1H, m), 7.21-7.40 (5H, m), 8.19-8.26 (2H, m) |
| Ex. 2-79 | 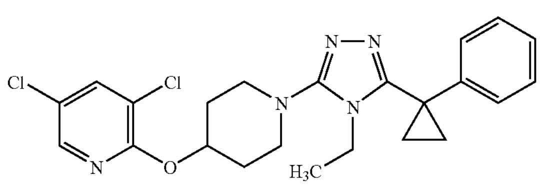 | (DMSO-D6) 1.00 (3H, t, J = 7.2 Hz), 1.33-1.49 (4H, m), 1.79-1.92 (2H, m), 2.03-2.12 (2H, m), 3.22-3.34 (2H, m), 3.66 (2H, J = 7.2 Hz), 5.21-5.30 (1H, m), 7.05-7.33 (5H, m), 8.15-8.23 (2H, m) |
| Ex. 2-80 | ClH | (DMSO-D6) 1.28 (6H, d, J = 5.7 Hz), 1.50-1.66 (4H, m), 1.82-1.97 (2H, m), 2.03-2.18 (2H, m), 3.07-3.19 (2H, m), 3.26-3.38 (2H, m), 4.43 (1H, septet, J = 5.7 Hz), 5.24-5.35 (1H, m), 7.12-7.40 (5H, m), 8.18-8.23 (2H, m) |
| Ex. 2-81 | HCl | 400 MHz, DMSO-d6, 1.67-1.81 (4H, m), 1.83-1.94 (2H, m), 2.05-2.17 (2H, m), 2.19-2.28 (2H, m), 2.41-2.52 (2H, m), 3.12 (3H, s), 3.29-3.39 (2H, m), 3.44-3.55 (2H, m), 5.27-5.29 (1H, m), 7.22-7.33 (3H, m), 7.35-7.42 (2H, m), 2. 19 (1H, d, J = 2.4 Hz), 3. 8.21 (1H, d, J = 2.4 Hz) |

-continued
| Examples | Molecular Structure | 1H-NMR |
|---|---|---|
| Ex. 2-82 | 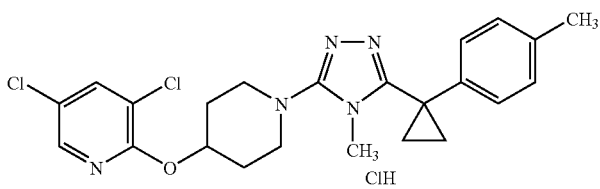 | 8.23 (1H, d, J = 2.4 Hz), 8.20 (1H, d, J = 2.4 Hz), 7.15 (2H, d, J = 8.3 Hz), 7.10 (2H, d, J = 8.3 Hz), 5.33 (1H, m), 3.59-3.48 (2H, m), 3.42-3.31 (2H, m), 3.39 (3H, s), 2.27 (3H, s), 2.18-2.07 (2H, m), 1.96-1.83 (2H, m), 1.61-1.55 (2H, m), 1.48-1.42 (2H, m) |
| Ex. 2-83 | 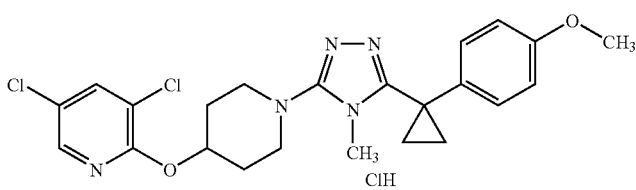 | 8.23 (1H, d, J = 2.5 Hz), 8.20 (1H, d, J = 2.5 Hz), 7.20 (2H, d, J = 8.8 Hz), 6.91 (2H, d, J = 8.8 Hz), 5.34 (1H, m), 3.74 (3H, s), 3.61-3.51 (2H, m), 3.43 (3H, s), 3.42-3.32 (2H, m), 2.19-2.07 (2H, m), 1.96-1.82 (2H, m), 1.61-1.55 (2H, m), 1.47-1.41 (2H, m) |
| Ex. 2-84 | 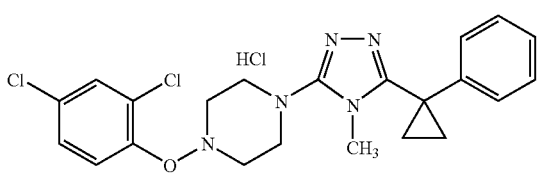 | (300 MHz, DMSO-D6), 1.47-1.63 (4H, m), 3.26-4.55 (8H, m), 3.37 (3H, s), 4.49 (2H, s), 7.11-7.39 (5H, m), 7.59 (1H, dd, J = 8.4, 2.2 Hz), 7.78 (1H, d, J = 2.2 Hz), 8.01 (1H, d, J = 8.4 Hz), 11.8 (1H, brs) |
| Ex. 2-85 | 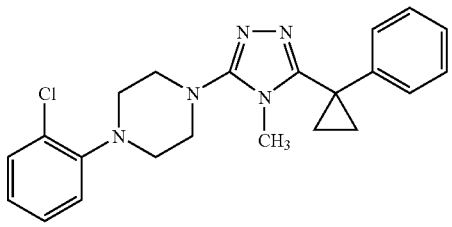 | 400 MHz, DMSO-d6, 1.28-1.53 (4H, m), 3.05-3.16 (4H, m), 3.18-3.28 (4H, m), 3.24 (3H, s), 7.01-7.11 (3H, m), 7.18-7.23 (2H, m), 7.27-7.35 (3H, m), 7.41-7.47 (1H, m) |
| Ex. 2-86 | 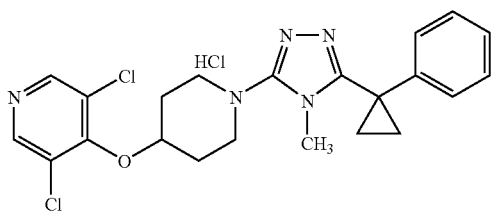 | 400 MHz, DMSO-d6, 1.47-1.68 (4H, m), 1.82-2.20 (4H, m), 3.28-3.39 (2H, m), 3.42 (3H, s), 3.62-3.79 (2H, m), 4.70-4.84 (1H, m), 7.18-7.43 (5H, m), 8.65 (2H, s) |
| Ex. 2-87 | 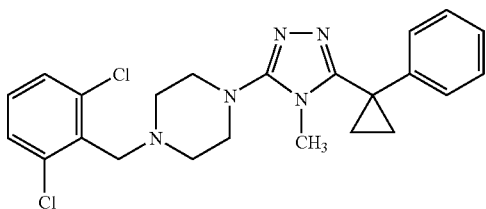 | 400 MHz, DMSO-d6, 1.26-1.48 (4H, m), 2.57-2.67 (4H, m), 2.98-3.05 (4H, m), 3.19 (3H, s), 3.75 (2H, s), 6.98-7.06 (2H, m), 7.17-7.41 (4H, m), 7.46-7.51 (2H, m) |
| Ex. 2-88 | 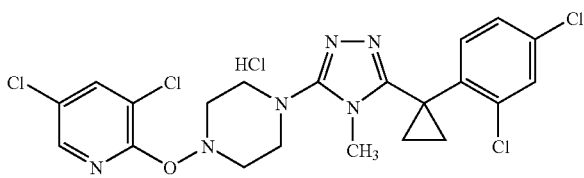 | (300 MHz, DMSO-d6) 1.47 (2H, m), 1.74 (2H, m), 1.81-1.89 (2H, m), 1.99-2.11 (2H, m), 3.23-3.30 (3H, m), 3.40-3.48 (5H, m), 7.49 (1H, dd, J = 8.2, 2.4 Hz), 7.64 (1H, d, J = 1.8 Hz), 7.86 (1H, d, J = 8.5 Hz), 8.21 (2H, dd, J = 8.2, 2.0 Hz) |

-continued
| Examples | Molecular Structure | 1H-NMR |
|---|---|---|
| Ex. 2-89 | 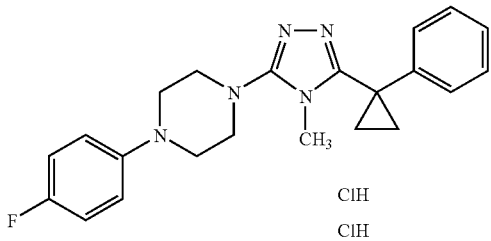 ClH ClH | |
| Ex. 2-90 | 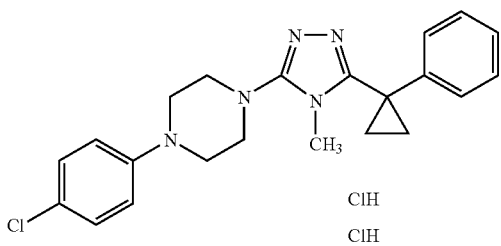 ClH ClH | |
| Ex. 2-91 | 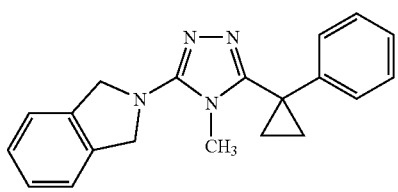 | |
| Ex. 2-92 | 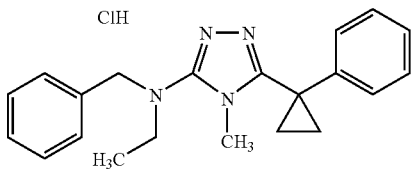 ClH | |
| Ex. 2-93 | 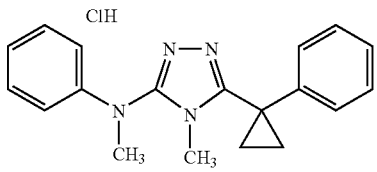 ClH | |
| Ex. 2-94 | 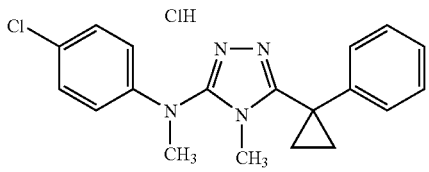 ClH | |
| Ex. 2-95 | 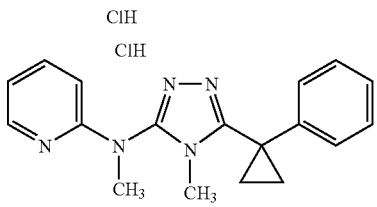 ClH ClH | |

-continued

| Examples | Molecular Structure | 1H-NMR |
|---|---|---|
| Ex. 2-96 | (structure: N-methyl-N-phenyl-4-methyl-5-[1-(4-fluorophenyl)cyclopropyl]-4H-1,2,4-triazol-3-amine, ClH salt) | |
| Ex. 2-97 | (structure: N-phenyl-4-methyl-5-[1-(4-fluorophenyl)cyclopropyl]-4H-1,2,4-triazol-3-amine) | |
| Ex. 2-98 | (structure: N-(carboxymethyl)-N-phenyl triazole derivative, ClH salt) | |
| Ex. 2-99 | (structure: N-(carbamoylmethyl)-N-phenyl triazole derivative) | |

Experimental Example

In Vitro HSD1 (Hydroxysteroid Dehydrogenase 1) Activity Inhibitory Action

The HSD1 inhibitory activity was examined by quantitative determination by an SPA (scintillation proximity assay) system of the suppressive action on the conversion from cortisone to cortisol using human HSD1 (hereinafter recombinant HSD1) expressed using a baculo-virus system as an enzyme source. For the reaction, a reagent was added to a 96 well plate (96 well Opti-plates™-96 (Packard)) to the following final concentration and a volume of 100 μl was reacted at room temperature for 90 min. The reaction solution used was 0.1 μg/ml recombinant HSD1, 500 μM NADPH, 16 nM $^3$H cortisone (Amersham Biosciences, 1.78 Tbq/mol) dissolved in 0.1% BSA (Sigma)-containing PBS and the test drug was 2 μl of a compound solution (dissolved in DMSO). After 90 min, the reaction was stopped by adding PBS (40 μl, containing 0.1% BSA (Sigma)) containing 0.08 μg of anti-cortisol mouse monoclonal antibody (East Coast Biologics), 365 μg SPA PVT mouse antibody-binding beads (Amersham Biosciences) and 175 μM carbenoxolone (Sigma) to the reaction solution. After the completion of the reaction, the plate was incubated overnight at room temperature and the radioactivity was measured by Topcount (Packard). For control, the value (0% inhibition) of the well containing 2 μl of DMSO instead of the test drug was used, and for positive control, the value (100% inhibition) of the well containing carbenoxolone instead of the test drug at the final concentration of 50 μM was used. The inhibition (%) of the test drug was calculated by ((value of control−value of test drug)/(value of control−value of positive control))×100(%). The $IC_{50}$ value was analyzed using a computer-based curve fitting soft. The obtained results are shown in the following Table.

| Examples | hHSD1 $IC_{50}$ |
|---|---|
| Ex. 1-1 | + |
| Ex. 1-2 | ++ |
| Ex. 1-4 | + |
| Ex. 1-5 | ++ |
| Ex. 1-6 | + |
| Ex. 1-7 | + |
| Ex. 1-8 | ++ |
| Ex. 1-10 | + |
| Ex. 1-11 | + |
| Ex. 1-12 | + |
| Ex. 1-13 | ++ |
| Ex. 1-14 | ++ |
| Ex. 1-15 | ++ |
| Ex. 1-16 | + |
| Ex. 1-18 | ++ |
| Ex. 1-19 | ++ |
| Ex. 1-20 | ++ |
| Ex. 1-21 | ++ |
| Ex. 1-22 | ++ |
| Ex. 1-23 | ++ |

-continued

| Examples | hHSD1 IC$_{50}$ |
|---|---|
| Ex. 1-24 | ++ |
| Ex. 1-25 | ++ |
| Ex. 1-26 | ++ |
| Ex. 1-27 | + |
| Ex. 1-28 | ++ |
| Ex. 1-29 | ++ |
| Ex. 1-30 | ++ |
| Ex. 1-31 | ++ |
| Ex. 1-32 | ++ |
| Ex. 1-33 | + |
| Ex. 1-34 | ++ |
| Ex. 1-35 | ++ |
| Ex. 1-36 | ++ |
| Ex. 1-38 | ++ |
| Ex. 1-39 | ++ |
| Ex. 1-40 | + |
| Ex. 1-41 | + |
| Ex. 1-42 | + |
| Ex. 1-43 | + |
| Ex. 1-44 | + |
| Ex. 1-45 | + |
| Ex. 1-46 | + |
| Ex. 1-47 | ++ |
| Ex. 1-48 | + |
| Ex. 1-49 | ++ |
| Ex. 1-50 | ++ |
| Ex. 1-51 | ++ |
| Ex. 1-52 | ++ |
| Ex. 1-53 | ++ |
| Ex. 1-54 | ++ |
| Ex. 1-55 | ++ |
| Ex. 1-56 | ++ |
| Ex. 1-57 | ++ |
| Ex. 1-58 | ++ |
| Ex. 1-59 | + |
| Ex. 1-60 | ++ |
| Ex. 1-61 | + |
| Ex. 1-62 | ++ |
| Ex. 1-63 | ++ |
| Ex. 1-64 | + |
| Ex. 1-65 | ++ |
| Ex. 1-66 | ++ |
| Ex. 1-67 | ++ |
| Ex. 1-68 | ++ |
| Ex. 1-69 | ++ |
| Ex. 1-70 | ++ |
| Ex. 1-71 | ++ |
| Ex. 1-72 | + |
| Ex. 1-73 | ++ |
| Ex. 1-74 | + |
| Ex. 1-75 | ++ |
| Ex. 1-76 | ++ |
| Ex. 1-77 | + |
| Ex. 1-78 | + |
| Ex. 1-79 | + |
| Ex. 1-80 | + |
| Ex. 1-81 | + |
| Ex. 1-82 | ++ |
| Ex. 1-83 | + |
| Ex. 1-84 | + |
| Ex. 1-85 | + |
| Ex. 1-87 | + |
| Ex. 1-88 | + |
| Ex. 1-89 | ++ |
| Ex. 1-90 | ++ |
| Ex. 1-91 | ++ |
| Ex. 1-92 | ++ |
| Ex. 1-93 | ++ |
| Ex. 1-94 | + |
| Ex. 1-95 | ++ |
| Ex. 1-96 | ++ |
| Ex. 1-97 | + |
| Ex. 1-98 | + |
| Ex. 1-99 | + |
| Ex. 1-100 | ++ |
| Ex. 1-101 | ++ |
| Ex. 1-102 | ++ |

-continued

| Examples | hHSD1 IC$_{50}$ |
|---|---|
| Ex. 1-103 | ++ |
| Ex. 1-104 | + |
| Ex. 1-105 | ++ |
| Ex. 1-106 | ++ |
| Ex. 1-107 | ++ |
| Ex. 1-108 | ++ |
| Ex. 1-109 | ++ |
| Ex. 1-110 | ++ |
| Ex. 1-111 | + |
| Ex. 1-112 | ++ |
| Ex. 1-113 | ++ |
| Ex. 1-114 | ++ |
| Ex. 1-115 | ++ |
| Ex. 1-116 | ++ |
| Ex. 1-117 | ++ |
| Ex. 1-118 | ++ |
| Ex. 1-119 | ++ |
| Ex. 1-120 | ++ |
| Ex. 1-121 | ++ |
| Ex. 1-122 | ++ |
| Ex. 1-123 | ++ |
| Ex. 1-124 | + |
| Ex. 1-125 | ++ |
| Ex. 1-126 | + |
| Ex. 1-127 | ++ |
| Ex. 1-128 | ++ |
| Ex. 1-129 | ++ |
| Ex. 1-130 | + |
| Ex. 1-131 | ++ |
| Ex. 1-132 | ++ |
| Ex. 1-134 | ++ |
| Ex. 1-137 | ++ |
| Ex. 1-144 | ++ |
| Ex. 1-145 | ++ |
| Ex. 1-149 | ++ |
| Ex. 1-150 | ++ |
| Ex. 1-152 | ++ |
| Ex. 1-153 | ++ |
| Ex. 1-154 | ++ |
| Ex. 1-158 | ++ |
| Ex. 1-159 | ++ |
| Ex. 1-160 | ++ |
| Ex. 1-161 | ++ |
| Ex. 2-1 | ++ |
| Ex. 2-2 | + |
| Ex. 2-4 | + |
| Ex. 2-5 | + |
| Ex. 2-6 | ++ |
| Ex. 2-7 | + |
| Ex. 2-8 | + |
| Ex. 2-9 | + |
| Ex. 2-10 | + |
| Ex. 2-11 | + |
| Ex. 2-12 | + |
| Ex. 2-13 | + |
| Ex. 2-14 | ++ |
| Ex. 2-15 | ++ |
| Ex. 2-16 | ++ |
| Ex. 2-17 | + |
| Ex. 2-18 | + |
| Ex. 2-19 | + |
| Ex. 2-20 | ++ |
| Ex. 2-21 | ++ |
| Ex. 2-22 | + |
| Ex. 2-23 | + |
| Ex. 2-24 | ++ |
| Ex. 2-25 | ++ |
| Ex. 2-26 | + |
| Ex. 2-27 | + |
| Ex. 2-28 | ++ |
| Ex. 2-29 | + |
| Ex. 2-30 | ++ |
| Ex. 2-31 | ++ |
| Ex. 2-32 | ++ |
| Ex. 2-33 | + |
| Ex. 2-34 | + |
| Ex. 2-35 | ++ |

| Examples | hHSD1 IC$_{50}$ |
|---|---|
| Ex. 2-36 | ++ |
| Ex. 2-37 | + |
| Ex. 2-38 | ++ |
| Ex. 2-39 | ++ |
| Ex. 2-40 | + |
| Ex. 2-41 | + |
| Ex. 2-42 | + |
| Ex. 2-43 | + |
| Ex. 2-44 | + |
| Ex. 2-45 | + |
| Ex. 2-46 | + |
| Ex. 2-47 | + |
| Ex. 2-48 | ++ |
| Ex. 2-49 | ++ |
| Ex. 2-50 | + |
| Ex. 2-51 | ++ |
| Ex. 2-52 | ++ |
| Ex. 2-53 | ++ |
| Ex. 2-54 | + |
| Ex. 2-55 | + |
| Ex. 2-56 | + |
| Ex. 2-57 | + |
| Ex. 2-58 | ++ |
| Ex. 2-59 | ++ |
| Ex. 2-60 | ++ |
| Ex. 2-61 | ++ |
| Ex. 2-62 | + |
| Ex. 2-63 | + |
| Ex. 2-64 | + |
| Ex. 2-65 | ++ |
| Ex. 2-66 | + |
| Ex. 2-67 | ++ |
| Ex. 2-68 | ++ |
| Ex. 2-69 | + |
| Ex. 2-70 | ++ |
| Ex. 2-71 | + |
| Ex. 2-72 | + |
| Ex. 2-73 | ++ |
| Ex. 2-74 | + |
| Ex. 2-75 | ++ |
| Ex. 2-76 | ++ |
| Ex. 2-77 | + |
| Ex. 2-78 | ++ |
| Ex. 2-79 | ++ |
| Ex. 2-80 | ++ |
| Ex. 2-81 | ++ |
| Ex. 2-82 | + |
| Ex. 2-83 | + |
| Ex. 2-84 | + |
| Ex. 2-85 | ++ |
| Ex. 2-86 | + |
| Ex. 2-87 | + |
| Ex. 2-88 | + |
| Ex. 2-89 | + |
| Ex. 2-90 | + |
| Ex. 2-91 | ++ |
| Ex. 2-92 | ++ |
| Ex. 2-93 | ++ |
| Ex. 2-94 | ++ |
| Ex. 2-95 | ++ |
| Ex. 2-96 | ++ |

In the above Table, "+" in the column of IC$_{50}$ means 10 nM≦IC$_{50}$<1,000 nM and "++" in the column of IC$_{50}$ means IC$_{50}$<10 nM.

In the same manner as in Example 1-1 or 2-1, and using other conventional methods as necessary, the triazole compounds shown in the following Table can be also produced.

| Compound No. | Molecular Structure | R |
|---|---|---|
| 1-1001 | (structure) | |
| 1-1002 | (structure) | |
| 1-1003 | (structure) | |
| 1-1004 | (structure) | |

-continued
| Compound No. | Molecular Structure | R |
|---|---|---|
| 1-1005 | 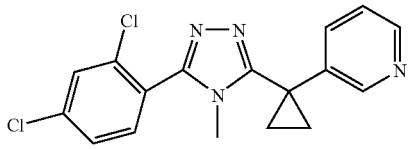 | |
| 1-1006 | 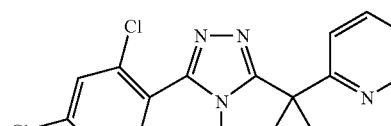 | |
| 1-1007 | 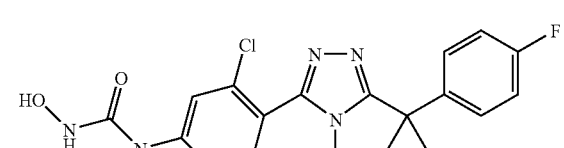 | |
| 1-1008 | 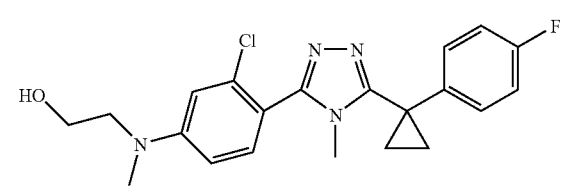 | |
| 1-1009 | 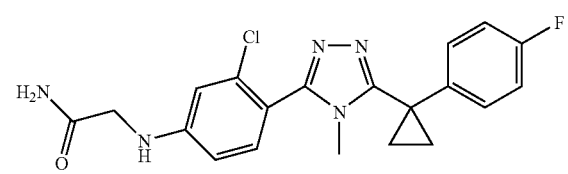 | |
| 1-1010 | 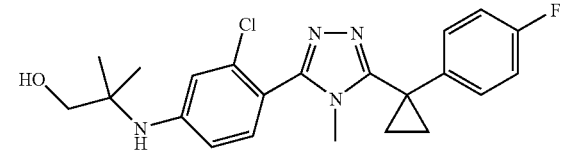 | |
| 1-1011 | 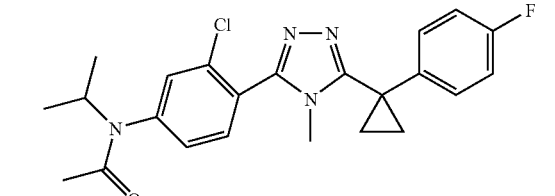 | |
| 1-1012 | 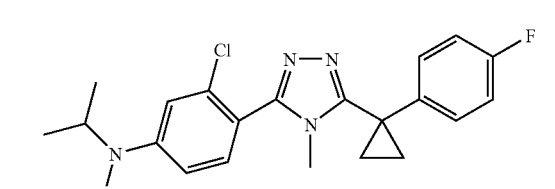 | |

| Compound No. | Molecular Structure | R |
|---|---|---|
| 1-1013 | 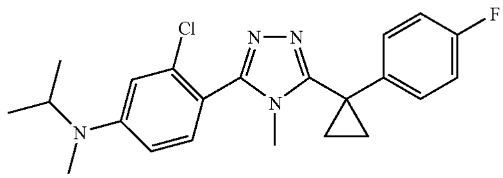 | |
| 1-1014 | 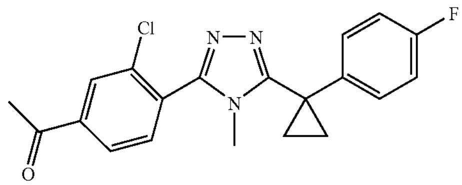 | |
| 1-1015 | 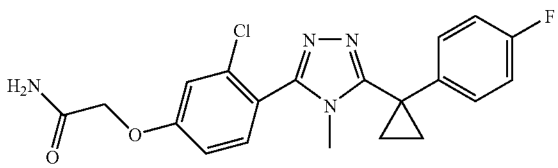 | |
| 1-1016 | 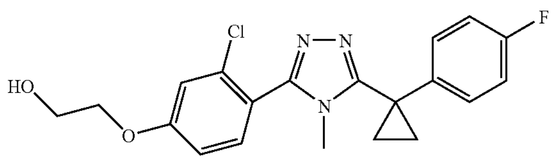 | |
| 1-1017 | 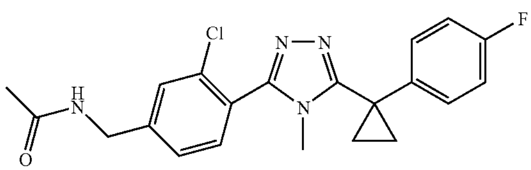 | |
| 1-1018 | 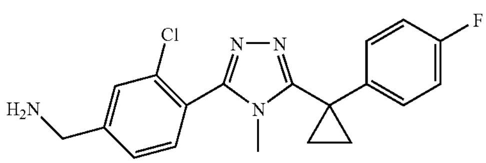 | |
| 1-1019 | 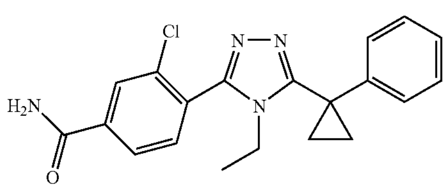 | |
| 1-1020 | 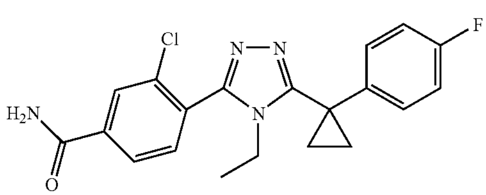 | |

-continued
| Compound No. | Molecular Structure | R |
|---|---|---|
| 1-1021 | 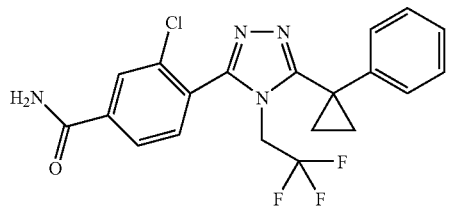 | |
| 1-1022 | 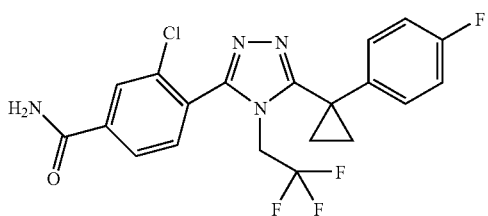 | |
| 1-1023 | 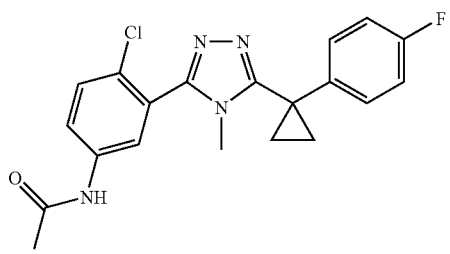 | |
| 1-1024 | 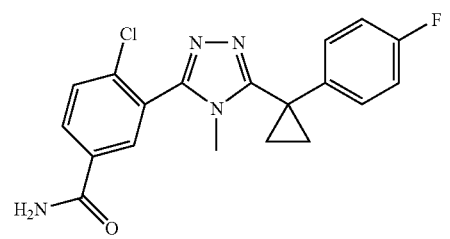 | |
| 1-1025 | 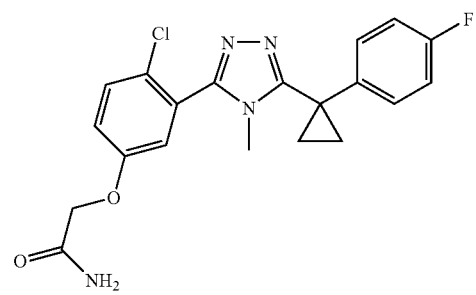 | |
| 1-1026 | 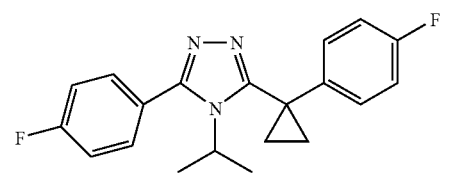 | |

-continued
| Compound No. | Molecular Structure | R |
|---|---|---|
| 1-1027 | 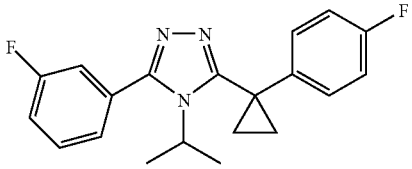 | |
| 1-1028 | 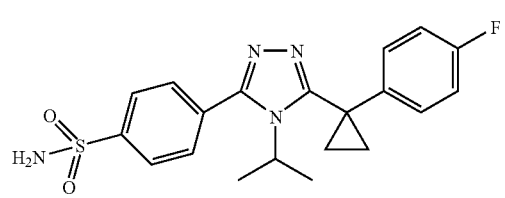 | |
| 1-1029 | 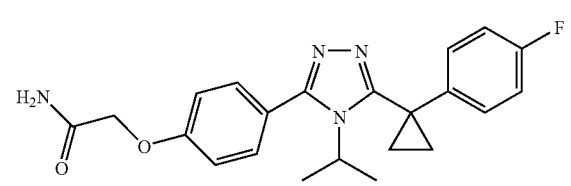 | |
| 1-1030 | 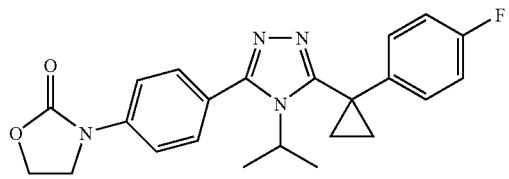 | |
| 1-1031 | 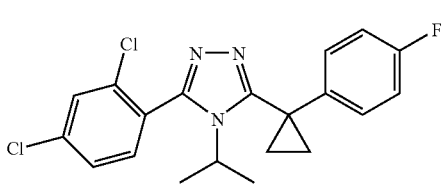 | |
| 1-1032 | 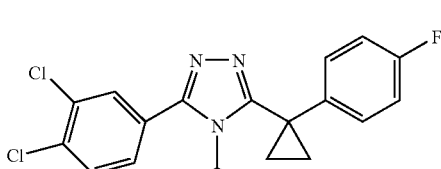 | |
| 1-1033 | 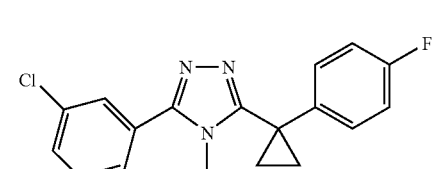 | |
| 1-1034 | 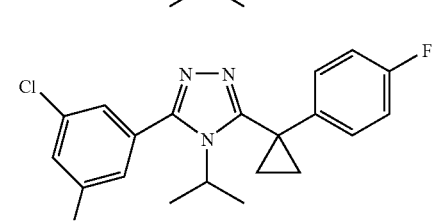 | |

-continued

| Compound No. | Molecular Structure | R |
|---|---|---|
| 2-1001 | 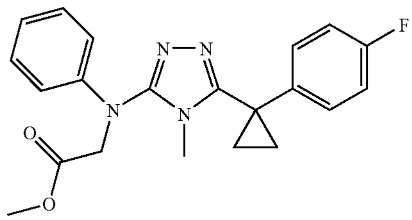 | |
| 2-1002 | 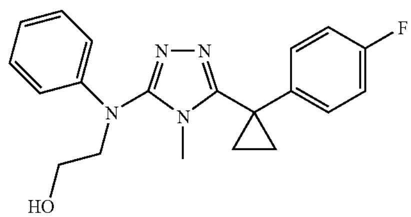 | |
| 2-1003 | 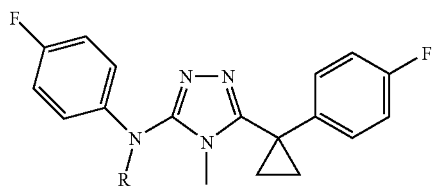 | H |
| 2-1004 | 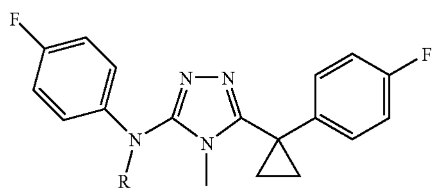 | —CH$_3$ |
| 2-1005 | 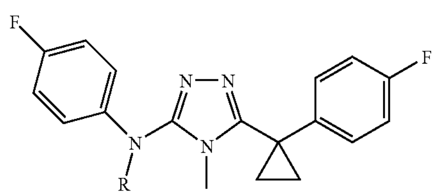 | *—CH$_2$CO$_2$H |
| 2-1006 | 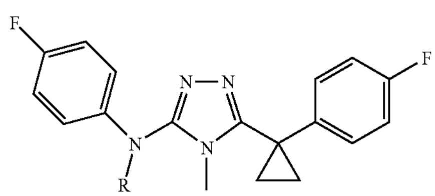 | *—CH$_2$CO$_2$CH$_3$ |
| 2-1007 | 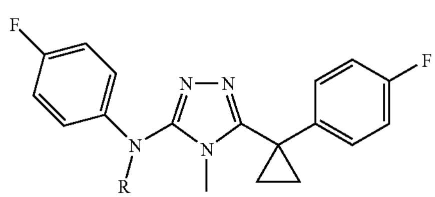 | *—CH$_2$CONH$_2$ |

-continued

| Compound No. | Molecular Structure | R |
|---|---|---|
| 2-1008 | 4-fluorophenyl-N(R)-[4-methyl-5-[1-(4-fluorophenyl)cyclopropyl]-4H-1,2,4-triazol-3-yl]amine | *⁓⁓OH |
| 2-1009 | pyridin-2-yl-N(R)-[4-methyl-5-[1-(4-fluorophenyl)cyclopropyl]-4H-1,2,4-triazol-3-yl]amine | H |
| 2-1010 | pyridin-2-yl-N(R)-[4-methyl-5-[1-(4-fluorophenyl)cyclopropyl]-4H-1,2,4-triazol-3-yl]amine | —CH₃ |
| 2-1011 | pyridin-2-yl-N(R)-[4-methyl-5-[1-(4-fluorophenyl)cyclopropyl]-4H-1,2,4-triazol-3-yl]amine | *⁓CO₂H |
| 2-1012 | pyridin-2-yl-N(R)-[4-methyl-5-[1-(4-fluorophenyl)cyclopropyl]-4H-1,2,4-triazol-3-yl]amine | *⁓CO₂CH₃ |
| 2-1013 | pyridin-2-yl-N(R)-[4-methyl-5-[1-(4-fluorophenyl)cyclopropyl]-4H-1,2,4-triazol-3-yl]amine | *⁓CONH₂ |
| 2-1014 | pyridin-2-yl-N(R)-[4-methyl-5-[1-(4-fluorophenyl)cyclopropyl]-4H-1,2,4-triazol-3-yl]amine | *⁓⁓OH |
| 2-1015 | pyridin-3-yl-N(R)-[4-methyl-5-[1-(4-fluorophenyl)cyclopropyl]-4H-1,2,4-triazol-3-yl]amine | H |
| 2-1016 | pyridin-3-yl-N(R)-[4-methyl-5-[1-(4-fluorophenyl)cyclopropyl]-4H-1,2,4-triazol-3-yl]amine | —CH₃ |

| Compound No. | Molecular Structure | R |
|---|---|---|
| 2-1017 | 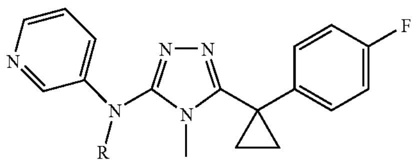 | *⁓CO₂H → *\~CO$_2$H |
| 2-1018 | 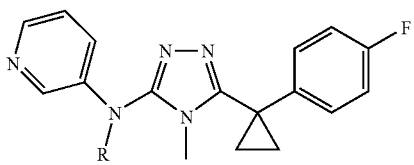 | *\~CO$_2$CH$_3$ |
| 2-1019 | 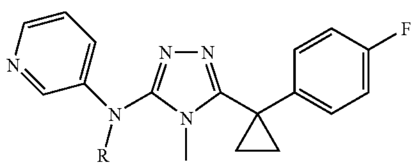 | *\~CONH$_2$ |
| 2-1020 | 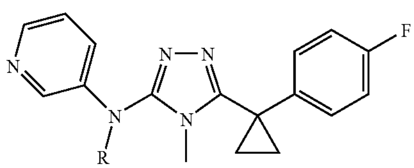 | *\~\~OH |

As mentioned above, the triazole compound of the present invention has superior HSD1 inhibitory activity and is useful as an HSD1 inhibitor, a therapeutic drug of diabetes or a therapeutic drug of obesity.

What is claimed is:

1. A triazole compound represented by the following formula:

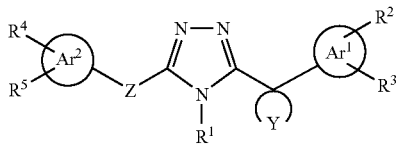

wherein $R^1$ is an alkyl group or a cycloalkyl group wherein the alkyl group and the cycloalkyl group are optionally substituted by 1 to 5 substituents each independently selected from a halogen atom, —CF$_3$, —OH, —NH$_2$, an alkoxy group, a cycloalkyl group, an alkenyl group, —COOH, —CO—O-alkyl, —CO—N($R^7$)($R^8$), —N($R^7$)—CO—$R^8$, an aryl group and a heteroaryl group wherein $R^7$ and $R^8$ are each independently a hydrogen atom or an alkyl group, and the aryl group and the heteroaryl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group and a heteroaryl group wherein n is 0-3, $R^9$ and $R^{10}$ are each independently a hydrogen atom, an alkyl group or —CO-alkyl, and $R^{11}$ is —OH, an alkoxy group, an alkyl group or —N($R^{12}$)($R^{13}$) wherein $R^{12}$ and $R^{13}$ are each independently a hydrogen atom or an alkyl group;

Y is a cycloalkyl group or a heterocycloalkyl group wherein the cycloalkyl group and the heterocycloalkyl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group and a heteroaryl group (n, $R^9$, $R^{10}$ and $R^{11}$ are as defined above);

$Ar^1$ is an aryl group or a heteroaryl group;

$R^2$ and $R^3$ are each independently a hydrogen atom, a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group or a heteroaryl group wherein the aryl group and the heteroaryl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group and a heteroaryl group (n, $R^9$, $R^{10}$ and $R^{11}$ are as defined above);

Z is —(CH($R^{14}$))$_p$—, —(CH($R^{14}$))$_p$—N($R^{16}$)—CH($R^{15}$))$_q$— or

wherein $Y_1$ is a cycloalkyl group or a heterocycloalkyl group wherein the cycloalkyl group and the heterocycloalkyl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group and a heteroaryl group (n, $R^9$, $R^{10}$ and $R^{11}$ are as defined above), p is 0-3, q is 0-3, $R^{14}$ and $R^{15}$ are each independently a hydrogen atom, a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group or a heteroaryl group wherein the aryl group and the heteroaryl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group and a heteroaryl group (n, $R^9$, $R^{10}$ and $R^1$ are as defined above), and $R^{16}$ is a hydrogen atom, a haloalkyl group, an alkyl group, —(CH$_2$)$_n$—OH, —(CH$_2$)$_n$—CO—$R^{11}$, a cycloalkyl group, an alkenyl group, an aryl group or a heteroaryl group wherein the aryl group and the heteroaryl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group and a heteroaryl group (n, $R^9$, $R^{10}$ and $R^{11}$ are as defined above);

$Ar^2$ is an aryl group or a heteroaryl group; or

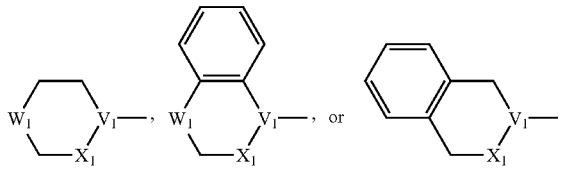

wherein $X_1$ is —(CH$_2$)$_t$— wherein t is 0-2, $V_1$ is =CH— or =N—, and $W_1$ is —C($R^{17}$)($R^{18}$)—, —O—, —S—, —SO$_2$—, —SO—, —CO— or —N($R^{19}$)— wherein $R^{17}$ and $R^{18}$ are each independently a hydrogen atom, an alkyl group, an alkoxy group, a haloalkyl group, —(CH2)$_r$—OH, —CO—$R^{20}$, —N($R^{21}$)($R^{22}$) or —L$_1$—Ar$^3$ wherein r is 0-3, $R^{20}$ is —OH, an alkoxy group, an alkoxyalkyl group or —N($R^{23}$)($R^{24}$)

wherein $R^{23}$ and $R^{24}$ are each independently a hydrogen atom, an alkyl group, —(CH$_2$)$_s$—OH, an alkoxyalkyl group, or in combination form

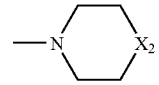

wherein s is 0-3, $X_2$ is —O—, —(CH$_2$)$_t$— or —N($R^{25}$)— wherein t is as defined above and $R^{25}$ is a hydrogen atom, —CO—$R^{26}$, —SO$_2$—$R^{26}$ or —(CH$_2$)$_u$—Ar$^4$ wherein $R^{26}$ is an alkyl group, an alkoxy group, —NH-alkyl or —N(-alkyl)$_2$, u is 0-3, and Ar$^4$ is an aryl group or a heteroaryl group wherein the aryl group and the heteroaryl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group and a heteroaryl group (n, $R^9$, $R^{10}$ and $R^{11}$ are as defined above), $L_1$ is —(CH$_2$)$_v$—, —O— or —CO— wherein v is 0-3, and

Ar$^3$ is an aryl group or a heteroaryl group wherein the aryl group and the heteroaryl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$ an aryl group and a heteroaryl group (n, $R^9$, $R^{10}$ and $R^{11}$ are as defined above), and $R^{21}$ and $R^{22}$ are each independently a hydrogen atom, an alkyl group, —CO-alkyl, —CO—O-alkyl or —L$_1$,—Ar$^3$(L$_1$ and Ar$^3$ are as defined above), and $R^{19}$ is a hydrogen atom, —Co—$R^{26}$, —SO$_2$—$R^{26}$ or —(CH$_2$)$_u$—Ar$^4$ ($R^{26}$, u and Ar$^4$ are as defined above); and $R^4$ and $R^5$ are each independently a hydrogen atom, a halogen atom, —OH, —NO$_2$, —CN, an alkyl group, an alkoxy group, —CO—$R^{27}$, —SO$_{02}$—$R^{27}$, —CO—N($R^{28}$)($R^{29}$) or —N($R^{30}$)($R^{31}$)

wherein the alkyl group and the alkoxy group are optionally substituted by 1 to 5 substituents each independently selected from a halogen atom, —CF$_3$, —OH, an alkoxy group, a haloalkoxy group, —N($R^9$)($R^{10}$), —CN, —NO$_2$, a cycloalkyl group, an alkenyl group, —CO—$R^{11}$, an aryl group and a heteroaryl group ($R^9$, $R^{10}$ and $R^{11}$ are as defined above), wherein the aryl group and the heteroaryl group are optionally substituted by 1 to 3 substituents each independently selected from a halogen atom, a haloalkyl group, an alkyl group, —(CH$_2$)$_n$—OH, —N($R^9$)($R^{10}$), —CN, —NO$_2$, an alkoxy group, a cycloalkyl group, an alkenyl group, —CO—$R^{11}$, an aryl group and a heteroaryl group (n, $R^9$, $R^{10}$ and $R^{11}$ are as defined above)

$R^{27}$ is —OH, an alkoxy group, an alkyl group, —NH$_2$, —NH-alkyl or —N(-alkyl)$^2$, $R^{28}$ and $R^{29}$ are each independently a hydrogen atom, an alkyl group or —(CH$_2$)$_w$—$R^{32}$, wherein w is 0-3 and $R^{32}$ is —OH, —CF$_3$, an alkoxy group, —CONH$_2$ or —N($R^{33}$)($R^{34}$)

wherein $R^{33}$ and $R^{34}$ are each independently a hydrogen atom, an alkyl group, —CO-alkyl, or in combination form

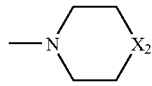

($X_2$ is as defined above)
or $R^{28}$ and $R^{29}$ in combination form

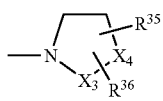

wherein $X_3$ is —CO—, —$CH_2$— or —$CH_2$—$CH_2$—, $X_4$ is —O—, —$(CH_2)_t$—, —$N(R^{25})$— or

wherein $Y_2$ is cycloalkyl or heterocycloalkyl and t and $R^{25}$ are as defined above, and $R^{35}$ and $R^{36}$ are each independently a hydrogen atom, a halogen atom, an alkyl group optionally substituted by —OH, —OH, —CN, —$NO_2$, an alkoxy group, a cycloalkyl group, an alkenyl group, —CO—$R^{37}$, —$N(R^{38})(R^{39})$
wherein $R^{37}$ is —OH, an alkoxy group, —$NH_2$, —NH-alkyl, —N(-alkyl)$_2$ or

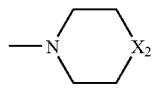

($X_2$ is as defined above)
wherein the alkyl group in —NH-alkyl and —N(-alkyl)$_2$ and the alkoxy group are optionally substituted by 1 to 5 substituents each independently selected from a halogen atom, —$CF_3$, —OH, an alkoxy group, a haloalkoxy group, —$N(R^9)(R^{10})$, —CN, —$NO_2$, a cycloalkyl group, an alkenyl group, —CO—$R^{11}$ an aryl group and a heteroaryl group ($R^9$, $R^{10}$ and $R^{11}$ are as defined above),
wherein the aryl group and the heteroaryl group are optionally substituted by 1 to 3 substituents each independently selected from a halogen atom, a haloalkyl group, an alkyl group, —$(CH_2)_n$—OH, —$N(R^9)(R^{10})$, —CN, —$NO_2$, an alkoxy group, a cycloalkyl group, an alkenyl group, —CO—$R^{11}$, an aryl group and a heteroaryl group (n, $R^9$, $R^{10}$ and $R^{11}$ are as defined above), and
$R^{38}$ and $R^{39}$ are each independently a hydrogen atom, an alkyl group, —CO-alkyl or —CO—O—alkyl, and
$R^{30}$ and $R^{31}$ are each independently a hydrogen atom, an alkyl group optionally substituted by —OH, —$SO_2$—$R^{40}$, —$(CH_2)_x$—CO—$R^{41}$ or

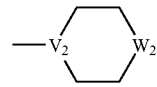

wherein x is 0-3, $R^{40}$ is an alkyl group or —$NH_2$, $R^{41}$ is a hydrogen atom, an alkyl group optionally substituted by —OH, —OH, an alkoxy group, an alkoxyalkyl group or —$(CH_2)_s$—$N(R^{42})(R^{43})$
wherein s is as defined above and $R^{42}$ and $R^{43}$ are each independently a hydrogen atom, an alkyl group, —OH, an alkoxy group, or in combination form

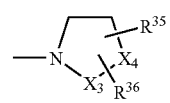

($X_3$, $X_4$, $R^{35}$ and $R^{36}$ are as defined above),
$V_2$ is =CH— or =N— and $W_2$ is —$C(R^{44})(R^{45})$—, —O— or —$N(R^{46})$—
wherein $R^{44}$ and $R^{45}$ are each independently a hydrogen atom, an alkyl group, an alkoxy group, a haloalkyl group, —$(CH_2)_r$—OH, —CO—$R^{47}$ or —$N(R^{48})(R^{49})$
wherein r is as defined above, $R^{47}$ is —OH, an alkoxy group, an alkoxyalkyl group, —$N(R^{50})(R^{51})$
wherein $R^{50}$ and $R^{51}$ are each independently a hydrogen atom, an alkyl group, —$(CH_2)_s$—OH (s is as defined above) or an alkoxyalkyl group, and
$R^{48}$ and $R^{49}$ are each independently a hydrogen atom, an alkyl group, —CO-alkyl or —CO—O—alkyl, and
$R^{46}$ is a hydrogen atom, —CO—$R^{52}$ or —$SO_2$—$R^{52}$
wherein $R^{52}$ is an alkyl group, an alkoxy group, —NH-alkyl or —N(-alkyl)$_2$ or
$R^{30}$ and $R^{31}$ in combination form

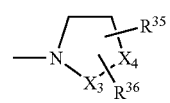

($X_3$, $X_4$, $R^{35}$ and $R^{36}$ are as defined above), or
$R^4$ and $R^5$ in combination may form —O-alkylene-O—,
a prodrug thereof or a pharmaceutically acceptable salt thereof.

2. The triazole compound of claim 1, wherein Z is —(CH($R^{14}$))$_p$— and p is 0, a prodrug thereof or a pharmaceutically acceptable salt thereof.

3. The triazole compound of claim 2, wherein Y is a $C_{3-8}$ cycloalkyl group, a prodrug thereof or a pharmaceutically acceptable salt thereof.

4. The triazole compound of claim 3, wherein $Ar^1$ is a phenyl group, a prodrug thereof or a pharmaceutically acceptable salt thereof.

5. The triazole compound of claim 4, wherein $R^2$ and $R^3$ are each independently a halogen atom or a hydrogen atom, a prodrug thereof or a pharmaceutically acceptable salt thereof.

6. The triazole compound of claim 1, wherein $Ar^2$ is a phenyl group, $R^4$ is a hydrogen atom and $R^5$ is —CO—N($R^{28}$)($R^{29}$), a prodrug thereof or a pharmaceutically acceptable salt thereof.

7. The triazole compound of claim 6, wherein $R^{28}$ and $R^{29}$ are each independently a hydrogen atom or an alkyl group, a prodrug thereof or a pharmaceutically acceptable salt thereof.

8. The triazole compound of claim 1, wherein $Ar^2$ is a phenyl group, $R^4$ is a hydrogen atom and $R^5$ is —$N(R^{30})(R^{31})$ wherein $R^{30}$ is a hydrogen atom and $R^{31}$ is —$(CH_2)_X$—CO—$R^{41}$, a prodrug thereof or a pharmaceutically acceptable salt thereof.

9. The triazole compound of claim 8, wherein X is 0 and $R^{41}$ is an alkoxy group, a prodrug thereof or a pharmaceutically acceptable salt thereof.

10. The triazole compound of claim 8, wherein X is 0 and $R^{41}$ is —$(CH_2)_s$—$N(R^{42})(R^{43})$, a prodrug thereof or a pharmaceutically acceptable salt thereof.

11. The triazole compound of claim 10, wherein s is 0, $R^{42}$ is a hydrogen atom and $R^{43}$ is an alkoxy group, a prodrug thereof or a pharmaceutically acceptable salt thereof.

12. The triazole compound of claim 1, wherein $Ar^2$ is a phenyl group, $R^4$ is a hydrogen atom and $R^5$ is —$N(R^{30})(R^{31})$ wherein $R^{30}$ and $R^{31}$ are joined to form

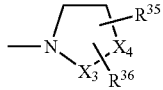

and $X_3$ is —CO—, a prodrug thereof or a pharmaceutically acceptable salt thereof.

13. The triazole compound of claim 12, wherein $X_4$ is —O—, a prodrug thereof or a pharmaceutically acceptable salt thereof.

14. The triazole compound of claim 1, which is
3—chloro—4-[4-methyl-5-(1-phenyl-cyclopropyl)-4H-[1,2,4]triazol-3-yl]-benzamide,
{3-chloro-4-[4-methyl-5-(1-phenylcyclopropyl)-4H-[1,2,4]triazol-3-yl]benzoyl}morpholine hydrochloride,
3-chloro-N-methyl-4-[4-methyl-5-(1-phenylcyclopropyl)-4H-[1,2,4]triazol-3-yl]benzamide hydrochloride,
3-chloro-N,N-dimethyl-4-[4-methyl-5-(1-phenylcyclopropyl)-4H-[1,2,4]triazol-3yl]benzamide hydrochloride,
3-chloro-N-(2-hydroxy-ethyl)-4-[4-methyl-5-(1-phenylcyclopropyl)-4H-[1,2,4]triazol-3-yl]benzamide,
3-chloro-N-isopropyl-4-[4-methyl-5-(1-phenylcyclopropyl)4H-[1,2,4]triazol-3-yl]benzamide,
{3-chloro-4-[4-methyl-5-(1-phenyl-cyclopropyl)-4H[1,2,4]triazol-3-yl]benzoyl}piperidine hydrochloride,
{3-chloro-4-[4-methyl-5-(1-phenylcyclopropyl)-4H[1,2,4]triazol-3-yl]benzoyl}-(4-hydroxy)piperidine,
N-carbamoylmethyl-3-chloro-4-[4-methyl-5-(1-phenylcyclopropyl)-4H-[1,2,4]triazol-3-yl]benzamide,
3-chloro-4-[4-methyl-5-(1-phenylcyclopropyl)-4H-[1,2,4]triazol-3-yl]-N-(2,2,2-trifluoro -ethyl)-benzamide hydrochloride,
N-(2-acetylamino)ethyl-3-chloro-4-[4-methyl-5-(1-phenylcyclopropyl)-4H-[1,2,4]triazol-3-yl]benzamide hydrochloride,
3-chloro-N-(2-methoxy)ethyl-4-[4-methyl-5-(1-phenylcyclopropyl)-4H-[1,2,4]triazol-3-yl]benzamide hydrochloride,
1-acetyl-(4-{3-Chloro-4-[4-methyl-5-(1-phenylcyclopropyl)-4H-[1,2,4]triazol-3-yl]benzoyl}piperazine hydrochloride,
3-chloro-N-(2-dimethylamino)ethyl-4-[4-methyl-5-(1-phenylcyclopropyl)-4H-[1,2,4]triazol-3-yl]benzamide,
3-chloro-4-[4-methyl-5-(1-phenylcyclopropyl)-4H-[1,2,4]triazol-3-yl]-N-(2-morpholin-4-yl)ethylbenzamide,
4-[4-methyl-5-(1-phenylcyclopropyl)-4H-[1,2,4]triazol-3-yl]-3-methoxybenzamide,
3-chloro-4-{4-methyl-5-[1-(4-fluorophenyl)cyclopropyl]-4H-[1,2,4]triazol-3-yl}benzamide,
3-chloro-N-methyl-4-{4-methyl-5-[1-(4-fluoro-phenyl)cyclopropyl]-4H-[1,2,4]triazol-3-yl}benzamide,
4-[4-isopropyl-5-(1-phenylcyclopropyl)-4H-[1,2,4]triazol-3-yl]benzamide,
3-chloro-4-[4-methyl-5-(1-thiophen-2-yl)cyclopropyl-4H-[1,2,4]triazol-3-yl]benzamide,
4-{5-[1-(4-fluorophenyl)cyclopropyl]-4-isopropyl-4H-[1,2,4]triazol-3-yl}benzamide,
4-chloro-3-{5-[1-(4-fluorophenyl)cyclopropyl]-4-methyl-4H-[1,2,4]triazol-3-yl}benzamide,
4-chloro-3-{5-[1-phenylcyclopropyl]-4-methyl-4H-[1,2,4]triazol-3-yl}benzamide,
3-chloro-4-[4-ethyl-5-(1-phenylcyclopropyl)-4H-[1,2,4]triazol-3-yl]benzamide,
3-chloro-4-{4-ethyl-5-[1-(4-fluorophenyl)cyclopropyl]-4H-[1,2,4]triazol-3-yl}benzamide,
3-[4-isopropyl-5-(1-phenylcyclopropyl)-4H-[1,2,4]triazol-3-yl]benzamide,
3-{5-[1-(4-fluoro-phenyl)cyclopropyl]-4-isopropyl-4H-[1,2,4]triazol-3-yl}benzamide,
N-{3-chloro-4-[4-methyl-5-(1-phenylcyclopropyl)-4H-[1,2,4]triazol-3-yl]phenyl}-1-morpholinecarboxamide,
3-{3-chloro-4-[4-methyl-5-(1-phenylcyclopropyl)-4H-[1,2,4]triazol-3-yl]-phenyl}-1,1-dimethylurea,
{3-chloro-4-[4-methyl-5-(1-phenylcyclopropyl)-4H-[1,2,4]triazol-3-yl]-phenyl}urea,
ethyl N-{3-Chloro-4-[4-methyl-5-(1-phenyl-cyclopropyl)-4H-[1,2,4]triazol-3-yl]-phenyl}-carbamate,
N-{3-chloro-4-[4-methyl-5-(1-phenylcycloproppyl)-4H-[1,2,4]triazol-3-yl]phenyl}-1-(4-methoxypiperidine)carboxamide,
N-{3-chloro-4-[4-methyl-5-(1-phenylcycloproppyl)-4H-[1,2,4]triazol-3-yl]phenyl}-1-(3-hydroxypiperidine)carboxamide,
N-{3-chloro-4-[4-methyl-5-(1-phenylcycloproppyl)-4H-[1,2,4]triazol-3-yl]phenyl}-1-(4-hydroxypiperidine)carboxamide,
1-{3-chloro-4-[4-methyl-5-(1-phenylcyclopropyl)-4H-[1,2,4]triazol-3-yl]-phenyl}-3-methoxyurea,
1-{3-chloro-4-[4-methyl-5-(1-phenylcyclopropyl)-4H-[1,2,4]triazol-3-yl]phenyl}-3-hydroxy -3-methylurea,
1-(3-chloro-4-{5-[1-(4-fluorophenyl)cyclopropyl]-4-methyl-4H-[1,2,4]triazol-3-yl}phenyl)-3-methoxyurea,
1-(4-{5-[1-(4-fluorophenyl)cyclopropyl]-4-isopropyl-4H-[1,2,4]triazol-3-yl}phenyl)-3-methoxyurea,
1-(3-{5-[1-(4-fluorophenyl)cyclopropyl]-4-isopropyl-4H-[1,2,4]triazol-3-yl}phenyl)-3-methoxyurea,
3-{3-chloro-4-[4-methyl-5-(1-phenylcyclopropyl)-4H-[1,2,4]triazol-3-yl]-phenyl}oxazolidin -2-one,
1-{3-chloro-4-[4-methyl-5-(1-phenylcyclopropyl)-4H-[1,2,4]triazol-3-yl]phenyl}imidazolidin-2-one,
3-(3-chloro-4-{5-[1-(4-fluoro-phenyl)cyclopropyl]-4-methyl-4H-[1,2,4]triazol-3-yl}phenyl)oxazolidin-2-one,
3-(4-{5-[1-(4-fluorophenyl)cyclopropyl]-4-isopropyl-4H-[1,2,4]triazol-3-yl}phenyl)oxazolidin-2-one,
3-(4-chloro-3-{5-[1-(4-fluorophenyl)cyclopropyl]-4-methyl-4H-[1,2,4]triazol-3-yl}phenyl)oxazolidin-2-one,
3-(3-{5-[1-(4-fluorophenyl)cyclopropyl]-4-isopropyl-4H-[1,2,4]triazol-3-yl}phenyl)oxazolidin-2-one, methyl N-(4-chloro-3-{5-[1-(4-fluorophenyl)cyclopropyl]-4-methyl-4H-[1,2,4]triazol-3-yl}phenyl)carbamate,
a prodrug thereof or a pharmaceutically acceptable salt thereof.

15. The triazole compound of claim 1, which is 3-chloro-4-[4-methyl-5-(1-phenyl-cyclopropyl)-4H-[1,2,4]triazol-3-yl]-benzamide,
{3-chloro-4-[4-methyl-5-(1-phenylcyclopropyl)-4H-[1,2,4]triazol-3-yl]benzoyl}morpholine hydrochloride,
3-chloro-N-methyl-4-[4-methyl-5-(1-phenylcyclopropyl)-4H-[1,2,4]triazol-3-yl]benzamide hydrochloride,
3-chloro-N,N-dimethyl-4-[4-methyl-5-(1-phenylcyclopropyl)-4H-[1,2,4]triazol-3-yl]benzamide hydrochloride,
3-chloro-N-(2-hydroxy-ethyl)-4-[4-methyl-5-(1-phenyl-cyclopropyl)-4H-[1,2,4]triazol-3-yl]benzamide,
3-chloro-N-isopropyl-4-[4-methyl-5-(1-phenylcyclopropyl)-4H-[1,2,4]triazol-3-yl]benzamide,
{3-chloro-4-[4-methyl-5-(1-phenyl-cyclopropyl)-4H[1,2,4]triazol-3-yl]benzoyl}piperidine hydrochloride,
{3-chloro-4-[4-methyl-5-(1-phenylcyclopropyl)-4H[1,2,4]triazol-3-yl]benzoyl}-(4-hydroxy)piperidine,
N-carbamoylmethyl-3-chloro-4-[4-methyl-5-(1-phenyl-cyclopropyl)-4H-[1,2,4]triazol-3-yl]benzamide,
3-chloro-4-[4-methyl-5-(1-phenylcyclopropyl)-4H-[1,2,4]triazol-3-yl]-N-(2,2,2-trifluoro -ethyl)-benzamide hydrochloride,
N-(2-acetylamino)ethyl-3-chloro-4-[4-methyl-5-(1-phenylcyclopropyl)-4H-[1,2,4]triazol-3-yl]benzamide hydrochloride,
3-chloro-N-(2-methoxy)ethyl-4-[4-methyl-5-(1-phenyl-cyclopropyl)-4H-[1,2,4]triazol-3-yl]benzamide hydrochloride,
1-acetyl-(4-{3-Chloro-4-[4-methyl-5-(1-phenylcyclopropyl)-4H-[1,2,4]triazol-3-yl]benzoyl}piperazine hydrochloride,
3-chloro-N-(2-dimethylamino)ethyl-4-[4-methyl-5-(1-phenylcyclopropyl)-4H-[1,2,4]triazol-3-yl]benzamide,
3-chloro-4-[4-methyl-5-(1-phenylcyclopropyl)-4H-[1,2,4]triazol-3-yl]-N-(2-morpholin-4-yl)ethylbenzamide,
4-[4-methyl-5-(1-phenylcyclopropyl)-4H-[1,2,4]triazol-3-yl]-3-methoxybenzamide,
3-chloro-4-{4-methyl-5-[1-(4-fluorophenyl)cyclopropyl]-4H-[1,2,4]triazol-3-yl}benzamide,
3-chloro-N-metyl-4-{4-methyl-5-[1-(4-fluoro-phenyl)cyclopropyl]-4H-[1,2,4]triazol-3-yl}benzamide,
4-[4-isopropyl-5-(1-phenylcyclopropyl)-4H-[1,2,4]triazol-3-yl]benzamide,
3-chloro-4-[4-methyl-5-(1-thiophen-2-yl)cyclopropyl-4H-[1,2,4]triazol-3-yl]benzamide,
4-{5-[1-(4-fluorophenyl)cyclopropyl]-4-isopropyl-4H-[1,2,4]triazol-3-yl}benzamide,
4-chloro-3-{5-[1-(4-fluorophenyl)cyclopropyl]-4-methyl-4H-[1,2,4]triazol-3-yl}benzamide,
4-chloro-3-{5-[1-phenylcyclopropyl]-4-methyl-4H-[1,2,4]triazol-3-yl}benzamide,
3-chloro-4-[4-ethyl-5-(1-phenylcyclopropyl)-4H-[1,2,4]triazol-3-yl]benzamide,
3-chloro-4-{4-ethyl-5-[1-(4-fluorophenyl)cyclopropyl]-4H-[1,2,4]triazol-3-yl}benzamide,
3-[4-isopropyl-5-(1-phenylcyclopropyl)-4H-[1,2,4]triazol-3-yl]benzamide,
3-{5-[1-(4-fluoro-phenyl)cyclopropyl]-4-isopropyl-4H-[1,2,4]triazol-3-yl}benzamide,
a prodrug thereof or a pharmaceutically acceptable salt thereof.

16. The triazole compound of claim 1, which is
N-{3-chloro-4-[4-methyl-5-(1-phenylcycloproppyl)-4H-[1,2,4]triazol-3-yl]phenyl}-1-morpholinecarboxamide,
3-{3-chloro-4-[4-methyl-5-(1-phenylcyclopropyl)-4H-[1,2,4]triazol-3-yl]-phenyl}-1,1-dimethylurea,
{3-chloro-4-[4-methyl-5-(1-phenylcyclopropyl)-4H-[1,2,4]triazol-3-yl]-phenyl}urea,
ethyl N-{3-Chloro-4-[4-methyl-5-(1-phenyl-cyclopropyl)-4H-[1,2,4]triazol-3-yl]-phenyl}-carbamate,
N-{3-chloro-4-[4-methyl-5-(1-phenylcycloproppyl)-4H-[1,2,4]triazol-3-yl]phenyl}-1-(4-methoxypiperidine) carboxamide,
N-{3-chloro-4-[4-methyl-5-(1-phenylcycloproppyl)-4H-[1,2,4]triazol-3-yl]phenyl}-1-(3-hydroxypiperidine) carboxamide,
N-{3-chloro-4-[4-methyl-5-(1-phenylcycloproppyl)-4H-[1,2,4]triazol-3-yl]phenyl}-1-(4-hydroxypiperidine) carboxamide,
1-{3-chloro-4-[4-methyl-5-(1-phenylcyclopropyl)-4H-[1,2,4]triazol-3-yl]-phenyl}-3-methoxyurea,
1-{3-chloro-4-[4-methyl-5-(1-phenylcyclopropyl)-4H-[1,2,4]triazol-3-yl]phenyl}-3-hydroxy -3-methylurea,
1-(3-chloro-4-{5-[1-(4-fluorophenyl)cyclopropyl]-4-methyl-4H-[1,2,4]triazol-3-yl}phenyl)-3-methoxyurea,
1-(4-{5-[1-(4-fluorophenyl)cyclopropyl]-4-isopropyl-4H-[1,2,4]triazol-3-yl}phenyl)-3-methoxyurea,
1-(3-{5-[1-(4-fluorophenyl)cyclopropyl]-4-isopropyl-4H-[1,2,4]triazol-3-yl}phenyl)-3-methoxyurea,
a prodrug thereof or a pharmaceutically acceptable salt thereof.

17. The triazole compound of claim 1, which is
3-{3-chloro-4-[4-methyl-5-(1-phenylcyclopropyl)-4H-[1,2,4]triazol-3-yl]-phenyl}oxazolidin -2-one,
1-{3-chloro-4-[4-methyl-5-(1-phenylcyclopropyl)-4H-[1,2,4]triazol-3-yl]phenyl}imidazolidin-2-one,
3-(3-chloro-4-{5-[1-(4-fluoro-phenyl)cyclopropyl]-4-methyl-4H-[1,2,4]triazol-3-yl}phenyl)oxazolidin-2-one,
3-(4-{5-[1-(4-fluorophenyl)cyclopropyl]-4-isopropyl-4H-[1,2,4]triazol-3-yl}phenyl)oxazolidin-2-one,
3-(4-chloro-3-{5-[1-(4-fluorophenyl)cyclopropyl]-4-methyl-4H-[1,2,4]triazol-3-yl}phenyl)oxazolidin-2-one,
3-(3-{5-[1-(4-fluorophenyl)cyclopropyl]-4-isopropyl-4H-[1,2,4]triazol-3-yl}phenyl)oxazolidin-2-one,
a prodrug thereof or a pharmaceutically acceptable salt thereof.

18. A pharmaceutical composition comprising the triazole compound of claim 1, a prodrug thereof or a pharmaceutically acceptable salt thereof, and a pharmaceutically acceptable carrier.

* * * * *